US008613616B2

(12) United States Patent
Rose et al.

(10) Patent No.: US 8,613,616 B2
(45) Date of Patent: Dec. 24, 2013

(54) ILLUMINATION SYSTEM FOR DENTISTRY APPLICATIONS

(75) Inventors: Eric P. Rose, Tarzana, CA (US); Robert Hayman, Los Angeles, CA (US); Stuart Karten, Venice, CA (US); Dennis Schroeder, Hermosa Beach, CA (US); Steve Piorek, Los Angeles, CA (US); Douglas H. Grambush, Corona Del Mar, CA (US); Marc Orloff, Altadena, CA (US); Nancy N. Quan, North Hills, CA (US); Younes Shabany, San Jose, CA (US); William Dorfman, Beverly Hills, CA (US); Kenneth Rosenblood, Los Angeles, CA (US); Dac Vu, Tustin, CA (US); Curt Kenneth Deckert, Santa Ana, CA (US); Brian Kennedy, Claremont, CA (US); Christopher N. Quan, Houston, TX (US)

(73) Assignee: Discus Dental, LLC, Culver City, CA (US)

( * ) Notice: Subject to any disclaimer, the term of this patent is extended or adjusted under 35 U.S.C. 154(b) by 0 days.

(21) Appl. No.: 11/925,631

(22) Filed: Oct. 26, 2007

(65) Prior Publication Data
US 2008/0096156 A1    Apr. 24, 2008

Related U.S. Application Data

(63) Continuation of application No. 11/173,839, filed on Jun. 30, 2005, now abandoned, and a continuation of application No. 29/220,642, filed on Jan. 4, 2005, now Pat. No. Des. 542,947, and a continuation of (Continued)

(51) Int. Cl.
*A61C 3/00*    (2006.01)
*A61C 5/00*    (2006.01)

(52) U.S. Cl.
USPC ............................................. 433/29; 433/140

(58) Field of Classification Search
USPC ...................... 433/29, 140, 215; 362/572, 573
See application file for complete search history.

(56) References Cited

U.S. PATENT DOCUMENTS 4,952,143 A * 8/1990 Becker et al. ................... 433/32
5,473,524 A   12/1995 Behringer (Continued)

FOREIGN PATENT DOCUMENTS

WO    2004/108003    12/2004

*Primary Examiner* — Heidi M Eide

(57) ABSTRACT

A dental illumination system includes an adjustable self-supporting frame and a lamp head coupled to the frame. The lamp head includes a housing and a spacer having formations that is adapted to removably mechanically couple the lamp head to a reference device, again having formations, for facilitating illumination of a tooth by a light source contained within the lamp head. The spacer and lamp head may be formed integrally. If formed separately, both the lamp head and the spacer may include formations.

21 Claims, 47 Drawing Sheets

Related U.S. Application Data application No. 29/220,680, filed on Jan. 4, 2005, now Pat. No. Des. 537,192, and a continuation of application No. 29/220,679, filed on Jan. 4, 2005, now Pat. No. Des. 543,937, and a continuation of application No. 29/232,670, filed on Jun. 22, 2005, now Pat. No. Des. 538,960, and a continuation of application No. 29/232,671, filed on Jun. 22, 2005, now Pat. No. Des. 539,956.

(60) Provisional application No. 60/585,224, filed on Jul. 2, 2004, provisional application No. 60/641,462, filed on Jan. 4, 2005, provisional application No. 60/647,725, filed on Jan. 26, 2005, provisional application No. 60/647,723, filed on Jan. 26, 2005, provisional application No. 60/658,517, filed on Mar. 3, 2005, provisional application No. 60/641,469, filed on Jan. 4, 2005, provisional application No. 60/647,580, filed on Jan. 26, 2005, provisional application No. 60/641,461, filed on Jan. 4, 2005, provisional application No. 60/641,468, filed on Jan. 4, 2005, provisional application No. 60/647,612, filed on Jan. 26, 2005, provisional application No. 60/647,593, filed on Jan. 26, 2005, provisional application No. 60/604,577, filed on Aug. 25, 2004, provisional application No. 60/594,297, filed on Mar. 25, 2005, provisional application No. 60/631,267, filed on Nov. 26, 2004, provisional application No. 60/594,327, filed on Mar. 30, 2005, provisional application No. 60/664,696, filed on Mar. 22, 2005.

(56) References Cited

U.S. PATENT DOCUMENTS

| | | | |
|---|---|---|---|
| 6,193,510 B1 * | 2/2001 | Tsimerman | 433/29 |
| 6,536,068 B1 | 3/2003 | Yang et al. | |
| 6,761,561 B2 | 7/2004 | Mandelkern et al. | |
| 2002/0168603 A1 | 11/2002 | Cao | |
| 2003/0091954 A1 * | 5/2003 | West et al. | 433/29 |
| 2003/0115694 A1 * | 6/2003 | Pace | 15/22.1 |
| 2003/0157456 A1 * | 8/2003 | Plocharczyk | 433/29 |
| 2004/0257438 A1 * | 12/2004 | Doguchi et al. | 348/65 |
| 2005/0143793 A1 * | 6/2005 | Korman et al. | 607/94 |
| 2005/0239018 A1 | 10/2005 | Green et al. | |
| 2006/0003284 A1 * | 1/2006 | Sale et al. | 433/29 |

* cited by examiner

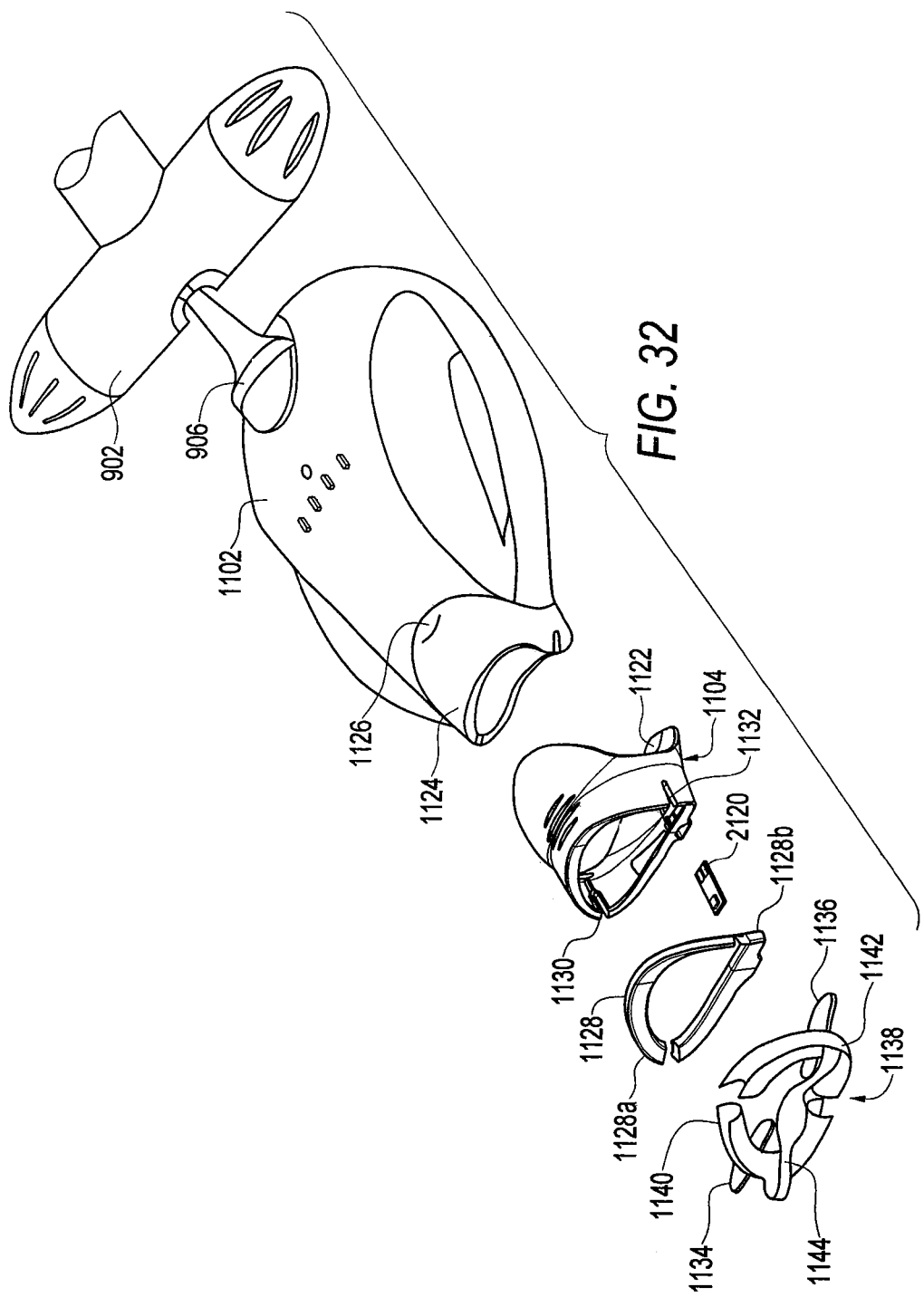

ILLUMINATION SYSTEM FOR DENTISTRY APPLICATIONS

CROSS-REFERENCE TO RELATED APPLICATIONS

This application is a continuation of application Ser. No. 11/173,839, filed on Jun. 30, 2005 now abandoned, which claims the benefit of U.S. provisional patent application Ser. No. 60/585,224, filed Jul. 2, 2004, entitled "Dental Light Devices with Phase Change Heat Sink"; 60/641,462, filed Jan. 4, 2005, entitled "Boom Hinge For a Dental Lamp"; 60/647,725, filed Jan. 26, 2005, entitled "Automatic Control for a Dental Whitening Lamp"; 60/647,723, filed Jan. 26, 2005, entitled "Boom Hinge For A Dental Lamp"; 60/658,517, filed Mar. 3, 2005, entitled "Apparatus and Method For Radiation Spectrum Shifting in Dentistry Application"; 60/641,469, filed Jan. 4, 2005, entitled "Lamp For Dentistry Applications"; 60/647,580, filed Jan. 26, 2005, entitled "Light Guide For Dental Whitening Lamp"; 60/641,461, filed Jan. 4, 2005, entitled "Support Structure For A Dental Lamp"; 60/641,468, filed Jan. 4, 2005, entitled "Light Guide For A Dental Whitening Lamp"; 60/647,612, filed Jan. 26, 2005, entitled "Light Path Apparatus For A Dental Lamp"; 60/647,593, filed Jan. 26, 2005, entitled "Support Structure For A Dental Lamp"; 60/604,577, filed Aug. 25, 2004, entitled "Lip Retractors"; 60/594,297, filed Mar. 25, 2005, entitled "Curing Light Having A Detachable Tip"; 60/631,267, filed Nov. 26, 2004, entitled "Curing Light Having A Reflector"; 60/594,327, filed on Mar. 30, 2005, entitled, "Curing Light"; and 60/664,696, filed Mar. 22, 2005, entitled "Curing Light Having A Detachable Tip"; the contents of all of which are hereby incorporated by reference.

This application is also a continuation of application Ser. No. 11/173,839, filed on Jun. 30, 2005 which is a continuation-in-part of the following U.S. design applications No. 29/220,642, filed Jan. 4, 2005 now U.S. Pat. No. D542,947, entitled "Lamp For Dentistry Applications"; 29/220,680, filed Jan. 4, 2005 now U.S. Pat. No. D537,192, entitled "Light Guide For Dentistry Applications"; 29/220,679, filed Jan. 4, 2005 now U.S. Pat. No. D543,937, entitled "Support Structure For A Lamp For Dentistry"; 29/232,670, filed on Jun. 22, 2005 now U.S. Pat. No. D538,960, entitled "Support Structure for Dental Applications"; 29/232,671, filed on Jun. 22, 2005 now U.S. Pat. No. D539,956, entitled "Support Structure for Dental Applications"; all of which are incorporated herein by reference.

The present application includes claims that may be related to the claims of co-pending U.S. patent application Ser. Nos. 11/631,222, filed Jun. 30, 2005, entitled "Dental Light Devices Having an Improved Heat Sink" (US Pub. No. 2009/0233254); 11/173,709, filed Jun. 30, 2005, entitled "Voice Alert in Dentistry" (US Pub. No. 2006/0008787); 11/173,297, filed Jun. 30, 2005, entitled "Retracting Devices" (US Pub. No. 2006/0069316); 11/173,076, filed Jun. 30, 2005, entitled "Curing Light Capable of Multiple Wavelengths" (US Pub. No. 2006/0040231); 11/173,264, filed Jun. 30, 2005, entitled "Curing Light" (US Pub. No. 2006/0024638); 11/173,371, filed Jun. 30, 2005, entitled "Support System for Dentistry" (US Pub. No. 2006/0029904); 11/173,734, filed Jun. 30, 2005, entitled "Light Guide for Dentistry Applications" (US Pub. No. 2006/0029901); and 11/174,363, filed Jun. 30, 2005, entitled "Automatic Control for Dental Applications" (US Pub. No. 2006/0029902); the contents of all of which are hereby incorporated by reference.

FIELD OF THE INVENTION

This invention relates to illumination systems used in dentistry. Specifically, this invention relates to illumination systems used in dental curing, dental whitening or imaging.

BACKGROUND OF THE INVENTION

A tooth is comprised of an inner dentin layer and an outer hard enamel that is coated with a protective layer called the acquired pellicle. The enamel layer is composed of hydroxyapatite crystals that create a somewhat porous surface. The pellicle or the enamel can become stained or discolored. It is believed that the porous nature of the enamel layer is what allows staining agents and discoloring substances to permeate the enamel and discolor the tooth.

Tooth discoloration has a number of causes. For example, the teeth may become stained by coffee or tea drinking, or by the use of tobacco products, or by drinking water with a high mineral content.

One solution to the staining problem is through tooth bleaching. Some dentifrices, like toothpastes, gels, and powders, contain active oxygen or hydrogen peroxide liberating bleaching agents including peroxides, percarbonates and perborates of the alkali and alkaline earth metals or complex compounds containing hydrogen peroxide.

Dental bleaching can be done either in a dental office or at home. Bleaching in a dental office generally employs compositions activatable with the aid of light sources having the appropriate wavelength outputs in order to speed up the process. Additionally, the bleaching compositions used in a dental office typically contain a higher percentage concentration of bleaching agents than the bleaching compositions found in home applications.

In addition to staining, tooth decay, resulting in cavities or other damages can also result. In the field of tooth restoration and repair, dental cavities are often filled and/or sealed with compounds that are photosensitive, either to visible and/or ultraviolet light. These compounds, commonly known as light-curable compounds, are placed within dental cavity preparations or onto dental surfaces and are cured when exposed to light from a dental curing light device.

Unlike dental curing and imaging processes, which are generally relatively fast processes, dental bleaching takes a much longer time, sometimes amounting to more than an hour per office visit. On the other hand, dental restoration is often an unwelcome experience. Therefore, it is advantageous that a person undergoing the processes, either dental restoration or bleaching, be as comfortable as possible.

The process is generally performed in a dentist's chair. Typically a dentist's chair has a wide range of adjustability such that a patient may be placed in a wide range of positions from a nearly full reclining position to a nearly upright position. In order to effectively accomplish the whitening or restoration process, a light source needs to be aligned with the mouth. The wide range of dentist's chair positions can make this alignment difficult.

Further considerations in the process of dental procedures include the ability to maintain cleanliness of the light source, and particularly of any part that comes into contact with the patient. Further, the process of whitening is, for example, optimized, that is, the light source is on as long as necessary to whiten the teeth to the desired degree. Still further, it is desirable that the light source be as efficient as possible. An efficient lamp tends to be cooler and therefore safer than an inefficient lamp. Also, an efficient lamp requires less energy to run than an inefficient lamp.

It remains desirable to have an efficient and comfortable apparatus and method for dental whitening, curing and imaging.

SUMMARY OF THE INVENTION

The present invention is directed to a system, an apparatus and method for dental whitening, curing or imaging, that is efficient, comfortable for the patient and further includes improved safety, maintenance and operating features.

The present invention is also directed to an alignment system to facilitate faster patient set up and optimal results.

The alignment system includes an apparatus for positioning a dental illumination device relative to a subject, including a lamp system, a reference device, and a spacer for engaging both the reference device and the lamp system for positioning the lamp system at a predetermined distance from the reference device.

In one embodiment, the reference device and the spacer include formations that removably inter-engage as the reference device and spacer become apposed.

In another embodiment, the spacer and the lamp system include formations that removably inter-engage as the spacer and the lamp system become apposed.

In a further embodiment, the spacer and at least one of its formations are integrally formed with the lamp system.

The inter-engaging formations serve to stabilize the spacer axially and against twisting.

Furthermore, the present invention includes a support mechanism that is unobtrusive, easily adjustable, and able to provide positioning in multiple degrees of freedom so as to be adaptable to the requirements of patients of various sizes.

The lamp system and a support system include formations that removably inter-engage as the lamp system and the support system become apposed.

According to a first embodiment of the invention, a dental whitening or curing light source includes at least one light source such as, for example, an ultraviolet light source for activating a dental whitening or curing composition. The light source may include a lamp, an arc lamp such as a halogen light source, semiconductor light emitting devices, light-emitting chips such as an LED, a solid state LED, an LED array, a fluorescent bulb, and so on. In the case of dental imaging, the light source may include the above in addition to a laser, an x-ray or even an infrared source. According to a second embodiment of the invention, multiple light sources arranged in a geometric arrangement may be used. In one aspect, an illumination frame may be disposed inside the lamp head housing. In another aspect, the illumination frame may be in place of the lamp head housing as a self-contained structure. In a further aspect, the illumination frame may be in addition to the lamp head housing. The light sources may be collectively powered or individually powered. If individually powered, each of the individual light sources may be turned on or off separately, as desired.

In one embodiment, the illumination frame may be adapted to be coupled to the spacer and the spacer is adapted to be coupled to the reference device. In another aspect, the spacer may be an integral part of the lamp system, adapted to be coupled to the reference device. According to a further aspect, an illumination frame includes at least one light source set in the illumination frame to illuminate at least one tooth in the mouth of a dental patient.

In one embodiment, the illumination frame may, for example, conform to the jaw of a patient and have a first end and a second end. The first and second ends include a first and second formations, such as slots, configured to mate with a first and a second formation, such as a wing-like member, respectively, of a reference device such as a lip retracting device. The arcuate shape of the illumination system may be configured to follow the curvature of the human head so that the light sources are substantially equidistant from the various teeth in a dental patient. The light source may be capable of whitening, curing or imaging.

In another embodiment of the invention, the illumination frame is rectangular with a first slotted structure on one side of the rectangle and a second slotted structure on the opposite side of the rectangle configured to mate with wing-like members on a lip retracting device worn by a dental patient. In one embodiment of the invention, a path is provided from a light source to a target such as a whitening composition disposed on a tooth surface, a filling compound residing either on the surface or in the cavity of a tooth, or a tooth for imaging. In one aspect, the light path includes a light source capabale of imaging, whitening or curing. In another aspect, the light path includes a light source and at least one reflector integral to the light source. According to a further aspect, the invention includes a second reflector having an axial cavity with a first aperture at an end proximate the light source and a second aperture distal to the light source. The second reflector includes a reflective internal surface adapted to direct light from the light source towards the second aperture by reflection. In one embodiment, an optical lens is disposed within the second reflector. According to another embodiment, the optical lens includes at least one curved surface and is adapted to direct light from the light source towards the second aperture by refraction. According to yet another embodiment, an optical filter is disposed coincident with the second aperture. The optical filter serves to impede the passage of various wavelengths of light while allowing the passage of other wavelengths. In a further embodiment, the optical filter serves to prevent, for example, most light having a wavelength characterized as in the infrared range from passing through the second aperture to the target, if desired. In contrast, light in the ultraviolet and/or visible ranges are allowed to pass, if desired.

According to a further embodiment of the invention, a light path apparatus including a reflector, a lens, a filter, and a diffusion element is disclosed. The diffusing element may be used to spatially homogenize the spectrum output of a light source. According to one aspect of the invention, a diffusing element may be employed to produce scattering of light at an input surface thereof to generate a randomized and spatially equalized output light pattern. According to another aspect of the invention, the diffusing element includes a textured surface adapted to provide scattering of received light. In a further aspect, the diffusing element includes a frosted surface, for example, a frosted glass portion or a frosted glass produced by etching. In another example, a frosted plastic surface element is employed. As in the case of a frosted glass element, the plastic element may be frosted by etching, or by a mechanical crazing process. In other examples, the diffusing element may include a textured surface having a plurality of striations thereon, a plurality of ridges, a corrugated pattern, a plurality of microscopic hemispherical bumps, a plurality of microscopic conical projections, or any other surface feature adapted to produce the desired scattering of light. In still other examples of the invention, the diffusing element includes a transparent or translucent material having a plurality of suitably sized particles suspended in a layer, or otherwise throughout a body of the diffusing element. The suspended particles may be spherical, or may exhibit any other appropriate physical geometry.

According to one embodiment of the invention, the diffusing element is disposed between the light source and a lens. The lens serves to refract light received from the light source, directly or indirectly, by reflection from various surfaces, and to refract light towards the target area. In one embodiment, the lens includes a substantially rectangular periphery. In another embodiment, a peripheral edge of the lens is substantially circular, elliptical, or otherwise configured according to the particular requirements of any given embodiment of the invention. In a further embodiment, the lens includes a curved output surface region and a substantially flat input region. In yet another embodiment, the lens includes a curved input region and a substantially flat output region. In still another embodiment of the invention, the lens includes a curved output region, and an input surface that includes both curved and flat regions, where the curved region minimizes refractive characteristics of the lens within a particular area while providing desirable refraction in other portions of the illumination pattern produced by the light source, or light source and diffusing element.

According to another embodiment of the invention, a light path apparatus including a reflector, a lens, a filter, an integrator and diffusing element is disclosed. In one aspect, according to various embodiments of the invention, a light path apparatus includes a housing having a reflector surface and an integrator surface. The reflector surface redirects divergent rays of light towards an input of a lens, or lens system. The integrator surface redirects divergent rays of light received from an output surface of the lens or lens system towards an output aperture of the light path apparatus.

According to one embodiment of the invention, the light path apparatus housing is formed of metal, such as, for example, formed sheet metal. In another embodiment of the invention, the light path apparatus housing is formed of a polymer material, including, for example, a reinforced polymer composite material.

In still another embodiment of the invention, the light path apparatus includes an optical filter. The optical filter serves to absorb and/or reflect light of various wavelengths, and in particular wavelengths of desirable ranges in terms of the applications of the dental lamp system. For example, where an output of the dental lamp is desired to be principally within the ultraviolet spectrum, the optical filter will absorb and otherwise reject at least some light of visible and/or infrared wavelengths.

In one embodiment of the invention, the optical filter is disposed distal to the light source, such that the diffuser element and lens are disposed between the light source device and the optical filter. In one embodiment of the invention, the optical filter is disposed immediately adjacent to, or within, an aperture at an output and of the light path apparatus. Consequently, light suitable for activating a dental whitening compound, or for any other dentistry process, is available outside of the second aperture, if present. Meanwhile, for example, infrared light, which would otherwise unduly elevate the temperature of the target area, unless useful in a dental process, is excluded from the target area, or is reduced to acceptable levels.

According to at least one embodiment of the invention, an elastomeric mounting is provided to mechanically couple the filter in position in the light path. Furthermore, one embodiment of the invention includes another elastomeric mounting disposed to mechanically couple the optical lens to a position in the light path. The elastomeric mountings serve, in various aspects of the invention, to protect the lens and filter respectively against mechanical shock and to compensate for differences in coefficient of thermal expansion present between various materials employed in the device of the invention.

According to a further embodiment of the invention, a light source and reflector assembly are disposed within a lamp housing. The lamp housing includes fixturing features adapted to hold the light source and a reflector assembly within an axial cavity of the lamp housing. The lamp housing includes a rear aperture proximate to the light source and a front aperture proximate to the second aperture of the reflector.

According to at least one embodiment of the invention, at least one wavelength transformer may be included. The wavelength transformer may act to transform shorter wavelengths outside of the useful range for whitening imaging or curing, into longer wavelengths in the useful range, thus minimizing energy waste. In one aspect, the wavelength transformer may be disposed within the lamp housing. In another aspect, the wavelength transformer may be part of the light source. In a third aspect, the wavelength transformer may be constructed into a modular device adapted to be installed or removed from the lamp housing of the whitening, imaging or curing light source, whenever desired.

In another embodiment of the invention, a grill is disposed coincident with the rear aperture. In one aspect, the grill includes perforations for heat dissipation or to allow the passage of a cooling medium, such as air.

In one embodiment of the invention, the lamp housing also includes a cooling system for maintaining the light source, and other components of the lamp head at a desirable temperature, a high operating temperature of the light source notwithstanding. In one embodiment, the cooling system includes a fan. In another embodiment, the cooling system includes a heat sink. In still another embodiment, the cooling system includes heat pipes. In another embodiment, the cooling system includes phase change materials.

According to one embodiment of the invention, the housing includes a formation such as a mechanical coupling feature in proximity to the front aperture. The mechanical coupling feature provides, according to one embodiment of the invention, a secure, removable connection between the housing and a spacer.

Housing as used herein may include structures that contained a light source or sources.

In one embodiment of the invention, the spacer may be, for example, a light guide, having a first and a second formation. The first formation is adapted to removably couple the light guide to a light source or lamp, and the second formation is adapted to removably couple the light guide to a reference device for positioning the light guide, and consequently the lamp head and/or a light source, in a substantially constant position and orientation with respect to a target. In one aspect, the light guide may have a substantially tubular or substantially ellipsoidal shape. In another aspect, the light guide may have an aperture of any shape having an aspect ratio ranging from about 1:5 to about 1:2. An aperture at a proximal end of the light guide is adapted for positioning the light guide adjacent to the front aperture of the lamp housing. A further aperture exists at a distal end of the light guide. The light guide includes formations adapted to interface with the formations of the housing. The light guide may include a second formation adapted to removably couple the light guide to a reference device for positioning the light guide, as noted above, and consequently the lamp head and the light source, in a substantially constant position and orientation with respect to a target.

In one embodiment, the light guide may be formed of a polymeric material having a spectral absorption characteristic, for example, visible light may readily pass through the walls of the light guide, while ultraviolet light may be either absorbed by the walls or, for example, may be reflected from the internal surfaces of the light guide. By allowing the transmission of visible light the light guide facilitates the installation of the light guide since the teeth of the patient may be quite visible through the walls of the light guide. By absorbing or reflecting light of ultraviolet wavelengths, the light guide serves to contain the ultraviolet radiation directed therethrough and to shield local soft tissues from the effects of such ultraviolet radiation.

The material of the light guide may be chosen to absorb and/or reflect light of one or more ranges of wavelength that impinges on the tubular inner surface. Consequently, according to one aspect of the invention, the light guide may reduce the degree to which light of the subject wavelengths escapes from the system except through the distal aperture of the light guide.

In another embodiment of the invention, the light guide is adapted to be limited to the use in the treatment of a single dental patient and may be thereafter disposable. In another embodiment, a control mechanism may be provided to inhibit the use of a light guide on additional patients after it has been once used. One aspect of the control mechanism is that the inhibition may occur during the attachment process of the light guide to the lamp system.

In one embodiment of the invention, the signal generating and record reading devices are located within the lamp housing. In another embodiment of the invention, one or more of the signal generating and record reading devices are located external to the lamp head housing.

One embodiment of the invention effects control of light guide usage by including a recording medium in the light guide, and a signal generating device elsewhere in the lamp system. In one aspect, the invention includes receipt by the recording medium of a signal from the signal generating device, and recording of a record of the recording medium corresponding to the received signal to produce a substantially permanent signal record. In another aspect of the invention, the substantially permanent signal record is read by a medium reading device and a condition of use of the particular light guide containing the recording medium is ascertained. Based on the condition of use indicated by the record, as read, a control device external to the light guide serves to allow or inhibit activation of the light source.

In one embodiment of the invention, the signal from the signal generating source is received at the recording medium by way of an electromechanical coupling, for example, wired or wireless. In another embodiment of the invention, the signal from the signal generating source is received at the recording medium by way of an optical communication channel. In a still further embodiment of the invention, the signal from the signal generating source is received at the recording medium by way of a mechanical communication channel, an acoustic communication channel, a radiofrequency communication channel, or any other communication medium that is appropriate to the particular invention embodiment.

According to one embodiment, a single-use light guide includes a write once read many times (WORM) memory device. In a particular aspect of the invention, the WORM memory device is adapted to receive a signal related to the duration of use of a related instance of a light guide, and to substantially indelibly record the information content of the signal for later use by a control subsystem of a light source.

In a further embodiment of the invention, a plurality of light guides each have an output end having a respective size, wherein the size of a particular output end corresponds to a mouth size of a particular patient or class of patients. For example, light guides in various embodiments may be provided that are most appropriate to use by a large adult, a small adult, or a child.

In one embodiment of the invention, the reference device is a lip retracting device having geometric formations adapted to receive one or more lips of a patient in a tooth restoration, imaging or whitening process.

In one aspect, the light guide and the lip retracting device provides an interlocking system for optical alignment of the light source with the target, allowing for fool-proof set up, and promoting patient safety during a dental procedure.

In another aspect, soft foam or elastomeric cushions are disposed along the edge of the light guide that interfaces with the lip retracting device to provide custom forming to each patient's profile for additional comfort.

In one embodiment, the light guide includes air vents for patient breathing comfort during the bleaching or curing treatment or during imaging.

According to the present invention, the reference device may include a lip retracting device having formations adapted for repeatably positioning a user's lips with respect to a light output port, a light guide, an examination or an imaging device such as a cone-shaped structure.

In one embodiment of the present invention, a lip retracting device includes at least two channel retainers or flanges, at least one resilient member, and at least two wing-like members or flanges, wherein each of the channel retainers includes a race, an inside side wall, an outside side wall, and each of the wing-like members is spaced away from the attachment of the resilient member. Each of the wing-like members may be adapted to fit into a formation such as a slot in an output port, a light guide, an examination or an imaging device such as a cone. In one aspect, each of the resilient members is attached to the inside side wall of two adjacent channel retainers by means of an adhesive or heat sealing, and includes two arches; and each of the wing-like flanges or members is attached to a channel retainer by means of an adhesive or heat sealing. In another aspect, each of the resilient members is integrally molded to the inside side wall of the two adjacent channel retainers and includes two arches; and each of the wing-like flanges or members is integrally molded to a channel retainer.

According to another embodiment of the invention, a lip retracting device includes at least a pad attached or molded to the resilient member about the area of the arch.

According to yet another embodiment of the invention, a lip retracting device includes at least two channel retainers, at least two wing-like flanges and a tongue retainer, the channel retainers being held in a spaced apart relationship by at least one resilient member, the wing-like flanges being integrally attached or molded to the channel retainers and the tongue retainer being attached to two of the channel retainers.

According to a further embodiment of the present invention, the lip retracting device includes four channel retainers or flanges, four resilient members, and two wing-like members or flanges, wherein each channel retainer includes a race, an inside side wall, an outside side wall; each resilient member is integrally molded or attached to two outside side walls of two adjacent channel retainers and includes an arch; and each wing-like member or flange is integrally molded or attached to a channel retainer or flange at a location that is spaced away from the attachment area of the resilient member. The attachment may be accomplished by an adhesive or heat sealing. Each of the wing-like members is adapted to fit into a formation, such as a slot in an output port, a light guide, an imaging or an examination device such as a cone.

According to yet a further embodiment of the present invention, a lip retracting device includes four channel retainers, a plurality of resilient members, and a tongue retainer, the channel retainers being held in a spaced apart relationship by at least one resilient member having an arch, and the tongue retainer being attached to two of the channel retainers by two secondary resilient members.

According to a still further embodiment of the invention, a lip retracting device includes at least two pads, attached or molded to a resilient member.

According to still another embodiment of the invention, there is provided a lip retracting device for accommodating a dental treatment composition, for example, a whitening composition. In one aspect, the retracting device may further include a unshaped channel configured to accommodate the lower, or alternatively the upper, set of a user's teeth. The unshaped channel supports the channel retainers in substantially fixed spatial relation with respect to one another. In another aspect, the arch of the retracting device may be configured to accommodate a unshaped channel.

In one aspect, any of the lip retracting devices described above may be fitted with a tab for grasping and for facilitating insertion and removal.

In one embodiment, the lip retracting device may also be adapted for use by a single patient and is thereafter disposable. One aspect of the control mechanism is that the inhibition occurs during the attachment process of the lip retracting device to the light guide.

In another embodiment, the lip retracting device useage may also be controlled by including a recording medium, for example, about the wing-like members, and a signal generating device elsewhere in the lamp system, as disclosed above for the control use of a light guide. In another example, when both the spacer and formations, for example, slots for mating with the wing-like members of the lip retracting device, are integrally part of or attached to the lamp housing, for example, to an illumination frame, the signal generating device may be present in the lamp housing.

In a further embodiment, a reference device may be held in place by the natural compression of the lips of the patient. The device includes wings that provide positioning and alignment to a mating formation on an imaging apparatus. The configuration enables patients to hold a position during imaging with comparatively little effort.

In one aspect, a reference device includes a passively held portion to anchor it to a subject of dental imaging. The reference device further includes a first alignment formation coupled to the passively held portion where the first alignment formation provides alignment to at least one dental feature. The reference device further includes a second alignment formation coupled to an imaging device where the second alignment formation is shaped and configured to mate with the first alignment formation to the imaging device in a substantially fixed position with respect to the at least one dental feature. The reference device may include a film holder coupled to the passively held portion. The film holder locates imaging film, or an imaging sensor, for imaging the at least one dental feature.

In one embodiment, the reference device may be a single-use device, and the imaging film, or imaging sensor may be integrally formed with the holder.

According to another embodiment of the invention, the lamp housing or the housing of the illumination frame includes formations, for example, a ball member having a convex spheroid surface. The ball member is adapted to be received in formations such as a ball cavity having a corresponding concave spheroid surface.

In one embodiment of the invention, the ball cavity is coupled to one end of a support boom. The support boom may be supported by a mast which is, in turn, supported by a surface-supported base. In one aspect of various embodiments, the base is a wheeled mobile base. The wheels may additionally include locking casters for enhanced maneuverability and stability, in operation or at idle.

According to one embodiment of the invention, a ball joint is formed by the combination of the ball member and ball cavity. The ball joint permits ready positioning of the lamp head, and consequently, of the front aperture of the lamp head and of a light guide coupled to the lamp head housing, in a wide variety of positions and orientations with respect to the balance of the lamp system.

In a further embodiment of the invention, a boom joint is provided for coupling the mast to the boom of the dental whitening, imaging, or curing lamp to form an articulated support system. In various embodiments, the boom joint is adapted to maintain the boom in a fixed position and orientation with respect to the mast, subject to subsequent release. In a further aspect of various invention embodiments, the boom joint is adapted to permit both pitch and yaw motions of the boom with respect to the mast. According to still another embodiment of the invention, one or more of the boom and the mast are arcuate in form, and consequently an efficient use of space is possible within the confines of a dental examining room.

In one aspect, the lamp head having the light source and optical components may be in modular form. In another aspect, the control for the light source may be enclosed within a power pack. The power pack may be in modular form for easy installation and removal.

In one embodiment, the power pack may have a display panel for displaying the status of a dental process. In another embodiment, the pack may include a voice alert system for alerting the dental professional of the status of a dental process.

In one embodiment, at least portions of the whitening composition may be in a tray. The tray may be positioned in the patient's mouth using a reference device such as a lip retracting device.

In another embodiment of the invention, an illumination frame may be mounted to a lamp head. In one arrangement, the lamp head provides support for the illumination frame. In another arrangement, the lamp head provides power to the illumination frame. In yet another arrangement, the lamp head may be mounted to an adjustable floor stand that provides further adjustability for the dental illumination system. In still another arrangement, the illumination frame may be used in place of the lamp head and may be mounted directly to an adjustable floor stand. In one aspect, the illumination frame has a non-reflective surface in which the light sources are set. In one embodiment, the non-reflective surface is a coating on the illumination frame. In a second embodiment, the non-reflective surface is a layer of material adhered to the illumination frame. In a third embodiment, the illumination frame is made of a non-reflecting material. In a still further embodiment of the invention, the illumination frame may have a reflective surface.

In another embodiment of the invention, the dental illumination frame includes a plurality of light sources emitting light of substantially the same wavelength. In another embodiment of the invention, the dental illumination frame includes a plurality of light sources emitting light of different wavelengths.

In yet another embodiment of the invention, the dental illumination system has an arcuate illumination frame having tapered ends. The tapered ends result in less bulk in the illumination frame close to the patient's mouth. In an alternative arrangement, each of the tapered ends includes a slot wherein the slots are configured to mate with wings of a lip retracting device worn by a dental patient.

In still another embodiment of the invention, the dental illumination system has protruding light sources to enable the dental illumination system to provide more light from the light sources. In an alternative embodiment of the invention, the dental illumination system has light sources that are located flush with the illumination frame.

The present invention together with the above and other advantages may best be understood from the following detailed description of the embodiments of the invention illustrated in the drawings below.

BRIEF DESCRIPTION OF THE DRAWINGS

FIG. 10-1 shows, in perspective view, an illumination frame with tapered ends according to one embodiment of the invention;

FIG. 25 depicts a semi-schematic top plan view of the lip retracting device of FIG. 21a;

FIG. 32 shows an exploded view of the combination of a lip retracting device with the light guide and a lamp;

DETAILED DESCRIPTION OF THE INVENTION

Figure 1:
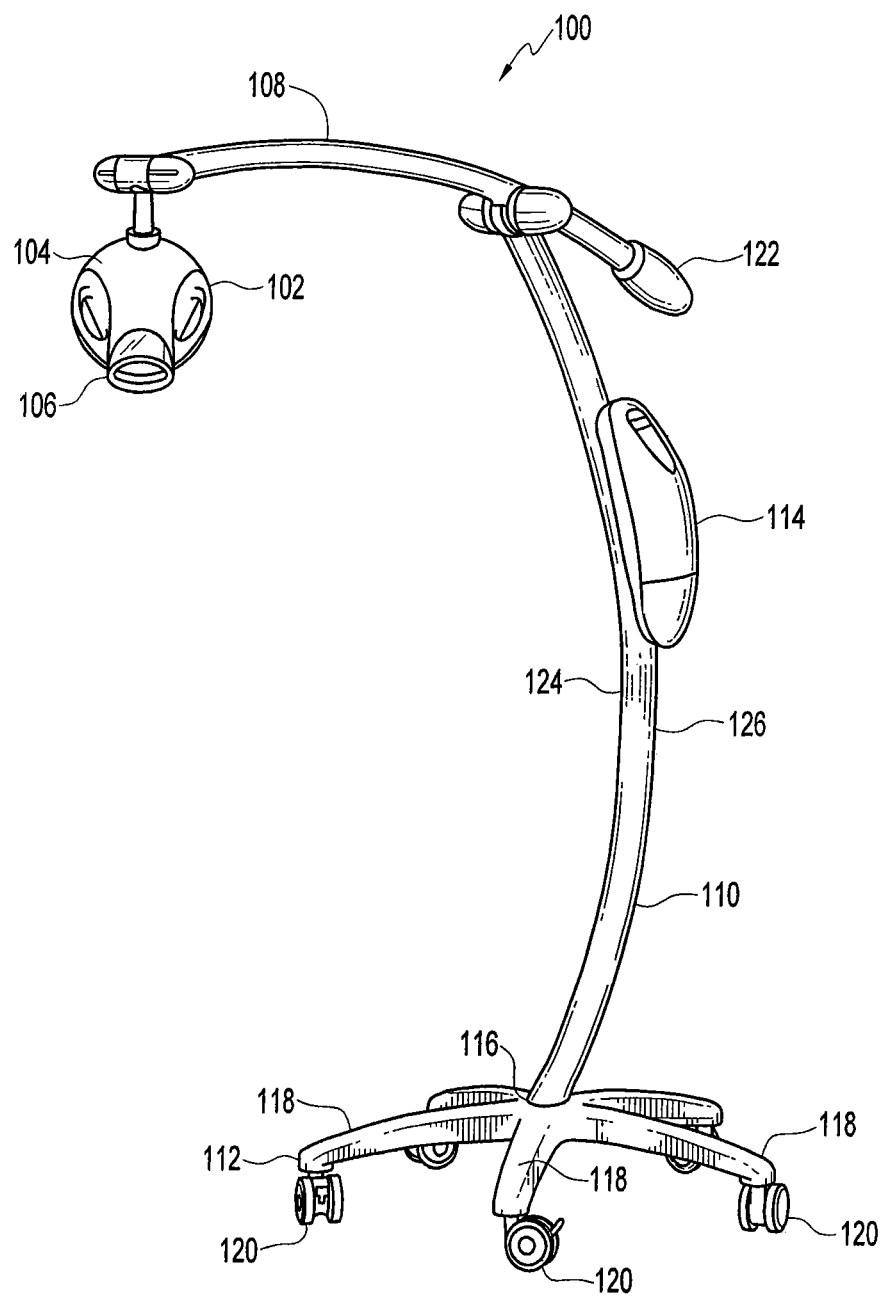
FIG. 1 shows, in perspective view, a dental whitening or curing lamp according to one embodiment of the invention.

The detailed description set forth below is intended as a description of the presently exemplified tooth bleaching and dental material curing methods and apparatus provided in accordance with aspects of the present invention and is not intended to represent the only forms in which the present invention may be prepared or utilized. The description sets forth the features and the steps for preparing and using the tooth bleaching and dental material curing methods and apparatus of the present invention. It is to be understood, however, that the same or equivalent functions and components incorporated in the tooth bleaching and dental curing methods and apparatus may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

The present invention is directed to an illumination system for dental whitening, imaging or curing. The lamp system activates a whitening substance or filling composite applied to a patient's teeth with light from a light source.

In dental whitening, cleaning and/or bleaching agents are applied to the teeth of a patient, for example. In tooth repair or restoration, composite filling materials are applied to surface and/or cavity in a tooth. The bleaching agents and/or composite materials are activated by the application of energy, such as, for example electromagnetic energy. In imaging, the light source produces an image of the tooth or teeth of a patient, either by direct imaging, for example, using x-rays, or by indirect imaging or trans-illumination.

For effective activation or imaging while reducing spurious heating of the teeth and surrounding tissues, electromagnetic energy of a particular wavelength, optimized for, for example, the activation of the particular chemicals in use, may be provided. For example, it is known to apply radiation in the visible and ultraviolet domains from a light source to the tooth or teeth of the dental patient to activate a whitening compound or filling composite.

Another way of enabling effective chemical activation of a dental whitening compound is to position a light source to fully illuminate the tooth surfaces being treated.

Since light intensity varies as the inverse cube of distance from a light source, it is desirable that the light source used be in reasonably close proximity to the tooth surfaces being treated. Also, because some of the light effective for chemical activation of a dental whitening or curing compound, or for imaging may also be deleterious to soft tissues, it is desirable to minimize the exposure of a patient's gums, tongue, facial skin and other soft tissues to the light source.

In view of these considerations, it is desirable that an illumination system be capable of rapid and reliable positioning of the light source in proximity to a patient's teeth or mouth.

To accomplish this, a reference device, such as a lip retracting device and a spacer, such as a light guide, include formations that may inter-engage as the reference device and spacer become apposed, in one aspect. In another aspect, the spacer and the lamp system include formations that removably inter-engage as the spacer and the lamp become apposed. The inter-engaging formations may serve to stabilize the spacer axially and against twisting.

The lamp system and a support system may include formations that inter-engage as the lamp system and the support system become apposed.

The word formation as used herein in relation to the reference device, spacer, the lamp system and a support system refers to the portion of the reference device, spacer and lamp system which is shaped to inter-fit with a corresponding part of an adjoining component. It includes portions of the above listed article which are shaped by molding, or portions which are formed separately and then subsequently assembled.

Suitable inter-engaging formations include tongues and grooves, posts and sockets, swingable hooks and sockets, resilient clips and sockets, tongue or wing-like members and slots, ball and cavity, ball and socket, some of which are more specifically exemplified in detail below.

The dental process includes protecting a patient's soft tissues which typically involves applying a soft overlay such as a sheet of rubber or foam over the patient's gums and other soft tissue. In a curing process, the overlay maybe applied to the unaffected teeth as well. The patient's soft tissues may alternatively be protected by, for example, opaque gauze pads or by non-UV light-curable, UV light-blocking masking chemicals. After the patient's soft tissues have been protected, a whitening composition or a filling composite is applied to the teeth or tooth. The composition is then activated with light from the lamp system. The light system of the present invention may be easily aligned to a subject and is ergonomically compatible for both right-handed and left-handed users. Further, the pieces of the light system are separable and modular, so that the light system is easy to assemble, disassemble, pack, ship or transport. In addition, individual pieces or modules may be sent in for repair or for updating.

The rubber material useful for the soft overlay may include either natural or synthetic rubber. Synthetic rubbers may be, for example, elastomeric materials and may include, but not limited to, various copolymers or block copolymers (Kratons®) available from Kraton Polymers such as styrene-butadiene rubber or styrene isoprene rubber, EPDM (ethylene propylene diene monomer) rubber, nitrile (acrylonitrile butadiene) rubber, latex rubber and the like. Foam materials may be closed cell foams or open cell foams, and may include, but is not limited to, a polyolefin foam such as a polyethylene foam, a polypropylene foam, and a polybutylene foam; a polystyrene foam; a polyurethane foam; any elastomeric foam made from any elastomeric or rubber material mentioned above; or any biodegradable or biocompostable polyesters such as a polylactic acid resin (comprising L-lactic acid and D-lactic acid) and polyglycolic acid (PGA); polyhydroxyvalerate/hydroxybutyrate resin (PHBV) (copolymer of 3-hydroxy butyric acid and 3-hydroxy pentanoic acid (3-hydroxy valeric acid) and polyhydroxyalkanoate (PHA) copolymers; and polyester/urethane resin.

FIG. 1 is a perspective view of a dental whitening, imaging or curing lamp system 100 according to one embodiment of the present invention. The lamp 100 includes a lamp head 102 having a lamp head housing 104 and a light guide 106. The lamp head 102 provides the light that, for example, activates a whitening substance or curing composite applied to a patient's teeth by directing the light through the light guide 106. This lamp system may be used in a dental office or a dental laboratory.

The lamp housing 104 and head 102 may be made of any polymeric material, for example, a polymer that can be molded or cast; or a metal or metallic alloy. Suitable polymers include polyethylene, polypropylene, polybutylene, polystyrene, polyester, acrylic polymers, polyvinylchloride, polyamide, or polyetherimide like ULTEM®; a polymeric alloy such as Xenoy® resin, which is a composite of polycarbonate and polybutyleneterephthalate or Lexan® plastic, which is a copolymer of polycarbonate and isophthalate terephthalate resorcinol resin (all available from GE Plastics), liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, (exemplified in U.S. Pat. Nos. 6,242,063, 6,274,242, 6,643,552 and 6,797,198, the contents of which are incorporated herein by reference), polyesterimide anhydrides with terminal anhydride group or lateral anhydrides (exemplified in U.S. Pat. No. 6,730,377, the content of which is incorporated herein by reference) or combinations thereof.

In addition, any polymeric composite such as engineering prepregs or composites, which are polymers filled with pigments, carbon particles, silica, glass fibers, conductive particles such as metal particles or conductive polymers, or mixtures thereof may also be used. For example, a blend of polycarbonate and ABS (Acrylonitrile Butadiene Styrene) may be used for the lamp housing and head.

Generally, polymeric materials or composites having high temperature resistance are suitable.

Suitable metal or metallic alloys may include stainless steel; aluminum; an alloy such as Ni/Ti alloy; any amorphous metals including those available from Liquid Metal, Inc. or similar ones, such as those described in U.S. Pat. No. 6,682,611, and U.S. Patent Application No. 2004/0121283, the entire contents of which are incorporated herein by reference.

A liquid crystal polymer or a cholesteric liquid crystal polymer, one that can reflect rather than transmit light energy, may be used, either as a coating or as the main ingredient of the housing 104 and/or lamp head 102, to minimize escape of light energy, as described, for example, in U.S. Pat. Nos. 4,293,435, 5,332,522, 6,043,861, 6,046,791, 6,573,963, and 6,836,314, the contents of which are incorporated herein by reference.

The lamp head 102 is attached to a first end of a boom 108. The lamp head 102 is positionable with respect to the boom 108 and has a wide range of motion with respect to the end of the boom 108. The boom 108 is supported by a mast 110. In the illustrated embodiment, the boom 108 is pivotally mounted to the mast 110 at a point on the boom 108 closer to a second end of the boom 108 than the lamp head housing 104.

The boom 108 is adjustably positionable with respect to the mast 110. The boom 108 has both a rotational and a tilt range of motion with respect to the mast 110. A counterweight 122 on the second end of the boom 108 provides a counterbalance for the lamp head 102.

The mast 110 is attached to the base 112. In the illustrated embodiment, the mast 110 is fixed with respect to the base 112. In the embodiment shown, base 112 is a rolling base having a plurality of arms 118 extending radially from a center 116 of the base 112 where the mast 110 is attached.

The boom 108, mast 110 and base 112 may be fashioned out of any polymer or metal, such as those mentioned above for use in the lamp housing 104. Here, since the boom 108, mast 110 and base 112 are less likely to be subjected to any potentially high temperature environment, the suitable materials need not be of high temperature resistance. On the other hand, structural integrity is a more desirable feature.

In the illustrated embodiment, a caster wheel 120 is coupled to a respective distal end of each of the plurality of arms with respect to the center 116 of the base 112. The caster wheel 120 is adapted to contact, and thus to be supported by, a surface, for example, a supporting floor. In one embodiment of the invention, at least one of the caster wheels 120 includes a braking mechanism that prevents the caster wheel from rolling when the braking mechanism is in a locked position. In another embodiment of the invention, a plurality of caster wheels 120 includes the braking mechanism. In a further embodiment, a plurality of caster wheels 120 includes individual respective braking mechanisms.

The rolling base 112 enables the entire lamp system 100 to be positionable with regard to a patient in a dental chair. The rolling base 112 shown here is merely exemplary. Other types of rolling bases are contemplated within the scope of the invention. In addition, the mast 110 in other embodiments of the invention may be axially rotatable with respect to the base 112. According to one embodiment of the invention the mast 110 is curved and the curve accordingly defines a concave side 124 and a convex side 126 of the mast 110.

In the embodiment illustrated, a power pack 114 is attached to the mast 110 on the convex side 126. The power pack 114 includes controls for the lamp system 100.

The housing of the power pack 114, the rolling base 112 and rollers 120 may also be made out of any polymer or metal providing structural integrity, such as the materials mentioned above for use in the lamp housing 104. Here, since the rolling base 112 and rollers 120 are also not subject to a potentially high temperature environment (unlike the power pack housing 114, the lamp housing 104 and the head 102), the suitable materials may not have the capability of high temperature resistance.

In operation, the lamp system 100 is positioned with respect to the patient in a dental chair (not shown). The location of the power pack 114 on the mast 110 enables the lamp system 100 to be operated whether the lamp system 100 is positioned to the right or to the left side of the patient. The curvature of the mast 110 enables the lamp system 100 to be positioned with respect to the patient such that the power pack 114 is located away from the patient making the lamp system 100 easier to operate.

Figure 1A:
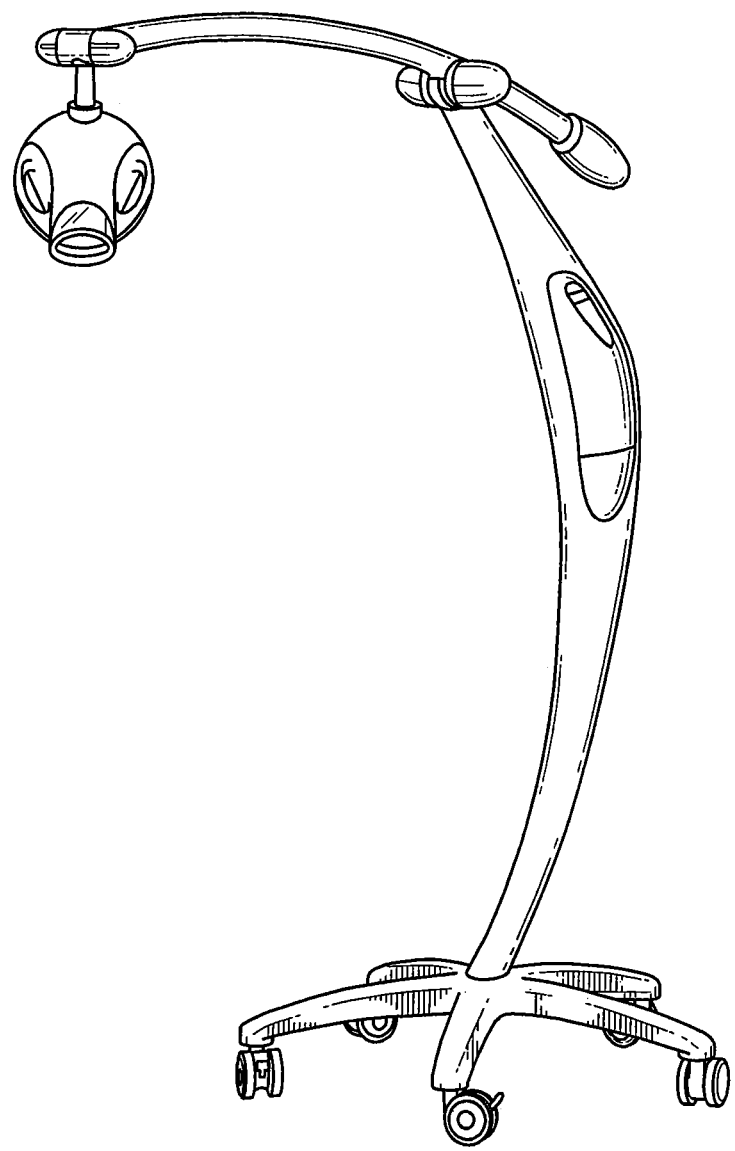
FIG. 1a shows, in perspective view, a dental whitening or curing lamp according to one embodiment of the invention.

In one embodiment, the mast 110 may have a uniform outer dimension along its length, as shown in FIG. 1. In another embodiment, the mast 110 may have a non-uniform outer dimension along its length, as shown in FIG. 1*a*. In FIG. 1*a*, the mid-section of the mast 110 is of a larger dimension than other parts of the mast. In one aspect, this mid-section may coincide with the mounting position of the power pack 114. In another aspect, the wider portion of the mast 110 may be flattened to accommodate a power pack 114. In a third aspect, the wider portion may be sunken or recessed to accommodate a power pack 114 so that the power pack 114 does not protrude far from the general profile of the mast 110.

In one embodiment of the invention, the boom 108 and mast 110 may be positioned such that their footprint does not exceed the footprint of the base 112. Specifically, when the boom 108 is rotated to a minimally vertical angle, whereby the lamp head is at its lowest elevation in proximity to the base, a projection of the lamp system on the floor falls entirely within the circumference of the base 112.

In another embodiment, the boom 108 and mast 110 may be positioned such that their footprint exceeds the footprint of the base 112 with the center of gravity of the dental lamp system falling within the base 112.

In an alternative embodiment of the invention, the outward-most surface of the counterweight 122 does not extend beyond the circumference of the base 112 in any angular position of the boom 108.

As shown in the embodiment of FIG. 1, the location of the power pack 114 on the mast 110 combined with the positionability of the lamp system 100 on either side of a patient enables both right-handed and left-handed lamp operators to operate the lamp system 100 equally comfortably and effectively.

Once the lamp system 100 is positioned with respect to the patient, the operator aligns the spacer, which is shown in FIG. 1 as a light guide 106, with the lamp system. The lamp head 102 may be set to a wide range of positions through the wide range of motion of both the boom 108 with respect to the mast 110 and the lamp head 102 with respect to the boom 108. The light guide 106 may be configured to mate with a lamp head 104, and a reference device, which may be a lip retracting device (not shown in FIG. 1 or 1*a*) worn by the patient, thereby providing a substantially precise alignment with the patient's mouth. Exemplary embodiments and materials are described in U.S. Application No. 60/604,577, "Lip Retractors", filed Aug. 25, 2004 and are described in more detailed below.

The light guide 106 may also be made of similar materials as discussed above for the lamp housing 104 and lamp head 102. Additionally, like the lamp housing 104 and the lamp head 102, a cholesteric liquid crystal polymer, one that can reflect rather than transmit light energy, may be used either as a coating or as the main ingredient of the light guide to minimize escape of light energy, as described, for example, above.

Figure 2:
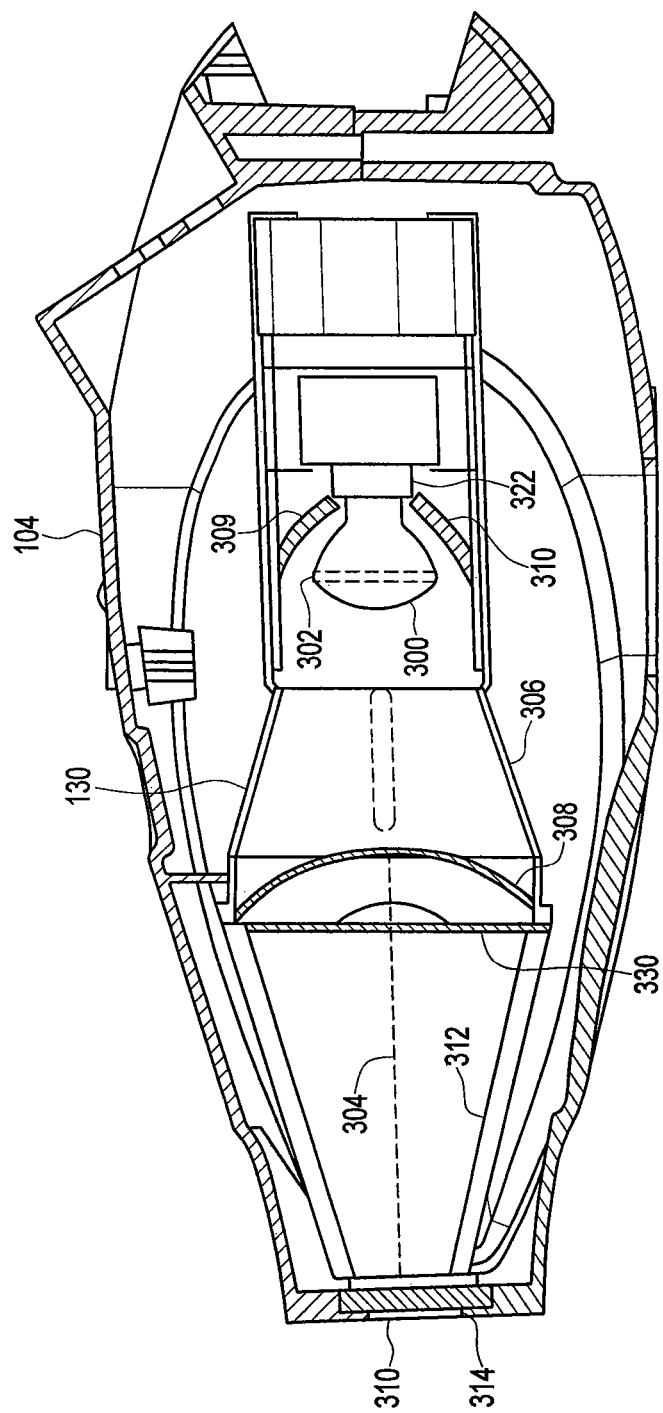
FIG. 2 shows, in cross section, various components of a whitening or curing lamp head, according to one embodiment of the invention.

FIG. 2 shows, in cross section, various components of the lamp head housing 104 and lamp subassembly 130 according to one embodiment of the invention. A light source 300 located inside the lamp head housing 104 includes a first reflector 302 integral to the light source 300. The first reflector 302 directs light from the light source 300 generally along a path 304 through an aperture 310 in the lamp head housing to a target (not shown) such as a whitening compound disposed on a tooth surface or a filling compound residing either on the surface or in the cavity of a tooth.

The light path 304 includes a second reflector 306 generally coaxial with the first reflector 302. The body of the second reflector 306 includes an upper tab 309 and a lower tab 310 which are depressed after assembly toward the light source base 322. The upper tab 309 and lower tab 310 provide additional protection to hold the light source 300 in place if the lamp head 102 is jarred or dropped. The second reflector 306 includes a reflective internal surface adapted to further direct light toward the aperture 310 to the target. The present embodiment of the lamp head housing 104 further includes an optical lens 308 disposed within the second reflector 306. According to this embodiment, the optical lens 308 includes at least one curved surface and is adapted to direct light from the light source 300 toward the aperture 310.

The light path 304 further includes an integrator 312 located in proximity to the second reflector 306 and generally coaxial with the first reflector 302. The integrator 312 serves to integrate the light to provide light of uniform intensity passing through the aperture 310. The light path 304 further includes a diffuser 330 disposed within the integrator 312. In addition, an optical filter 314 disposed coincident with the second aperture 310 serves to impede the passage of various wavelengths of light while allowing the passage of other wavelengths. For example, in one embodiment, the optical filter 314 may serve to prevent passage of most light characterized as in the infrared range from passing through the second aperture 310 to the target. In contrast, light in the ultraviolet and/or visible ranges are allowed to pass. Consequently, light suitable for activating a dental whitening compound is available outside of the aperture 310, while infrared light, which would otherwise unduly elevate the temperature of the target area, is excluded from the target area or is reduced to acceptable levels.

The light source of the embodiment described above may also include a gas-filled arc light such as a halogen source, semiconductor light emitting devices, light emitting chips such as a light-emitting diode (LED), a solid-state LED, an LED array or a fluorescent light source, all of which are merely exemplary. Other types of light generation devices, including lasers and X-ray sources are possible within the scope of the invention.

Figure 3:
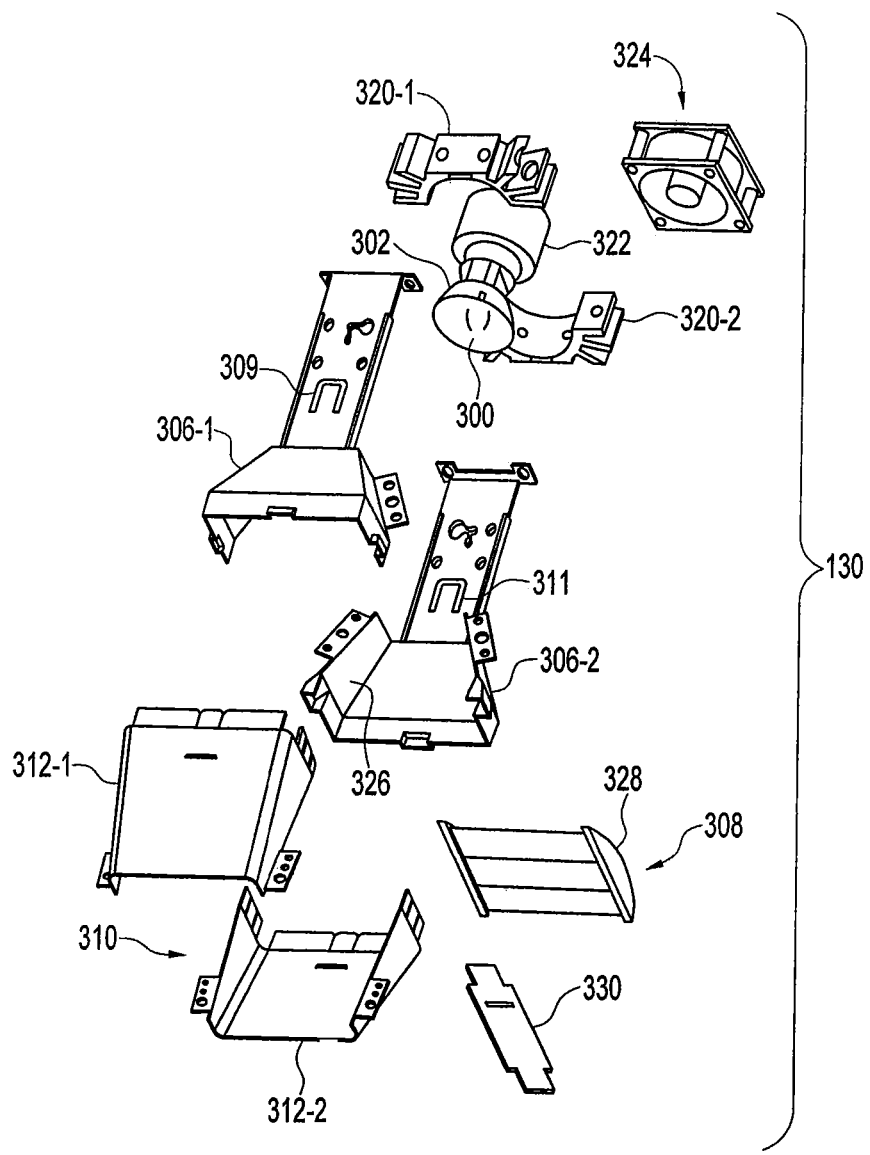
FIG. 3 shows, in assembly drawing format, several components of a dental whitening or curing lamp according to one embodiment of invention.

FIG. 3 is an exploded view of a lamp head according to one embodiment of the invention. In the illustrated embodiment, a light source 300 includes a first reflector 302. The lamp subassembly 130 has a heat sink 320-1, 320-2 to be coupled to the light source ballast/base 322. A fan 324 located in the lamp head housing 104 in proximity to the heat sink 320 and ballast/base 322 further acts to keep the source 300 and lamp subassembly 130 cool. The heat sink may be made of any material that has good thermal conductivity, including metal blocks of copper, aluminum or similar. In another embodiment, the cooling system includes heat pipes. In another embodiment, the cooling system includes phase change materials, some embodiments and material are exemplified as is described in U.S. application Ser. No. 11/173,274, entitled "Dental Light Devices Having an Improved Heat Sink" to be concurrently filed; and U.S. Provisional Application No. 60/585,224, entitled "Dental Light Devices With Phase Change Material Filled Heat Sink", filed on Jul. 2, 2004, the contents of which are incorporated herein by reference.

Heat sinks having a phase change material may more efficiently remove or divert heat from a light source or sources with a given weight of heat sink material when compared to a heat sink made of a solid block of thermally conductive material such as metal. Such a heat sink may even efficiently remove or divert heat from a curing light device when a reduced weight of the material is used. Using a phase change material enclosed inside a hollow thermally conductive material such as a metal heat sink instead of a conventional solid metal heat sink can decrease the weight of the curing light and increase the time the heat sink takes to reach the "shut off" temperature, as it is called in the dental curing light industry. The period prior to reaching the shut off temperature is called the "run time". Increasing the "run time", i.e., the time that the light can remain on, increases the time when a dentist can perform the curing or whitening procedure.

In one embodiment, a rechargeable dental curing light including at least one phase change material is disclosed. In another embodiment, a dental whitening light including at least one phase change material is disclosed. The heat sink includes a block of thermally conductive material, such as metal, having a bore or void space which is at least partially filled with a phase change material.

The heat sink may be constructed by hollowing out a thermally conductive material, such as metal, and at least partially filling the void with at least one phase change material prior to capping it to secure the phase change material inside, such that the at least one phase change material is substantially contained or surrounded by a thermally conductive material such as metal normally used in the construction of a conventional heat sink.

Alternatively, the heat sink may be cast or machined from a thermally conductive material, such as metal, to create walls surrounding a bore or void. The bore or void is partially filled with at least one phase change material prior to capping it to secure the material inside.

In one embodiment, the inventive heat sink may be used by itself. In another embodiment, it may be used in addition to a fan, in conjunction with a conventional metal block heat sink or combinations thereof.

The inventive heat sink may be installed into the dental curing light, imaging or whitening light source in the same manner a conventional metal block heat sink is installed, such as by attaching it to the heat generating source, i.e., the light source, which may include any of the ones mentioned above or combinations thereof, or by attaching it to another heat sink.

Suitable phase change material may include organic materials, inorganic materials and combinations thereof. These materials can undergo substantially reversible phase changes, and can typically go through a large, if not an infinite number of cycles without losing their effectiveness. Organic phase change materials include paraffin waxes, 2,2-dimethyl-n-docosane ($C_{24}H_{50}$), trimyristin, (($C_{13}H_{27}COO)_3C_3H_3$), and 1,3-methyl pentacosane ($C_{26}H_{54}$). Inorganic materials such as hydrated salts including sodium hydrogen phosphate dodecahydrate ($Na_2HPO_4.12H_2O$), sodium sulfate decahydrate ($Na_2SO_4.10H_2O$), ferric chloride hexahydrate ($FeCl_3.6H_2O$), and TH29 (a hydrated salt having a melting temperature of 29° C., available from TEAP Energy of Wangara, Australia) or metallic alloys, such as Ostalloy 117 or UM47 (available from Umicore Electro-Optic Materials) are also contemplated. Exemplary materials are solids at ambient temperature, having melting points between about 30° C. and about 50° C., more for example, between about 35° C. and about 45° C. Also, the exemplary materials have a high specific heat, for example, at least about 1.7, more for example, at least about 1.9, when they are in the state at ambient temperature. In addition, the phase change materials may, for example, have a specific heat of at least about 1.5, more for example, at least about 1.6, when they are in the state at the elevated temperatures.

The phase change material may also have a high latent heat of fusion for storing significant amounts of heat energy. This latent heat of fusion may be, for example, at least about 30 kJ/kg, more for example, at least about 200 kJ/kg.

Thermal conductivity of the materials is a factor in determining the rate of heat transfer from the thermally conductive casing to the phase change material and vice versa. The thermal conductivity of the phase change material may be, for example, at least about 0.5 W/m° C. in the state at ambient temperature and at least about 0.45 W/m° C. in the state at elevated temperature.

In general, the phase change material may be contained inside a thermally conductive material, such as a metal casing. The casing defines a bore, which may be of any shape, but is for example, generally of a cylindrical or rectangular shape. The metal casing or wall of the bore acts to contain the phase change material, and to also aid in conducting heat to and away from the phase change material. The thinner the wall, the more phase change material can be present in a given size of the heat sink, and the less it contributes to the weight of, for example, the curing light. However, the thinner the wall, the less efficient the heat sink maybe in conducting heat away from the phase change material and the longer it will take to return the phase change material to ambient temperature and its original state, so that it may function as a heat sink again. For example, the wall thickness ranges from about 1 mm to about 2.5 mm, more for example, from about 1 mm to about 1.5 mm.

The casing may also be constructed to have a large surface area. A structure having fins or other features that serve to increase the surface area for heat conduction or convection is desirable, thus a spherical structure, though useful, is not the optimal choice. Such fins or other surface area increasing features may also be incorporated into the bore to increase the contact area between the thermally conductive casing and the phase change material, thus permitting faster more efficient transfer of heat between the thermally conductive casing and the phase change material.

The thermally conductive casing can also provide a good thermal contact for heat transfer from the light source. This may be accomplished with a smooth, thermally conductive surface with a high area of contact. Also, thermal coupling may be achieved with thermally conductive interface materials such as thermal epoxy. Interface materials that are electrically insulating are also useful in isolating the light source from the heat sink in an electrical sense without losing thermal conductivity.

The lamp subassembly 130 further includes a second reflector 306-1, 306-2 located substantially coaxial with the first reflector 302. The body of the second reflector 306 includes two tabs 309, 311. The tab 309 in the second reflector upper portion 306-1 is bent downwards toward the bulb base 322 which provide additional protection to hold the light source 300 in place if the lamp head 102 is jarred or dropped. In an alternative embodiment, the tab 311 in the second reflector lower portion 306-1 is bent upwards toward the bulb base 322 to provide further protection. Typically, only one of the tabs is bent in order to facilitate disassembly of the lamp head 102. The second reflector 306 includes a reflective internal surface 326 adapted to further direct light toward the aperture 310 to the target. The reflective internal surface 326 is, for example, a highly polished metal. Other embodiments of the second reflector 306 include anodized aluminum, and reflectors formed by vapor deposition of dielectric layers onto metallic layers, for example, a metallic layer on an anodized surface as the base reflection layer, followed by deposition of a low refractive index and then a high refractive index dielectric layer, such as those available from Alanod, Ltd. of the United Kingdom; a liquid crystal polymer plastic, one that can reflect rather than transmit light energy, may be used, either as a surface coating layer or as a main ingredient of the reflector, as described above, or other materials with similar properties.

Typically, a liquid crystal plastic compound is selected for a particular application based on one or more factors including, for example, refractive indices, processability, low absorption in the wavelength of interest, ease of manufacture, ease of solvent removal, physical and chemical properties (for example, flexibility, tensile strength, solvent resistance, scratch resistance, and phase transition temperature), and ease of purification.

Suitable liquid crystal polymers include those suitable for the lamp head housing mentioned above. Suitable polymers include a chiral polyester, polycarbonate, polyamide, polymethacrylate, polyacrylate, polysiloxane, or polyesterimide backbone that includes mesogenic groups optionally separated by rigid or flexible comonomers. Other suitable liquid crystal polymers have a polymer backbone (for example, a polyacrylate, polymethacrylate, polysiloxane, polyolefin, or polymalonate backbone) with chiral mesogenic side-chain groups. The side-chain groups are optionally separated from the backbone by a spacer, such as an alkylene or alkylene oxide spacer, to provide flexibility.

Typically, to form a liquid crystal layer, a liquid crystal composition is coated onto a surface. The liquid crystal composition includes at least one chiral compound (e.g., liquid crystal plastic compound) or chiral monomer (liquid crystal monomer) that can be used (e.g., polymerized or crosslinked) to form a liquid crystal polymer plastic. The liquid crystal composition can also include at least one nematic liquid crystal compound or nematic liquid crystal monomer that can be used to form a nematic liquid crystal polymer. The nematic liquid crystal compound(s) or nematic liquid crystal monomer(s) can be used to modify the pitch of the liquid crystal composition. The liquid crystal composition can also include one or more processing additives, such as, for example, curing agents, crosslinkers, or ultraviolet, infrared, antiozonant, antioxidant, or visible light-absorbing dyes.

Liquid crystal compositions can also be formed using two or more different types of any of the following: liquid crystal plastics, liquid crystal monomers, nematic liquid crystals, nematic liquid crystal monomers, or combinations thereof. The particular ratio(s) by weight of materials in the liquid crystal composition will typically determine, at least in part, the pitch of the liquid crystal layer.

The liquid crystal composition also typically includes a solvent. The term "solvent", as used herein, also refers to dispersants and combinations of two or more solvents and dispersants. In some instances, one or more of the liquid crystal compounds, liquid crystal monomers, or processing additives also acts as a solvent. The solvent can be substantially eliminated from the coating composition by, for example, drying the composition to evaporate the solvent or reacting a portion of the solvent (e.g., reacting a solvating liquid crystal monomer to form a liquid crystal polymer).

After coating, the liquid crystal composition is converted into a liquid crystal layer. This conversion can be accomplished by a variety of techniques including evaporation of a solvent; crosslinking the liquid crystal compound(s) or liquid crystal monomer(s); or curing (e.g., polymerizing) the liquid crystal monomer(s) using, for example, heat, radiation (e.g., actinic radiation), light (e.g., ultraviolet, visible, or infrared light), an electron beam, or a combination of these or like techniques.

In one embodiment, an optical lens 308 is disposed within the second reflector 306. According to this embodiment, the optical lens 308 includes at least one curved surface and is adapted to direct light towards a target. The lamp subassembly 130 further includes the integrator 312-1, 312-2 and a diffusing element 330 which act together to provide uniform light directed at a target (not shown).

The optical path, or the interior of the lamp housing 104 of the lamp or illumination system may further include at least one absorber/emitter having at least a portion that is substantially transparent to the incident light, and at least one portion capable of absorbing the incident light and emitting light of a longer wavelength. In one embodiment, at least one wavelength transformer may be configured to capture substantially all the emitted light and transforming only a portion of the captured light into a longer wavelength. In another embodiment, at least one wavelength transformer may be configured to capture at least a portion of the light emitted by the light source and transforming all captured light into a longer wavelength. The wavelength transformer may also be present as a component of the light source 300, at least a portion or component of the reflectors 302, 306, or the interior of the lamp housing 104, as shown in FIG. 2.

The wavelength transformer may also be adapted to capture any lower wavelengths outside of the usable range of the intended purpose and transforming it to a usable wavelength, thus making use of the available output power and minimizing extraneous heat generation.

Figure 4:
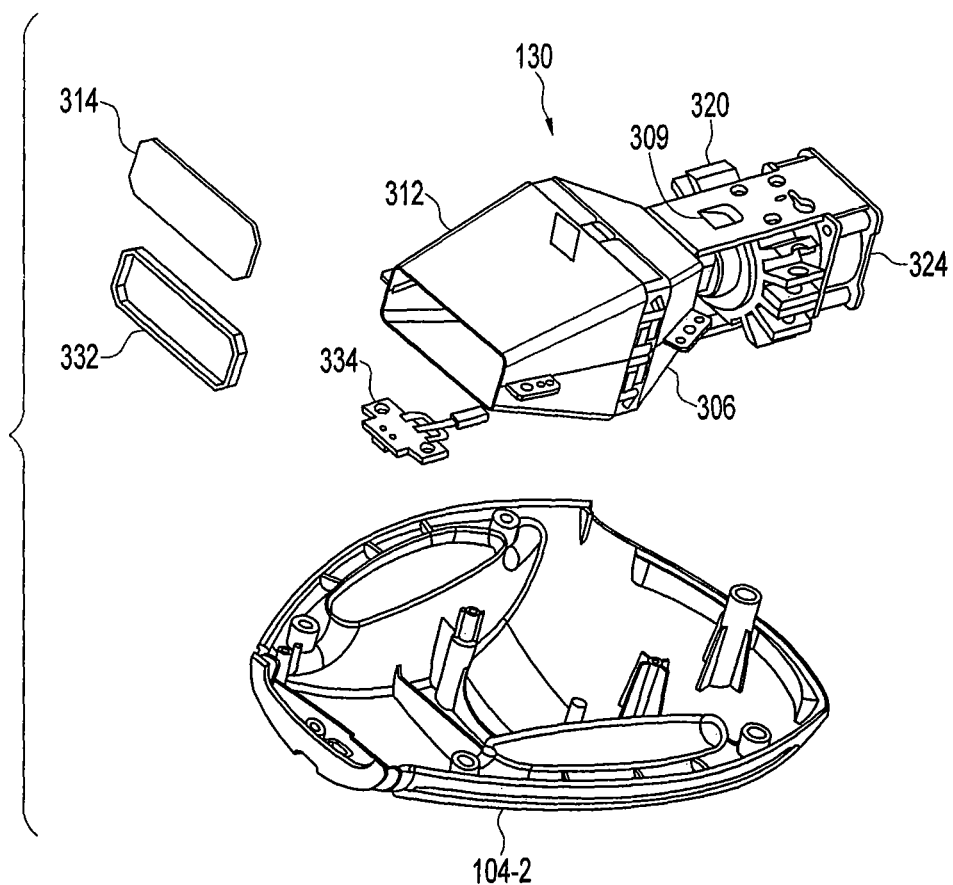
FIG. 4 shows, in perspective view, components of a lamp head according to one embodiment of the invention.

FIG. 4 is an exploded perspective view of the bottom half of the lamp head housing 104 and the lamp subassembly 130 of FIGS. 2 and 3. The lamp subassembly 130 is assembled in this view and includes the cooling components (the heat sink 320 and fan 324), and the second reflector 306 and integrator 312. The upper tab 309 in the second reflector 306 is shown in the depressed mode in order to protect the light source as described above. Further, the optical filter 314 is shown along with an elastomeric mounting 332 for the optical filter 314. When assembled into the lamp subassembly 130, the optical filter 314 is coupled to the integrator 312 with the elastomeric mounting 332. Also shown in this FIG. is the electromechanical connector 334 that couples the lamp system to the electronics in the light guide. This portion of the lamp system 100 will be described in greater detail below.

Figure 4A:
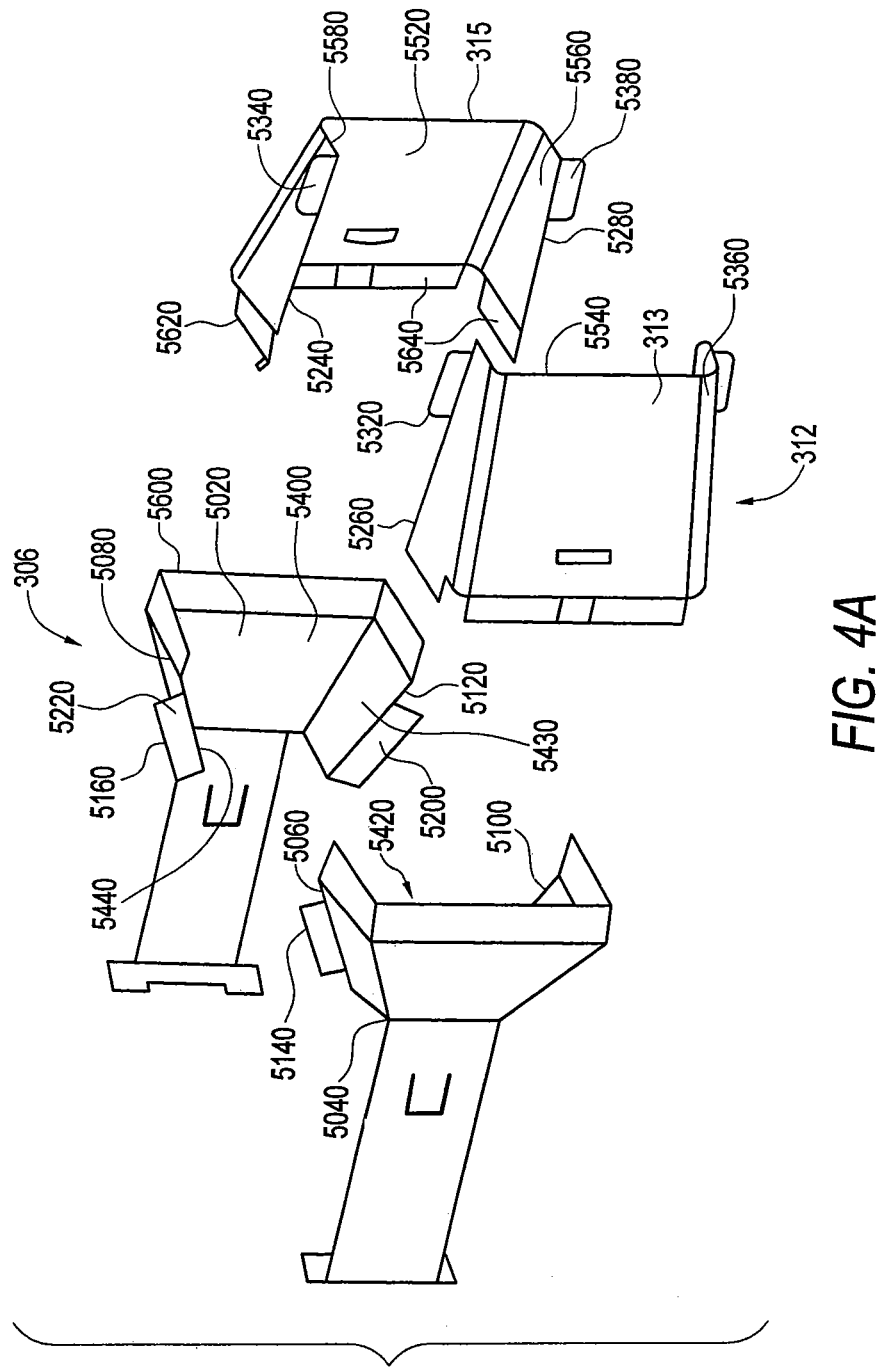
FIG. 4a shows, a reflector and integrator assembly according to one embodiment of the invention.

FIG. 4a shows the assembly of the second reflector 306 and integrator 312 in additional detail. According to the illustrated embodiment, the second reflector 306 and integrator 312 form a substantially rectangular pipe or box. As shown, the reflector includes first 5020 and second 5040 reflective internal surfaces.

In the illustrated embodiment, the lower portion 305 and upper portion 307 of the second reflector 306 are adapted to fit to one another at corresponding edges 5060, 5080 and 5100, 5120. According to one embodiment of the invention, the lower portion 305 and upper portion 307 each include respective tabs 5140, 5160, 5180 (not shown) and 5200 to facilitate this connection. Each tab 5140, 5160, 5180, 5200 includes a respective surface (e.g., 5220) adapted to be mutually supported against the respective tab of the opposing member.

Like the second reflector 306, the integrator 312 is formed, in the illustrated embodiment, of two portions 313 and 315. Each of these portions includes respective mutually supporting edges 5240, 5260, 5280 and 5300, and surfaces 5320, 5340, 5360 and 5380.

The reflector portions 5100, 5120 each have a substantially trapezoidal internal surface region 5400, 5420. In addition, the joining of the mutually supporting edges forms additional substantially trapezoidal surface regions 5430, 5440.

In like fashion, the integrator portions 313, 315 are joined during assembly. According to one embodiment of the invention, this results in substantially rectangular surface regions 5520, 5540 and substantially trapezoidal surface regions 5560, 5580. In another embodiment of the invention, surface regions 5520 and 5540 are substantially trapezoidal.

According to a further aspect of the invention, the reflector portions 5100, 5120 and integrator portions 313, 315 are joined at respective edges 5600, 5620 to form the above-mentioned substantially rectangular pipe or box. According to one embodiment of the invention, one or both of the reflector 306 and integrator 312 includes projecting tabs 5640 at their mutually supporting edges. These tabs 5640 may be integral to the respective assembly portions, or may be assembled thereto. According to one embodiment of the invention, the tabs 5640 serve to interleave with each other, or with the opposite member, and thus to more effectively couple the reflector 306 to the integrator 312.

Because the light wavelengths most effective for imaging, for chemical activation of a dental whitening compound or other dental composition, may be deleterious to soft tissues, it is desirable to minimize the exposure of a patients gums, tongue, facial skin and other soft tissues to the subject illumination. Therefore, properly controlling the light path and focus of the applied illumination is important.

In addition, in order to produce predictable, and therefore optimizable results, it is important that the intensity of the illumination received at a target composition be substantially spatially and uniform. Also, the above-noted desirability of limiting light exposure to the target composition motivates a further aspect of the invention in relation to fixturing of the light source and target area, also noted above.

Figure 5:
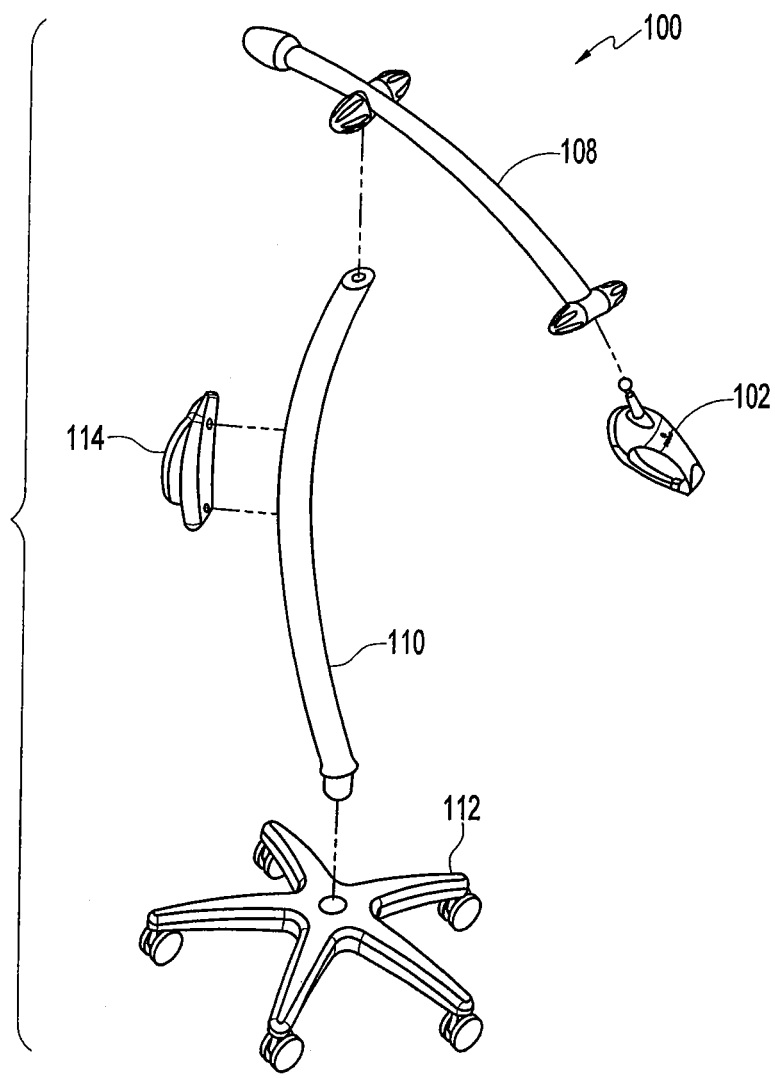
FIG. 5 shows, in perspective view, a lamp head and boom according to one embodiment of the invention, and illustrates the removability of the lamp head from the boom according to one aspect of the illustrated embodiment.

FIG. 5 is an exploded perspective view of the lamp system according to one invention embodiment. According to various embodiments of the invention, the lamp head 102 is removably attached to the boom 108. The boom 108 is removably attached to the mast 110. The mast 110 is removably attached to the base 112. The power pack 114 is removably attached to the mast 110. The attachment mechanisms for each piece will be described in greater detail below. The ability to separate each of the lamp system main elements, that is, the lamp head 102, the boom 108, the mast 110, the base 112 and the power pack 114, from lamp system 100 provides advantages in shipping, transportation and maintenance.

The separated and/or modular lamp pieces are easier to pack in a shipping crate than the lamp system 100 assembled. Further, those pieces that require greater protection such as the lamp head 102 may be packed in a more protective container than the other pieces thereby protecting the more delicate pieces of the lamp system 100 while minimizing shipping costs.

The separated lamp system pieces are also easier to transport than a fully assembled lamp, as, for example, by a salesperson making customer visits. Further, the ability to separate the lamp system pieces enables individual pieces to be shipped to a repair center for repair or for upgrade. For example, the lamp head 102 may be shipped to a repair center for light source replacement.

Figure 6:
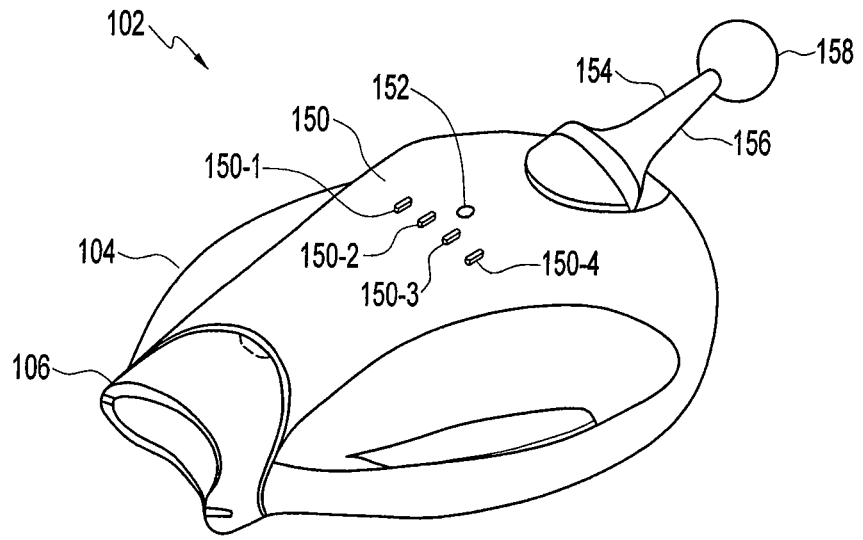
FIG. 6 shows, in perspective view, a lamp head according to one embodiment of the invention.

FIG. 6 is a perspective view of a lamp head 102 according to one embodiment of the invention. The lamp head 102 includes the lamp head housing 104 and the light guide 106. The lamp head housing 104 produces and directs light through the light guide 106. In the present embodiment, the lamp head housing 104 produces light with a light source such as a bulb or any of the light sources previously described. The light guide 106 may serve as an interface between the lamp system 100 and the patient having a dental treatment, such as whitening, to be described in greater detail below with regard to FIG. 16.

The lamp head housing 104 further includes two types of lighted indicators 150, 152. The first type 150 indicates the portion of the dental whitening process that has been completed. In this embodiment, there are four such lighted indicators 150-1, 150-2, 150-3, and 150-4. Each of these indicators 150-1, 150-2, 150-3, and 150-4 shows that a portion of the whitening process has been completed. For example, for an hour-long whitening process, a first 150-1 of these indicators is lit after fifteen minutes. After thirty minutes a second indicator 150-2 is lit, and so on until the hour is passed at which point all indicators 150-1, 150-2, 150-3, and 150-4 are lit. In an alternative embodiment of the invention, the lamp head housing 104 includes an indicator system in which a lighted indicator blinks at selected intervals to indicate the percentage of the whitening process that has been completed. In another alternative embodiment of the invention, a display mounted in the lamp head housing 104, such as a liquid crystal display, indicates the status of the whitening process.

The second type of lighted indicator is a single indicator 152 that indicates a need for a new light source in the lamp head housing 104, hereafter referred to as the light source replacement indicator 152. The mechanism by which the light source replacement indicator 152 is activated will be described below with respect to FIG. 35.

In the illustrated embodiment of the lamp head housing 104, the lighted indicators 150, 152 are lit with LEDs. In a first alternative embodiment, the LEDs protrude through the surface of the lamp head housing 104. In a second alternative embodiment, the top surface of the lamp head housing 104 may be sealed and/or smooth and the LEDs are positioned in recesses in the undersurface of the lamp head housing 104. The material of the lamp head housing 104 in the vicinity of the LED may be transparent or translucent. This embodiment has the advantage that the surface of the lamp head housing 104 is easier to clean and also does not collect debris as would occur if there were protrusions in the lamp head housing surface. In a third alternative embodiment, the lamp head housing surface has markings positioned over the lighted indicators of the second embodiment.

In another embodiment of the invention, a control system having a built-in voice alert system for alerting a dental professional of the time, or stage, in a dental procedure may be included. The control system may also include a headphone or other private listening device, for example, so that only the dental professional will receive the voice alert. In one aspect, the private listening device may be a wireless listening device such as a wireless radio channeling device or an infrared channeling device.

In one embodiment, a dental light system includes a built-in electronic voice alerting system to alert the dental professional of the completion of a dental procedure.

In one aspect, the electronic voice alerting system may utilize an electronic voice generating circuit technology, similar to the technology used in electronic devices such as toys, cell phones, automobiles and other consumer electronics, but with novel message content that is directed to dental applications.

In still another embodiment, a dental illumination system includes an audible electronic voice alert system having a novel approach to tracking time during the above mentioned dental procedures and other similar dental procedures. This audible electronic voice alert system uses an electronic device with prerecorded time interval statements stored in the device.

According to one embodiment, the alert system, in addition to having the lighted indicators mentioned above, is also adapted to play a recorded voice that is generated when an electronic timer circuit is programmed to play the appropriate electronic voice count alert through an audio speaker in the device. In one aspect, the message played may include time intervals, and may be programmed and in some embodiments, re-programmed.

In a further embodiment, a dental lamp system having an electronic timer device is controlled by a microprocessor with an internal clock. The microprocessor receives a signal so as to know when a lamp is first turned on. At predefined intervals of, for example, five seconds, the electronic voice chip sends a recorded audio signal to a speaker to announce elapsed and/or remaining time to the user. In one embodiment of the invention, the speaker is disposed within the light source. This process may be programmed to continue and announce the ten second intervals when the voice chip releases a different recorded audio signal of "ten seconds". Various time increments and corresponding audio signals can be programmed or selected according to the requirements of a particular dental procedure.

In yet a further embodiment of the invention, a dental lamp system includes a prerecorded audio stream that may be configured to play a unique alert message at the end of a procedure. The pre-recorded audio signal can include a message such as "procedure complete", "end of a first cycle" when used in chairside whitening procedures, or similar phrase. Additionally, the system may be configured to give instruction to the dental professional at certain times during the procedure. Exemplary messages may include prerecorded audio streams announcing, "the procedure is almost complete", "please plan for the next step in the whitening process", and "whitening lamp warm up cycle complete." Numerous and various such voice alerts are possible and are intended to be within the scope of this invention.

In a yet still further embodiment, the invention, includes a dental instrument having a voice alert system in any of the above embodiments coupled to an electrical control device. The electrical control device may include a microprocessor and a switch such as an electromechanical switch or a solid state switch. In various embodiments, the electrical control device is adapted to both alert the dental professional of the end of the procedure, and to also turn off the light output, when the predetermined time period has expired. This may further improve the efficiency and accuracy of a dental procedure and free the dental professional to take care of other matters within earshot of the voice alert system rather than having to hover around the patient or be close at hand to turn off the lamp. In one aspect, the alert system may be equipped with a patient to dentist and/or dental practitioner call device.

The present embodiment of the lamp head 102 further includes a formation such as a pivot mount 154. This pivot mount is also used if an illumination frame 105, such as that shown in FIG. 10 described below, is used in place of the lamp head 102. The pivot mount 154 is used to removably attach the lamp head 102 to the boom 108. The pivot mount 154 includes a shaft 156 and a ball swivel 158. The shaft 156 of the pivot mount 154 is attached at one end to the back of the lamp head housing 104. The ball swivel 158 is attached to the other end of the shaft 156. The ball swivel 158 is inserted into a spring-loaded ball cup on the boom 108 which will be described in greater detail below with regard to FIG. 5. The pivot mount 154 enables the lamp head 102 to be swiveled around the end of the boom 108 resulting in a high degree of freedom of movement and therefore also improved ability to position the lamp head 102 with respect to the patient.

Figure 7:
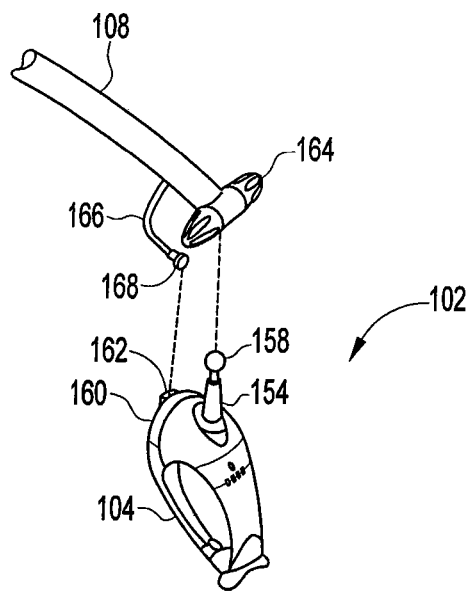
FIG. 7 shows a mechanical and electrical coupling between a lamp head and boom according to one embodiment of the invention.

FIG. 7 is a perspective view of the lamp head 102 and a portion of the boom 108, further illustrating the removability of the lamp head 102 from the boom 108. The lamp head 102 is shown separated from the end of the boom 108, and includes the lamp head housing 104 and the pivot mount 154. At the rear of the lamp head housing 104 is a grill 160 having an electrical connector 162.

The boom 108 has a lamp connector assembly 164. The lamp connector assembly 164 receives the ball swivel 158 of the pivot mount thereby removably attaching the lamp head 102 to the boom 108. As described above, this connection between the lamp head 102 and the boom 108 allows a high degree of freedom of movement of the lamp head 102 with respect to the boom 108. Further, the boom 108 is a substantially hollow tube and may contain I/O cables 166. The I/O cables 166 include an electrical plug 168 that is received by the electrical connector 162 in the lamp head housing 104 thereby removably attaching the lamp head 102 to the boom electronically. The I/O cables 166 provide power to the lamp head 102 and also carry data and control signals to and from the power pack 114.

Figure 7A:
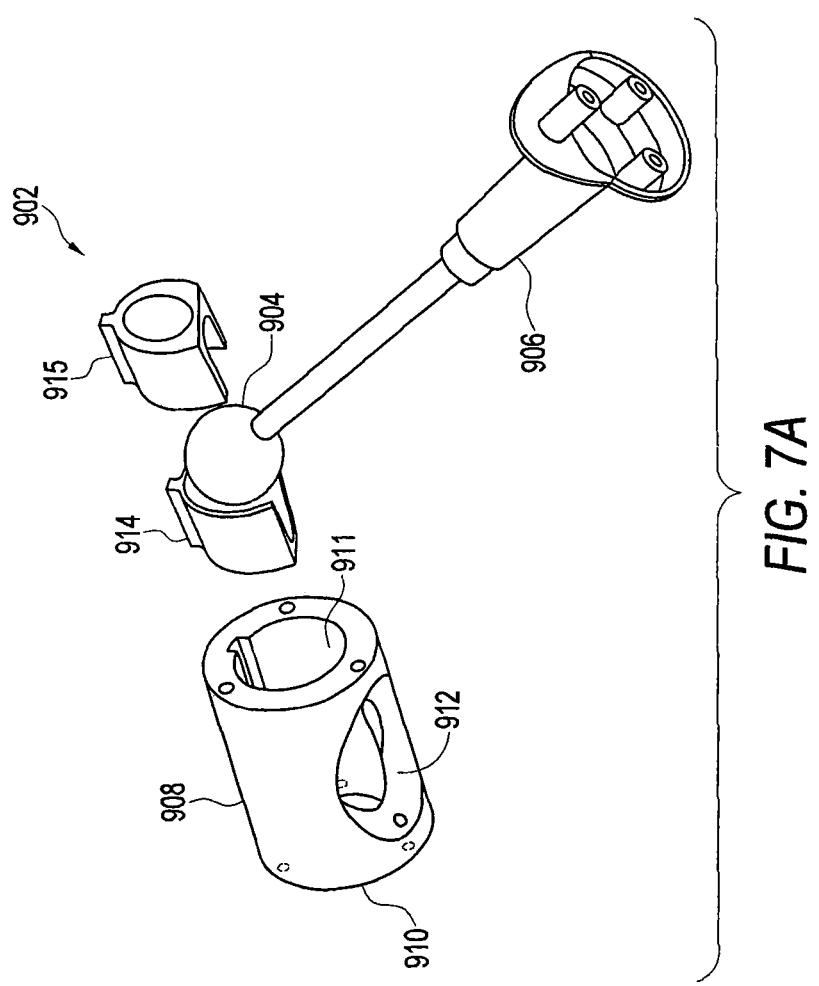
FIG. 7a shows an embodiment of a ball and socket joint.

FIG. 7a shows, in perspective view, components of a ball and socket joint according to one embodiment of the invention. The ball and socket joint (also referred to as a ball joint) 902 includes a head tube 908 having a first opening 910 and a second opening 911 at opposite ends of the head tube 908. A third opening 912 is present in the side of the head tube 908. The ball joint 902 further includes a first ball cup 914 and a second ball cup 915 to be received into the first and second openings 910, 911, respectively. A pivot mount 906 that holds the dental whitening lamp head (not shown) connects to the ball joint 902 by a ball swivel 904. The first and second ball cups 914, 915 are configured to receive the ball swivel 904 through the third opening 912 in the head tube 908. The ball joint 902 will be described in more detail below.

Figure 8:
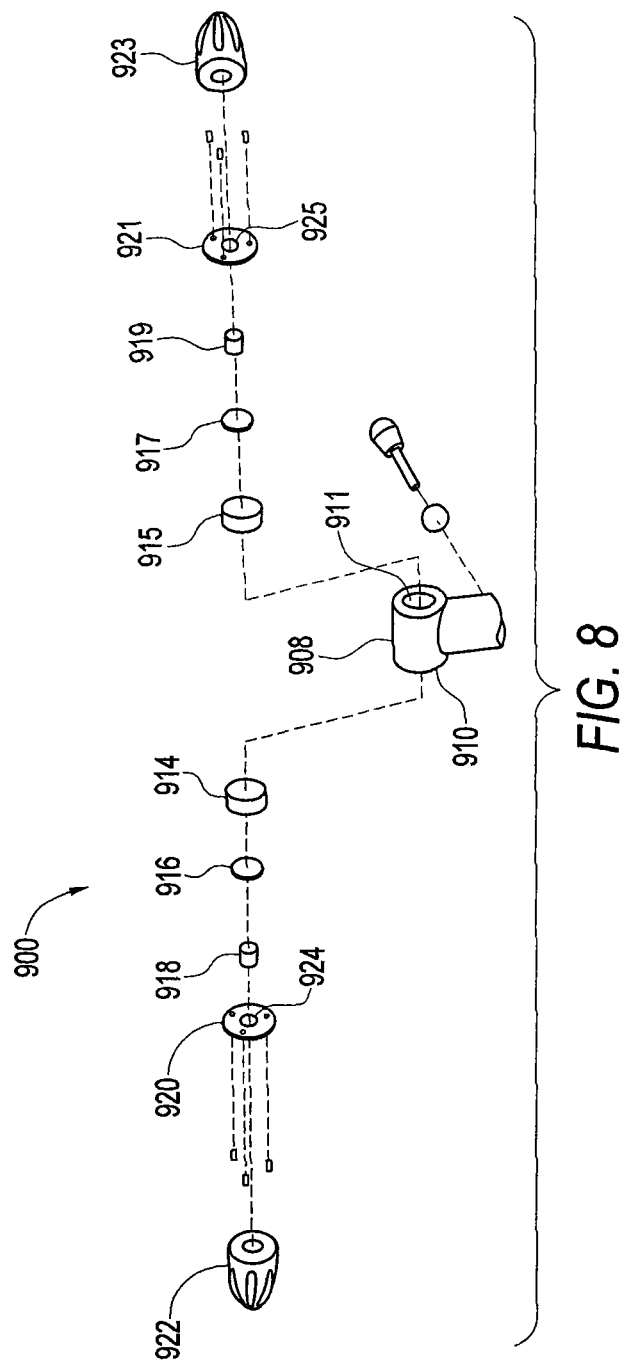
FIG. 8 shows, in assembly drawing format, a lamp head joint according to one embodiment of the invention.

FIG. 8 is an exploded view of the lamp connector assembly 900 enabling separable attachment between the lamp head 102 (not shown here) and the boom 103. The head tube 908 is attached to the end of the boom 103. The lamp connector assembly 900 is a socket joint including a ball joint 902 that receives the ball swivel 904 of pivot mount 906 on the lamp head as shown below.

The forward assembly 900 of the present embodiment includes a first and a second ball cup 914, 915, a first and a second spacer 916, 917, a first and a second spring 918, 919, a first and a second nut plate 920, 921 and a first and a second ball joint knob 922, 923. Each ball cup 914, 915 has a curved surface so that when the ball cups 914, 915 are mated at the curved surfaces a substantially spherically-shaped space configured to receive the ball swivel 904 is formed.

To form the ball joint, the ball cups 914, 915 are inserted into the head tube 908 so that the spherically-shaped space aligns with the third opening 912 of the head tube 908. The spacers 916, 917 are inserted into openings 910 and 911 respectively and positioned on either side of the mated ball cups 914, 915. The first and second springs 918, 919 are placed against the first and second spacers 916, 917 respectively.

The nut plates 920, 921 are attached on opposing ends of the head tube 908 over the first and second openings 910, 911. The nut plates 920, 921 each may have a central opening 918, 919 that may be threaded.

According to one embodiment of the invention, each of the knobs 922, 923 may include an ultrasonically welded stud having an externally threaded distal end. The screws of the knobs 922, 923 are screwed through the central openings of the nut plates 920, 921 and press against the springs 918, 919, spacers 916, 917, and ball cups 914, 915 to press the ball cups 914, 915 against the ball swivel 904. When the knobs 922, 923 are tightened down, the received ball swivel 904 may not move inside the mated ball cups 914, 915. When the knobs 922, 923 are loosened, the received ball swivel 904 may move inside the mated ball cups 914, 915.

A first alternative embodiment of the ball socket involves relying on spring strength rather than pressure from a screw to put pressure against the ball cups 914, 915. Further, the springs 918, 919 shown here are coil springs. Alternatives to coil springs include, for example, spring washers, and other mechanisms for applying linear force, as known to those of skill in the art.

Figure 8A:
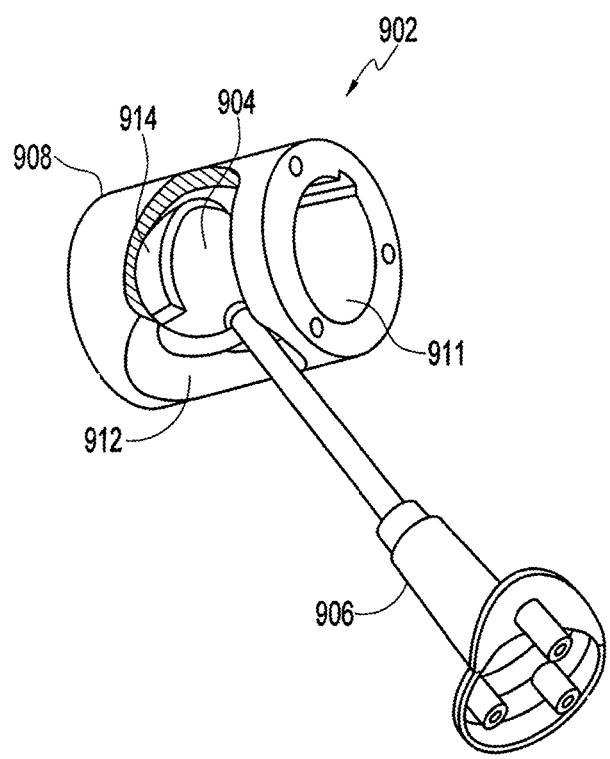
FIG. 8a shows, in sectional perspective view, components of a ball joint.

FIG. 8a shows, in sectional perspective view, components of a ball joint 902 shown with a cutaway view of the head tube 908 according to one embodiment of the invention. The first ball cup 914 is in place inside the head tube 908. The ball swivel 904 of the pivot mount 906 is shown inserted through the third opening 912 of the head tube 908.

One of skill in the art will appreciate that a ball joint, such as that illustrated, for example, in above FIGS. 8 and 8a, is merely exemplary of the various formations or coupling features which may be used to couple a dental apparatus or device to an end of the boom 903. For example in an alternative embodiment a flexible member, such as a gooseneck member, is disposed between the payload apparatus and the anterior end of the boom. The support structure of invention may include any flexible coupling device appropriate to a particular application and payload apparatus.

Figure 9:
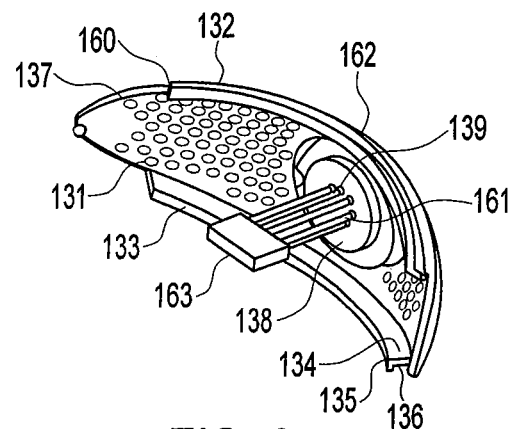
FIG. 9 shows, in perspective view, a grill and an electrical connector of a lamp head according to one embodiment of the invention.

FIG. 9 shows, in perspective view, a grill 160 for a lamp head housing according to one embodiment of the invention. In the illustrated embodiment, the grill includes a plurality of perforations 131 between inner and outer surfaces thereof. The perforations 131 are adapted to permit the passage of ambient air between an interior region and an exterior region of the lamp head housing, and thus allow for cooling and ventilation of the housing. In one embodiment, the perforations include a plurality of substantially circular holes. In other embodiments, the grill may include square holes, rectangular holes or slots, louvers, or another appropriate perforated barrier such as, for example, a woven wire screen or appropriate textile material.

The grill of the illustrated embodiment includes two flanges adapted to retain the grill in a substantially fixed position at an aperture of the lamp head housing. In the embodiment shown, the flanges include an upper flange 132 and a lower flange 133. Each flange has a respective first lateral 134 and second elevated 135 portions disposed in angled relation to one another.

The angled relation between lateral 134 and elevated 135 flange portions includes, in various embodiments, a 90° angle or other angle suited to a particular application. In addition, the flange of a particular embodiment includes a barb or latching profile or feature.

As would be understood by one of skill in the art, the elevated portions 135 include respective surfaces 136 adapted to contact respective inwardly facing regions of the lamp head housing so as to prevent displacement of the grill 160 when in use. Although the illustrated embodiment includes flanges that contiguously span a substantial portion of a width of the grill alternative embodiments include a plurality of narrower flanges spaced about a perimeter 137 of the grill.

It will be appreciated that, in various embodiments, the flanges may be supplemented or replaced by alternative coupling features such as snaps or fasteners. According to particular embodiments, such snaps or fasteners include one or more rivets, including pop-rivets, machine screws, self tapping screws, ball and socket pins, roll pins and cotter pins. In other embodiments, the grill is fixed in place by application of a chemical adhesive such as, for example, epoxy, silicone adhesive, contact cement, or cyanoacrylate based adhesive. In still other embodiments of the invention, the grill is retained in position by an elastomeric gasket and/or a magnetic coupler.

According to the illustrated embodiment, the grill also includes an electrical connector 162. The electrical connector has a reinforced region 138. In the illustrated embodiment, the reinforced region 138 is a removable member that is adapted to be assembled to the balance of the grill. In another embodiment of the invention, the reinforced region is integrally formed as a portion of the grill.

In one embodiment, the reinforced region 138 supports a plurality of individual electrical connector pins 139. In various embodiments the individual electrical connector pins include crimp-on connector pins such as, for example Molex™ connector pins. In another embodiment of the invention, the individual connector pins are adapted to be soldered to respective conductors, or integrally formed with those respective conductors.

In one embodiment of the invention, one or more of the individual connector pins is a female receptacle. In another embodiment of the invention, one or more of the individual connector pins is a male plug. One of skill in the art will appreciate that a wide variety of alternative integrated and individual connectors are possible, including connectors not available at the time of conception, and that these various connectors fall within the scope of the invention.

According to one embodiment of the invention, the individual connector pins are adapted to be inserted into preformed bores within the reinforced region 138. In another embodiment of the invention, the reinforced region is adapted to be formed, as for example by injection molding, with the individual connector pins 139 molded in situ.

In the illustrated embodiment, each connector is coupled to a respective conductor 161 so as to form respective mechanical and electrical connections to the conductor 161. According to one aspect of the invention, as illustrated, the respective conductors are mutually coupled to a second electrical connector 163 that is adapted to be disposed within the lamp housing. The second electrical connector includes a plurality of electrical contacts for connection to, for example, an internal circuit board of the lamp head.

Figure 10:
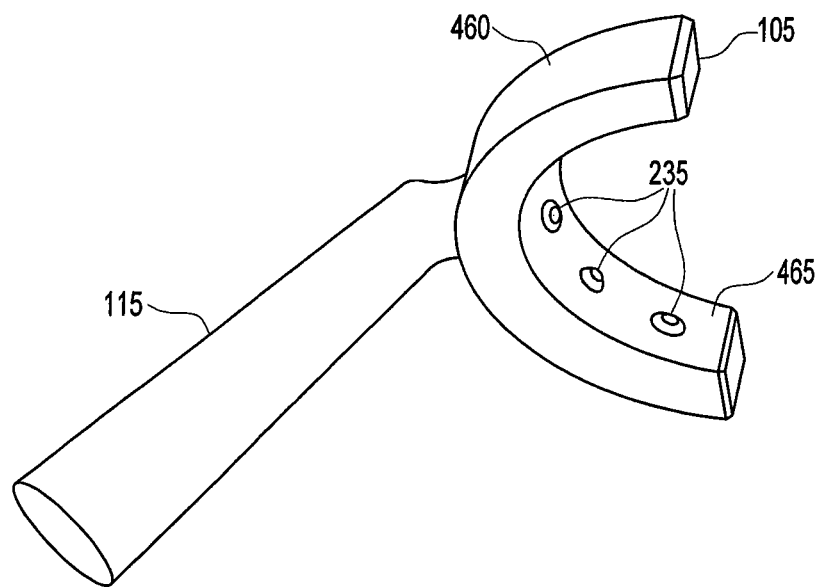
FIG. 10 shows, in perspective view, an illumination frame according to one embodiment of the invention.
Figure 11:
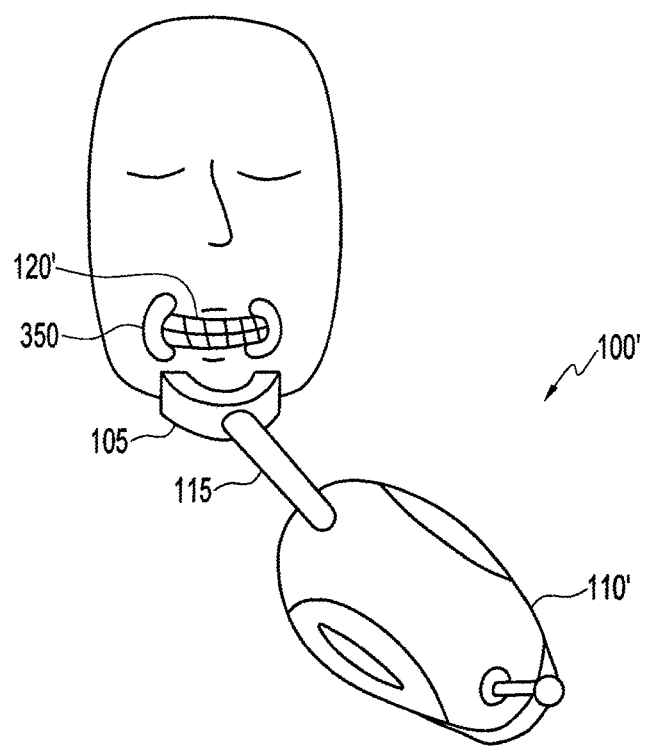
FIG. 11 shows, in perspective view, a dental whitening or curing lamp according to one embodiment of the invention.
Figure 11A:
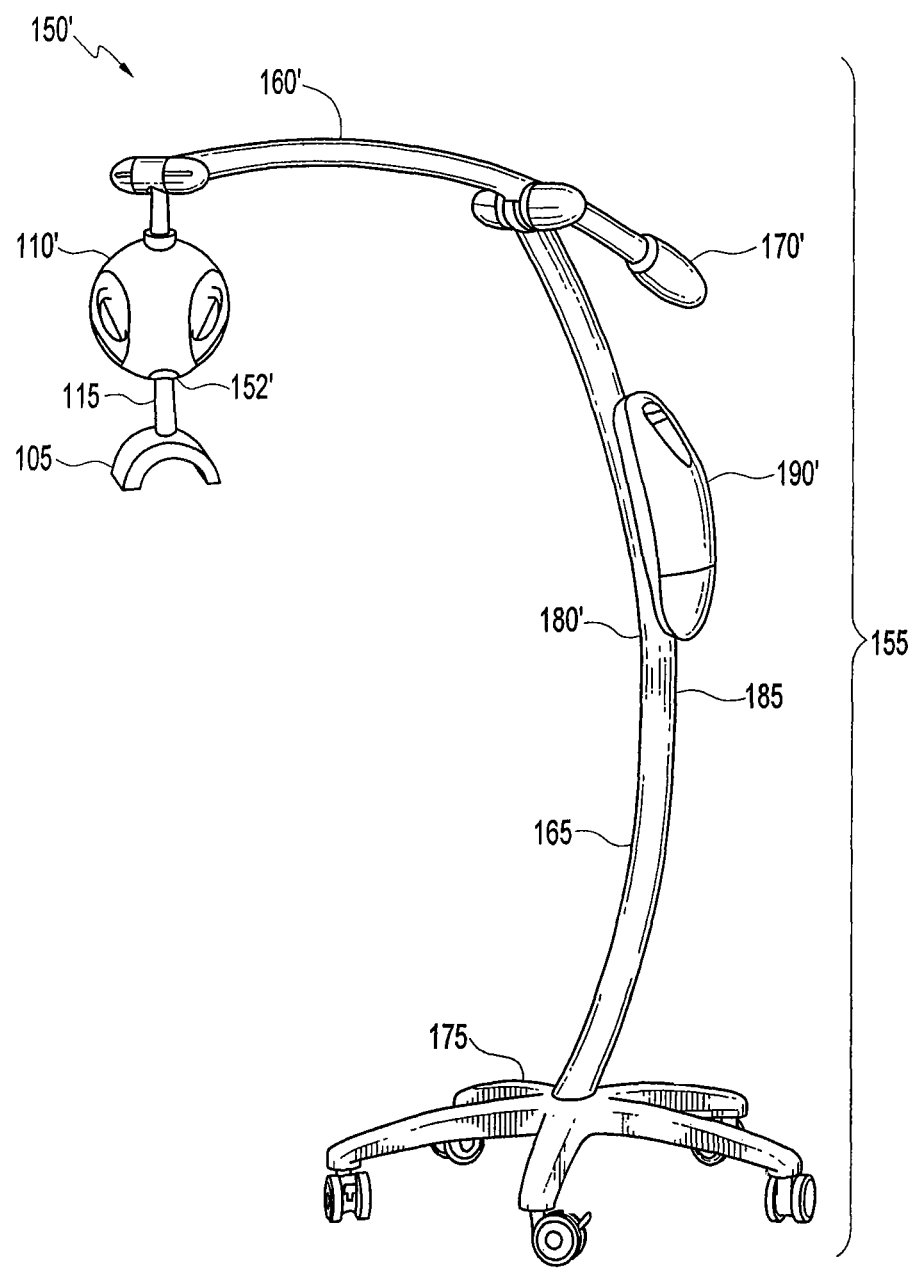
FIG. 11a shows, in perspective view, an illumination system according to one embodiment of the invention.

Multiple light sources, as shown in FIG. 10, may be used in place of the above lamp head housing as a self-contained structure, for example, an illumination frame, 105, in one embodiment. As shown in FIG. 11a, the lamp head provides support for the illumination system in one arrangement. In another arrangement, the lamp head provides power to the illumination frame 105. In yet another arrangement, the lamp head is mounted to an adjustable floor stand that provides further adjustability for the dental illumination system, as shown in FIG. 11a. In a further aspect, the illumination frame may be in addition to the lamp head housing, as shown in FIG. 11. In another embodiment of the invention, the illumination frame may be mounted to a lamp head, as is also shown in FIG. 11. The dental illumination system 100' includes an illumination frame 105 connected to a lamp head 110' by a tube 115. The illumination frame 105 provides light to activate a whitening substance or curing composite applied to a patient's teeth 120. The patient typically wears a reference device, such as a lip retracting device 350. The illumination frame 105 and lamp head 110' together generate and direct light toward the patient's teeth 120' for a whitening or a curing process. In one alternative embodiment, the illumination frame 105 and tube 115 may be adjustable with respect to the lamp head 110'. In another alternative embodiment, the tube 115 is flexible and may be adjusted to various positions. In another embodiment, the illumination frame 110' is flexible.

In the illumination system with multiple light sources, the light sources may be collectively powered or individually powered. If individually powered, each of the individual light sources may be turned on or off separately, as desired. This is especially useful for a curing or imaging process, where only one or two teeth may be undergoing treatment or being examined.

Multiple light sources may be arranged in a geometric arrangement. In one embodiment, they may be arranged in an arcuate form and may, for example, conform to the jaw of a patient, as shown in FIG. 10. The illumination frame 105 has a front 465 and a back 460. The front 465 is concave and the back 460 is convex. The tube 115 is attached to the back 230 of the illumination frame 105. The tube 115 provides support for the illumination frame 105 and also acts as a conduit for wiring for the illumination frame 105. A plurality of light sources 235 is arranged along the front 465 of the illumination frame 105. The light sources may be any light source as described above. These light sources are merely exemplary and are not limited to those listed. The light sources 235 generate and direct light toward the patient's teeth (as shown in FIG. 11) for a whitening, imaging or a curing process. In a first embodiment, the light sources 235 emit light having substantially the same light spectrum. In a second embodiment, the light sources 235 emit light having different spectra. In one aspect, the light sources are approximately equidistant from the various teeth toward which the light sources are directed. In another aspect, the light sources 235 may protrude from the surface of the front 460 of the illumination frame 105. In a further aspect, the light sources 235 may be disposed substantially flush with the surface of the front 460 of the illumination frame 105.

FIG. 11a is a perspective view of an illumination system 150' according to one embodiment. The frame 105 is attached by the tube 115 to the lamp head 110' which is attached to an adjustable floor stand 155. In one aspect, the tube 115 is attached to the lamp head 110' by a pivotal joint 152', e.g., a ball joint. In a first arrangement, the lamp head 110 provides power to the illumination frame 105 so that the illumination frame 105 can generate light to activate a whitening substance or a curing composite applied to a patient's teeth. In a second arrangement, the illumination frame 105 and lamp head 110' provides light for whitening, curing or imaging by generating light at the lamp head 110' and directing it through the illumination frame 105. In this embodiment, light is provided to the illumination frame 105 through fiber optics running through the tube 115.

Figure 11B:
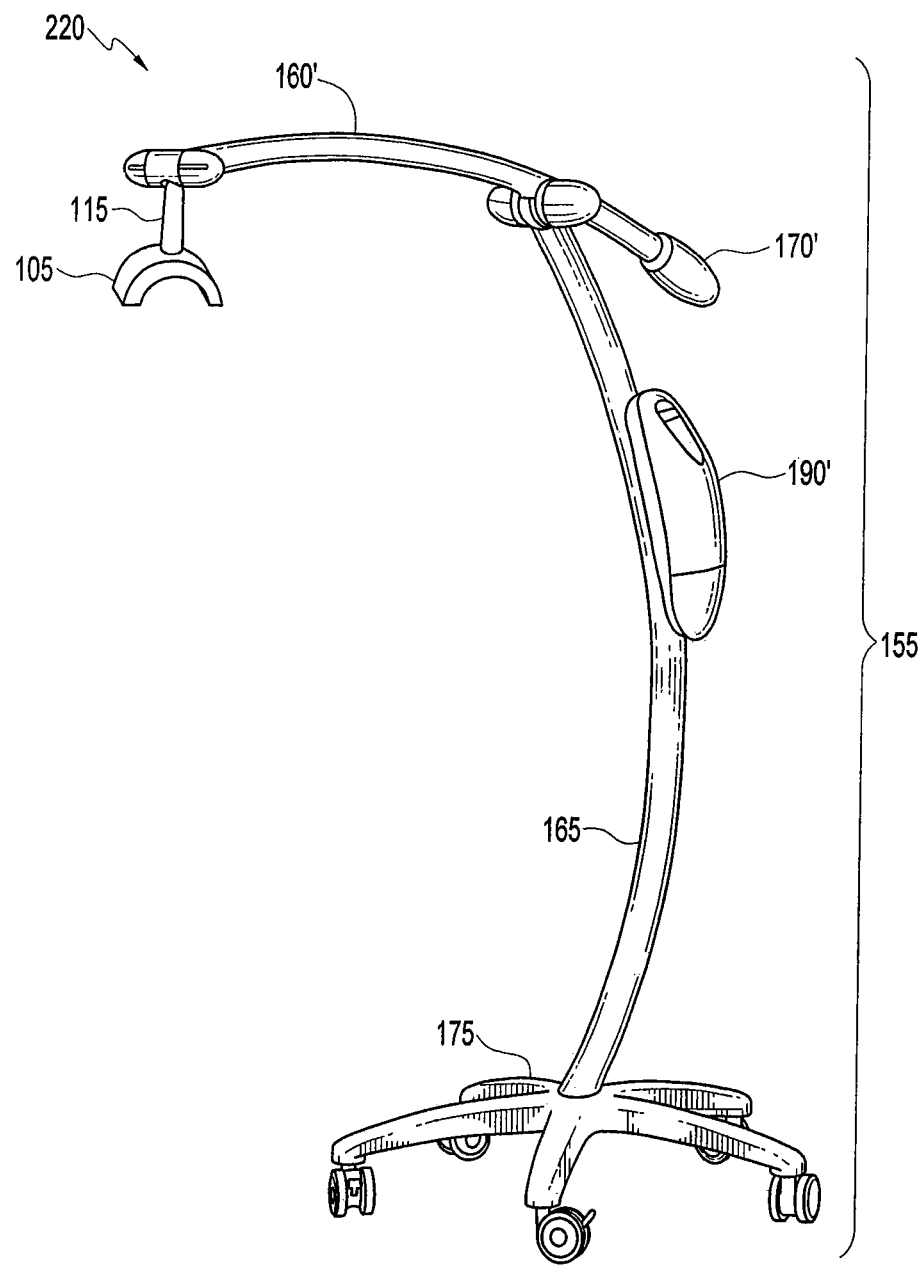
FIG. 11b shows, in perspective view, an alternative illumination system according to one embodiment of invention.

The illumination frame 105 may be similarly attached to the mast, as described above. An exemplary embodiment is shown in FIG. 11b, a perspective view of an illumination system 220 according to an embodiment of the present invention. The illumination frame 105 is attached by the tube 115 to the adjustable floor stand 155 directly rather than through a lamp head 110' as seen in FIG. 11a. In this embodiment, the control pack 190' is also a power pack. This embodiment has the adjustability of the system shown in FIG. 11a but has less weight due to the absence of the lamp head 110'.

The illumination frame 105 has a first end 450 and a second end 455, which may be tapered, as shown in FIG. 10-1, to reduce the bulk of the side of the illumination frame 105 at the patient's mouth.

Figure 10A:
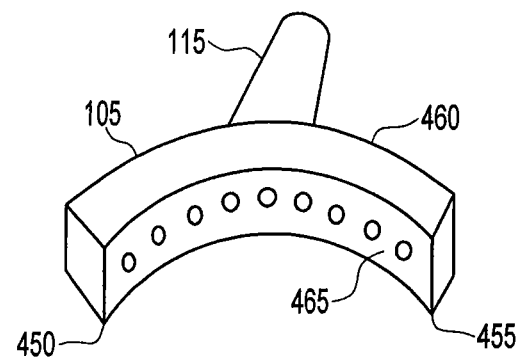
FIG. 10a shows, in perspective view, an illumination frame according to one aspect of the illustrated embodiment.

In one embodiment, the illumination frame 105 has a plurality of light sources 235 that are substantially evenly spaced across the surface of the front of the illumination frame 465, as exemplified in FIG. 10a. Other embodiments of the invention have different arrangements of light sources 235 across the front 465. For example, instead of being evenly spaced, the light sources may be staggered. The present invention is not limited to the number and arrangement of light sources 235 shown here.

Figure 10B:
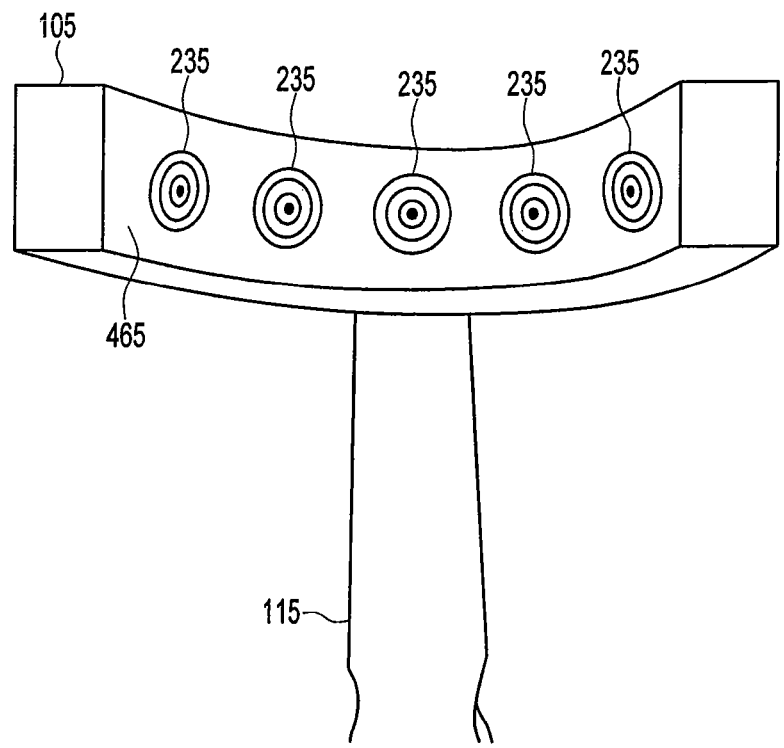
FIG. 10b shows, in perspective view, an illumination frame having a non-reflective surface according to one embodiment of the invention.

In FIG. 10b, the illumination frame 105 has a front 465 and a back 460. A tube 115 is connected to the back 460 and a plurality of light sources 235 are arranged along the front 225 of the illumination frame 105. In the embodiment shown, the surface 240 of the front 225 of the illumination frame 105 is non-reflective. In a first embodiment, the surface 240 is a non-reflective coating. In a second embodiment, the surface 240 is a layer of material such as a non-reflective plastic or rubber.

Figure 10C:
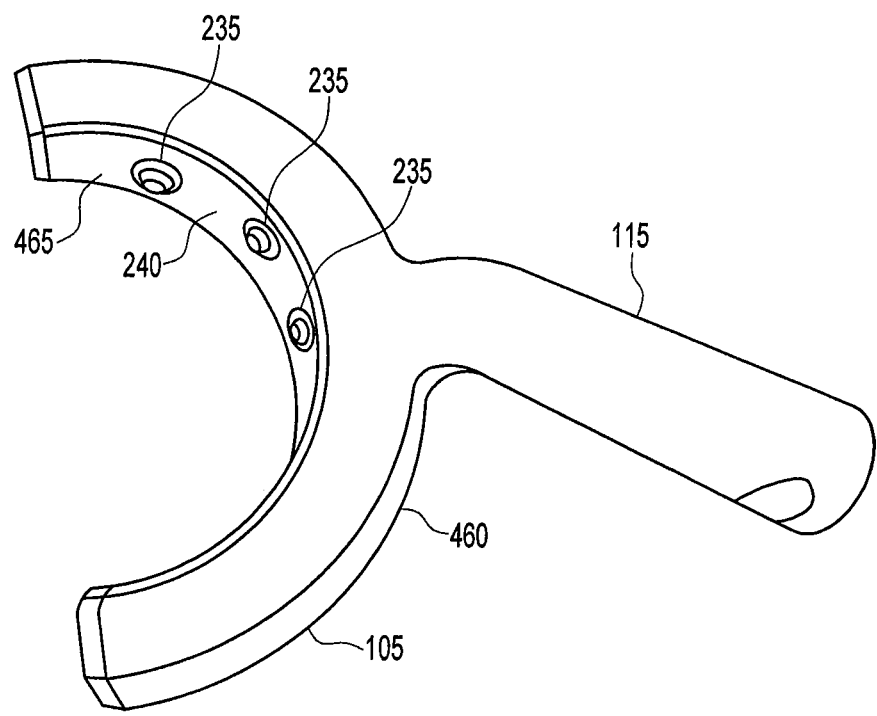
FIG. 10c shows, in perspective view, an illumination frame with an electrical connector according to one embodiment of the invention.

FIG. 10c is a rear perspective view of an illumination frame according to one embodiment of the invention. The illumination frame 105 also has a front 225 and a back 460 with a tube 115 attached to the back 460. The tube 115 provides support for the illumination frame 105 and also carries electrical wiring for the light sources (not shown). The wiring (not shown) is connected to an electrical connector 255 located at the inside 250 of the tube 115.

Figure 10D:
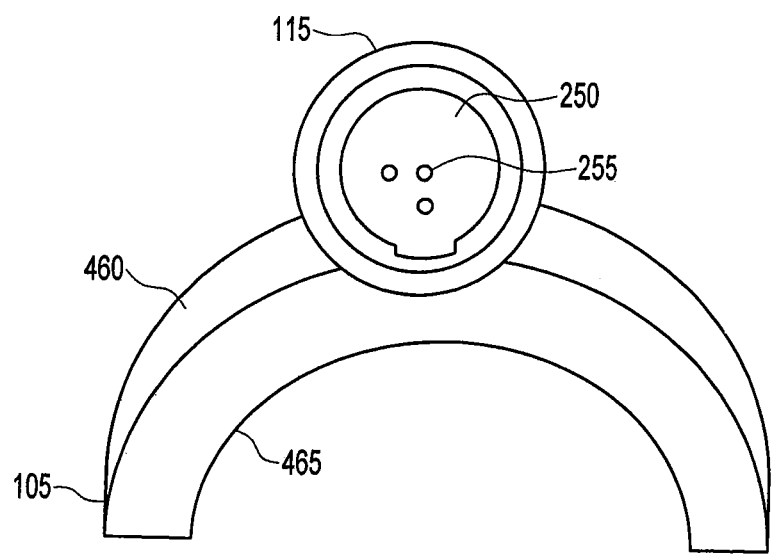
FIG. 10d shows, in perspective view, an illumination frame having a rectangular shape according to one embodiment of the invention.
Figure 10E:
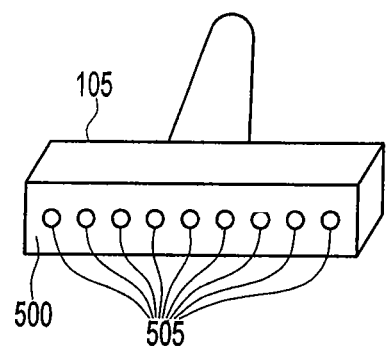
FIG. 10e shows, in perspective view, the illumination frame of FIG. 12 with slots to mate with a lip retracting device according to one embodiment of the invention.

In another embodiment, as shown in FIG. 10d, the illumination frame 105 has a generally rectangular shape and a substantially flat front surface 500 with a plurality of light sources 505 arranged along the front side 500. FIG. 10e is a perspective view of an alternative arrangement of the illumination frame of FIG. 10d. The illumination frame 105 has a first slotted structure 520 on one end and a second slotted structure 525 on the other end. Each slotted structure 520, 525 is disposed forwardly from the front side 500 of the illumination frame 105. The slots 530, 535 in each slotted structure 520, 525 begin at respective front ends 540, 545 of the slotted structures 520, 525 and are disposed inwardly toward the front surface 500 of the illumination frame 105, and are configured and arranged to mate with the formations, such as wing-like members, of a reference device, such as a lip retracting device 350, shown in FIG. 15 to facilitate alignment of the illumination frame 105 with a patient's teeth.

Figure 22:
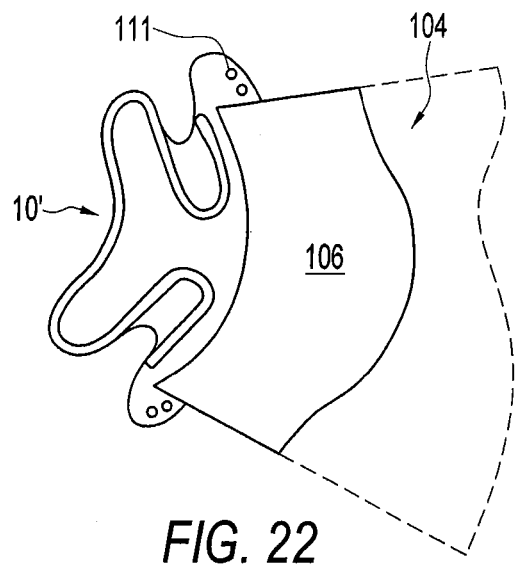
FIG. 22 depicts a semi-schematic bottom plan view of the lip retracting device of FIG. 21a fitted into a device, such as an output port, a light guide of a lamp source or an examination cone.
Figure 22A:
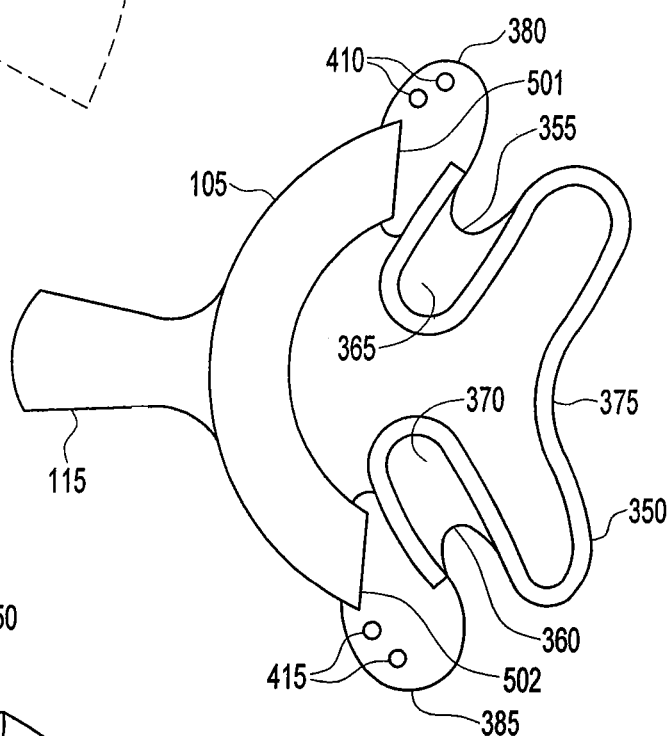
FIG. 22a shows a top view of an illumination frame mated with a lip retracting device according to one embodiment of the invention.
Figure 22B:
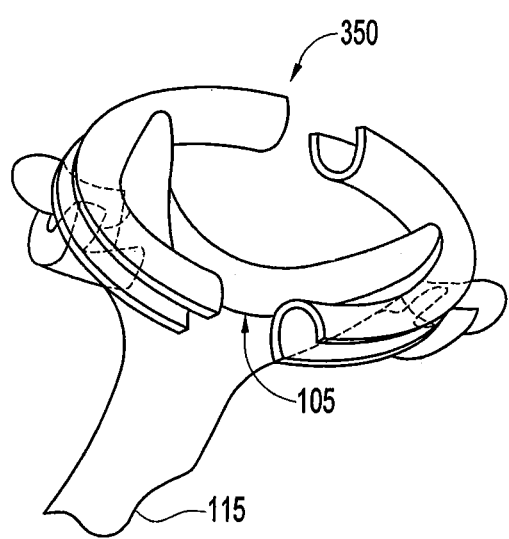
FIG. 22b shows another embodiment of an illumination frame mated with a lip retracting device according to one embodiment of the invention.

In other embodiments of the invention, the illumination frame 105 may be shaped and configured to mate with a reference device such as a lip retracting device worn by the patient, such as shown in FIGS. 22a and 22b, thereby providing a substantially precise alignment with the patient's mouth.

Figure 10F:
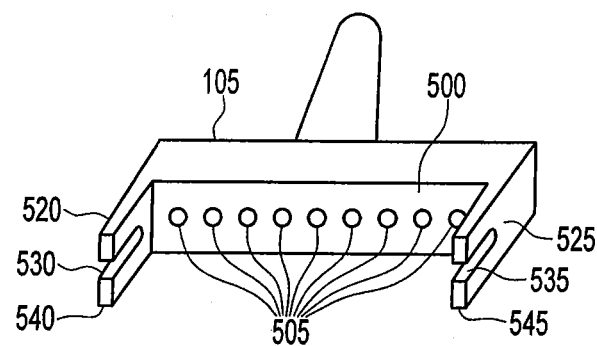
FIG. 10f shows an embodiment of an illumination frame including a heat sink.
Figure 10G:
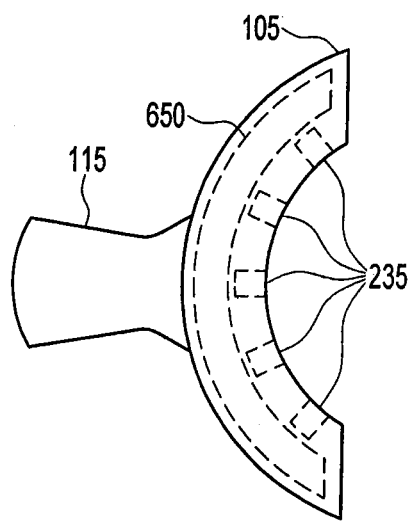

FIG. 10f is a top view of an illumination frame 105 including a heat sink according to one embodiment of the invention. The illumination frame 105 has a plurality of light sources 235, having a heat sink 650 coupled to their ballasts (or, base). The heat sink 650 may be made of any material as mentioned above, including a phase change material. The heat sink may also be of any shape.

Figure 12:
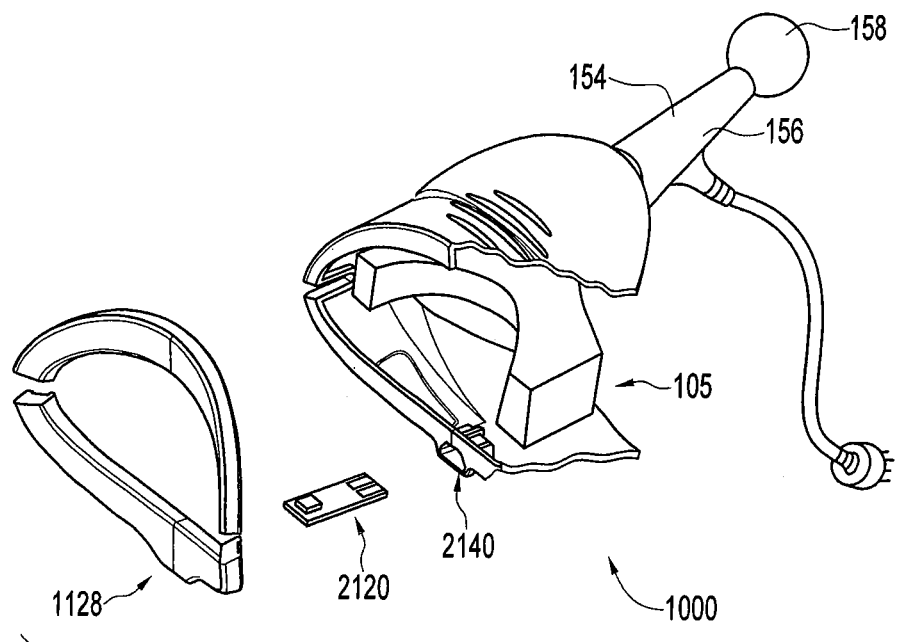
FIG. 12 shows an exploded view of a light guide with an illumination frame.
Figure 21:
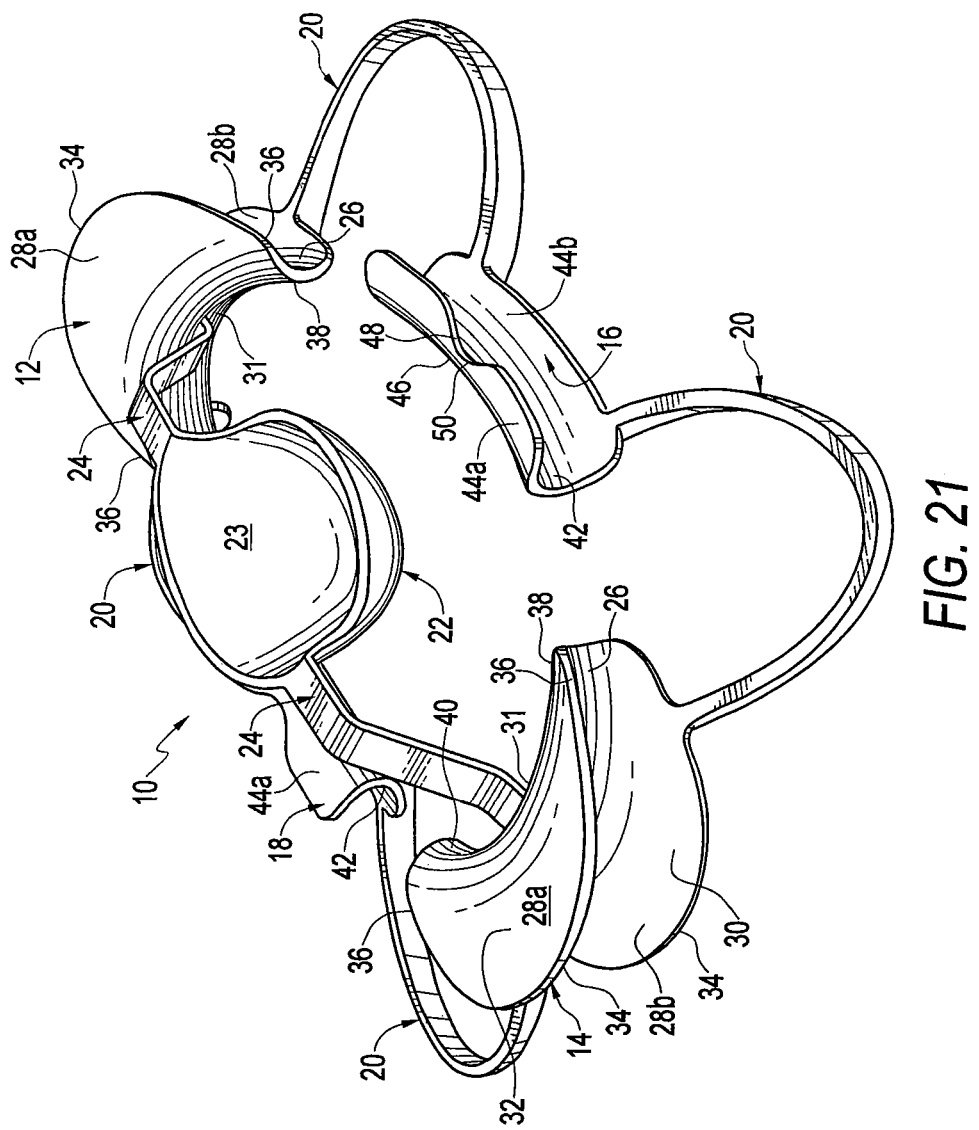
FIGS. 21 and 21b depict a semi-schematic perspective view of a lip retracting device provided in accordance to one embodiment of the present invention.
Figure 21A:
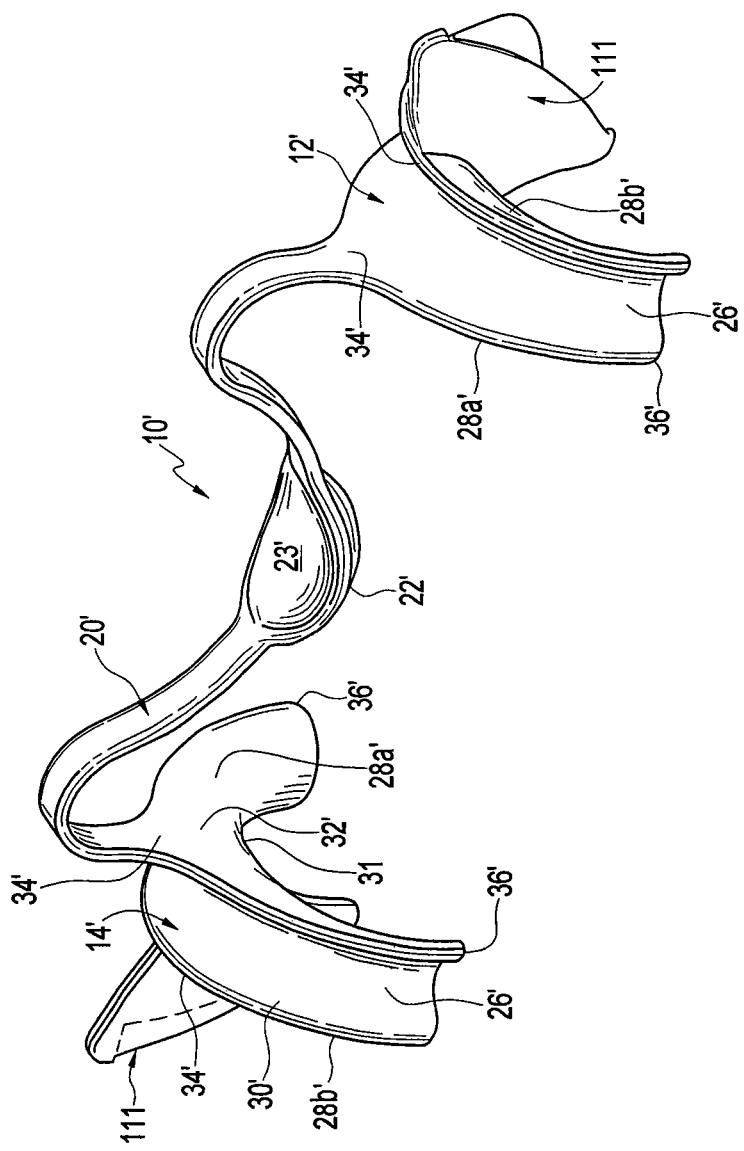
FIG. 21a depicts a semi-schematic perspective view of an alternative lip retracting device provided in accordance to another embodiment of the present invention.

In some exemplary embodiments, for example, FIG. 12, the illumination frame 105 may be attached to or disposed inside a spacer, such as a light guide 106, having formations, such as slots for engaging with a reference device, such as a lip retracting device 1138, as shown in FIGS. 21a and b, also having formations, such as wing-like members 111, for positioning the illumination frame 105. An elastic member 1128 is disposed between the patient and the light guide 106. The elastic member 1128 serves to cushion the interface between the patient and the light guide 106, absorbing shocks which might otherwise be painful or uncomfortable.

Figure 13:
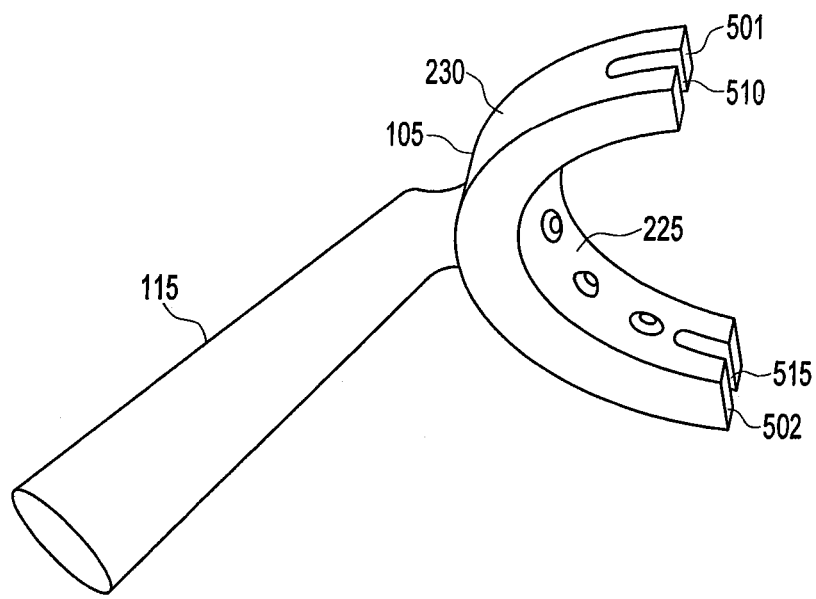
FIG. 13 shows, in perspective view, an illumination frame having slots according to one embodiment of the invention.

In another aspect, the illumination frame 105 may be a self-contained structure, such as shown in FIGS. 10, 12, 13 and 14. In FIG. 13, the illumination frame 105 has a generally arcuate shape having a first end 501 and a second end 502. The back 230 of the illumination frame 105 is convex and the front 225 of the illumination frame 105 is concave. The illumination frame 105 may also serve as the spacer having formations. In other words, the spacer and formations, for example, slots, may both be present on the lamp housing, such as the illumination frame 105, as exemplified in FIG. 22b. The ends 500, 505 each has a slot 510, 515 open from the front 225 of the illumination frame 105 towards the back 230 of the illumination frame 105. Each slot 510, 515, extends inwardly from its respective end 501, 502 of the illumination frame 105. The slots 510, 515 are located and configured to mate with the formations of a reference device, such as the wings 111 of a lip retracting device 1138, as shown in FIGS. 21a and b.

The light sources of the illumination frame 105 may be of one wavelength, or may be of different wavelengths, as mentioned above.

Figure 14:
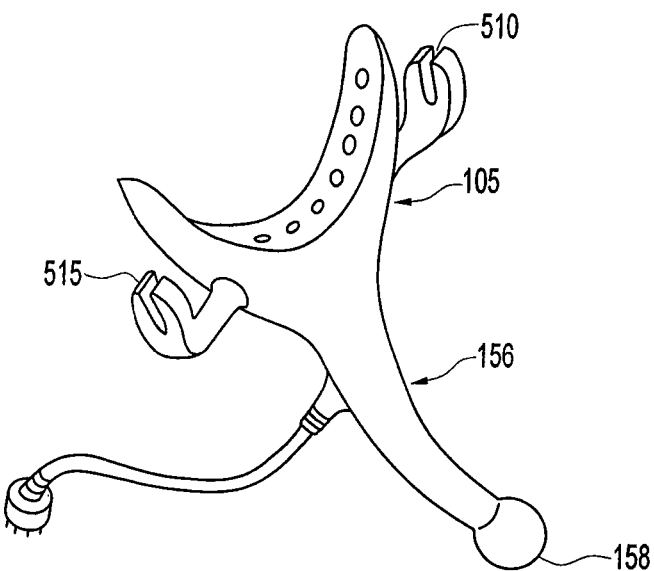
FIG. 14 shows, in perspective view, another embodiment of an illumination frame.
Figure 15:
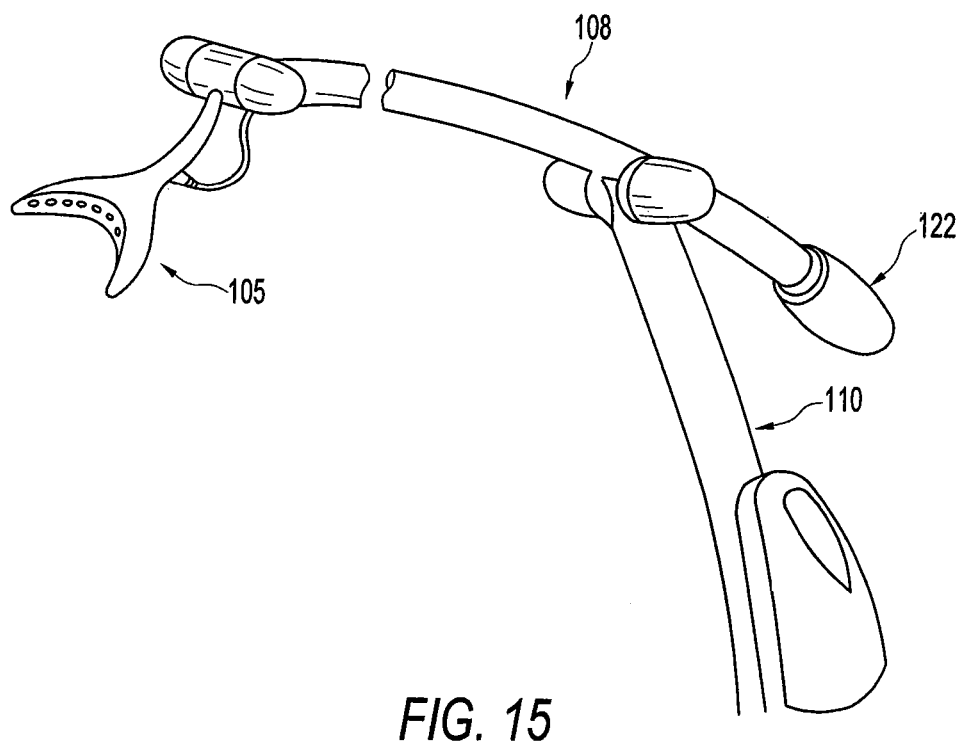
FIG. 15 shows, in perspective view, an illumination frame mounted onto a support structure.

As also noted above, the illumination frame 105 may also include a pivot mount 154 and a ball swivel 158 at the end of the shaft 156, as shown in FIG. 14. In another embodiment, the illumination frame 105, such as that exemplified in FIG. 12, may be attached to the support system of FIG. 1. As noted above, the boom 108 is adjustably positionable with respect to the mast 110, as shown in FIG. 15. The boom 108 has both a rotational and a tilt range of motion with respect to the mast 110. A counterweight 122 on the second end of the boom 108 provides a counterbalance for the illumination frame 105.

The attachment is also similar to FIG. 7 above, and is described below in the illustrated embodiment of FIG. 15a, where the ball joint 902 is coupled to an illumination frame housing 1150. The housing 1150 includes a first elongate portion 1152 having at its posterior end the ball of the ball and socket joint 902. A signal cable 1170 is coupled at one end to the housing 1150. The signal cable may include a power cable adapted to provide power for the one or more illumination sources 1156 disposed on front face 1154. The single cable may also include an optical light guide such as an optical fiber adapted to transmit light to the one or more illumination sources from a remote light source. In at least one embodiment of the invention, the signal cable 1170 includes a strain-relief feature 1172.

Figure 15A:
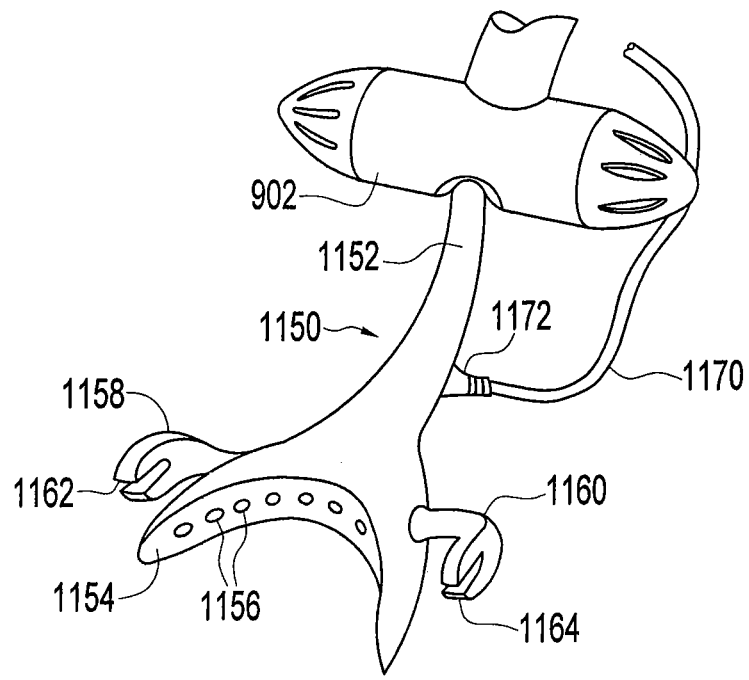
FIG. 15a shows, in more detail, the illumination frame and a portion of the support structure.

The embodiment of FIG. 15a shows first and second formations, such as wing-coupling members 1158, 1160. Each wing-coupling member 1158, 1160 includes a respective slot 1162, 1164. The slots 1162, 1164 are adapted to receive corresponding wing-like members 1134, 1136 of a reference device, such as a lip retracting device described below.

Figure 16:
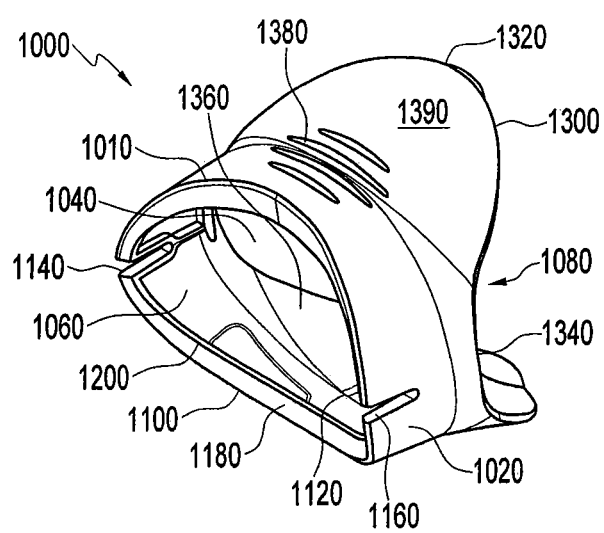
FIG. 16 shows, in perspective view, a light guide according to one embodiment of the invention.

As noted above, the spacer may be a light guide 1000, as shown in FIG. 16, which includes an elliptically tubular member 1020 having an axial cavity 1040 disposed between a front aperture 1060 and a rear aperture 1080.

As shown in the illustrated embodiment, a first edge 1010 of the tubular member defines a substantially elliptically saddle shaped curve having a convex form in relation to a generally horizontal portion 1100 thereof and a concave form in relation to a generally vertical portion 1120 thereof. In addition, edge 1010 includes first and second substantially horizontal slots 1140, 1160. According to one embodiment of the invention, the slots 1140, 1160 are disposed substantially coplanar with respect to one another and are disposed substantially coincident with a major axis of the elliptically saddle shaped curve that defines edge 1010.

A rim 1180 extends radially inwardly from the edge 1010 to a second substantially elliptically saddle shaped curved edge 1200 (also referred to as the "second edge"). The second edge 1200 is disposed in substantially constant spatial relation to edge 1010, whereby the rim 1180 has a substantially uniform radial dimension over the length of edge 1010. Edge 1200 defines an outer periphery of the front aperture 1060.

At the rear end of the embodiment of FIG. 16, a third edge 1300 defines another curve that is of an approximately elliptically saddle shape. Edge 1300 is substantially concave in form in relation to a generally horizontal portion 1320 thereof and is generally convex in form in relation to a generally vertical portion 1340 thereof.

According to one embodiment of the invention, curve 1300 defines the rear aperture 1080 of the light guide.

According to one embodiment of the invention, the light guide does not include a rim adjacent the rear aperture 1080.

In one aspect of the illustrated embodiment, an outer surface 1390 of the light guide is disposed between edge 1010 and edge 1300. An inner surface 1360 of the light guide is disposed in a substantially uniform spatial relation to outer surface 1390 so as to define inward and outward boundaries of the elliptically tubular member 1020.

In one embodiment of the invention, outer surface 1390 includes a plurality of gripping features 1380 adapted to improve the grip of an operator on surface 1390 during manipulation of the light guide 1000. In the illustrated embodiment, the gripping features 1380 have a raised elongated ellipsoid aspect. In another embodiment of the invention, the gripping features include a plurality of substantially hemispherical bumps. In still another embodiment of the invention, the gripping features include a plurality of zigzag grooves. One of skill in the art will appreciate that a wide variety of features may be disposed on surface 1340, so as to enhance overall gripability of the light guide 1000.

Figure 17:
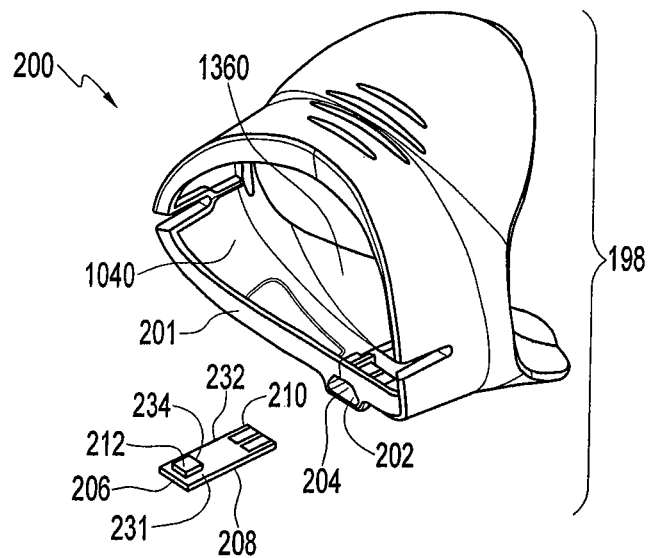
FIG. 17 shows, in perspective view, a light guide including a recording device according to one embodiment of the invention.

FIG. 17 shows a light guide 200 according to another embodiment of the invention. The light guide 200 includes a rim 201 with an aperture 202 in a lower portion thereof. The aperture 202 opens inwardly from a front end of the light guide 200 into an elongated cavity 204 formed, in part, by the inner wall 1360 of the light guide. According to one embodiment of the invention, the cavity 204 is adapted to receive a recording device 206 therein.

According to one embodiment of the invention, the recording device 206 includes an assembly having a printed circuit board 208 with an electromechanical contact 210 and a memory integrated circuit 212 disposed thereon. In one aspect, the recording device 206 includes a first side 231 and a second side 232. In the illustrated embodiment, the memory integrated circuit 212 has a rear side 234. Pursuant to one embodiment of the invention, the memory integrated circuit 212 is substantially permanently fixed to the circuit board by, for example, soldering, adhesive bonding, potting or other methods for integrated circuit mounting as are known to those of ordinary skill in the art.

According to one embodiment of the invention, the cavity 204 is defined by a plurality of surfaces, adapted to support the recording device 206 substantially fixedly with respect to the light guide 200.

In one embodiment of the invention, the recording device 206 is supported in a position such that the electro-mechanical contact 210 is disposed in an elevated and exposed location within axial cavity 1040 of the light guide 200.

Figure 18:
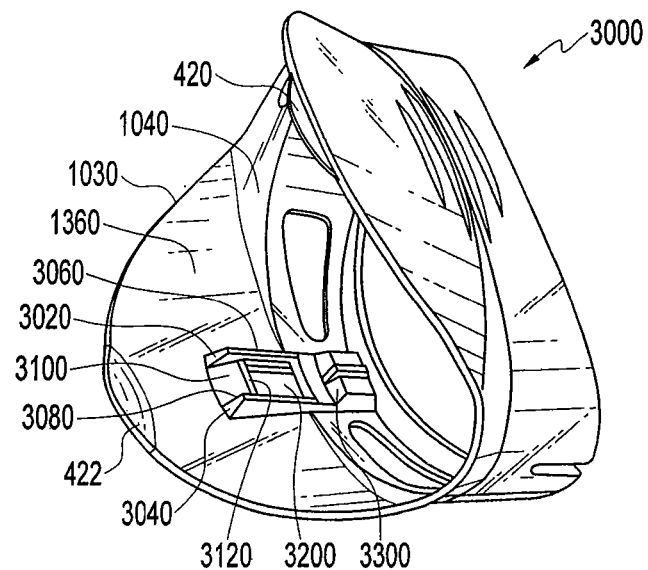
FIG. 18 shows, in posterior perspective view, a light guide according to one embodiment of the invention.

This spatial relationship is shown more clearly in, for example, FIG. 18 which shows a posterior perspective view of a light guide 3000 having disposed on the internal surface 1360 a first support member 3020 and a second support member 3040. Support member 3020 includes a first bearing wall 3060 and support member 3040 includes a second bearing wall 3080. A third support member 3100 includes a bearing top surface 3120.

Turning once again to recording device 206 (as shown in FIG. 17) one sees that recording device 206 is adapted to be received within a region 3200 as shown in FIG. 18. When recording device 206 is disposed in region 3200, bearing surface 3060 is disposed adjacent to and supports edge 231. The bearing surface 3080 is disposed adjacent to and supports edge 232 and bearing surface 3120 is disposed adjacent to and supports an underside surface (not shown) of recording device 206.

As a further feature of light guide 3000, a surface 3300 is disposed in a generally vertical orientation. A further surface is disposed in substantially parallel spatial relation to surface 3300, and forwardly of the same.

Figure 19:
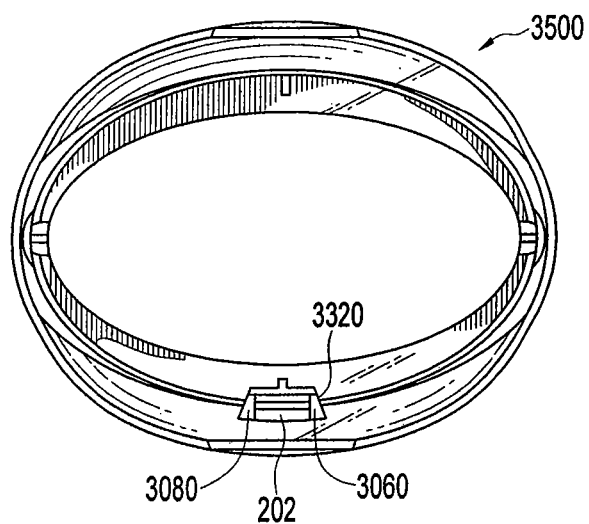
FIG. 19 shows a front elevation of a light guide according to one embodiment of the invention.

Further insight into recording device 206 and its role in the invention is gained by reference to FIG. 19 which shows a light guide 3500 according to one embodiment of the invention in anterior elevation. Specifically, FIG. 19 shows the further bearing surface 3320 disposed in substantially parallel spatial relation to surface 3300 (as shown in FIG. 18) as discussed immediately above. Also shown are aperture 202 (as discussed above in relation to FIG. 17), first bearing wall 3080 and second bearing wall 3060 (as discussed above in relation to FIG. 18).

Figure 17A:
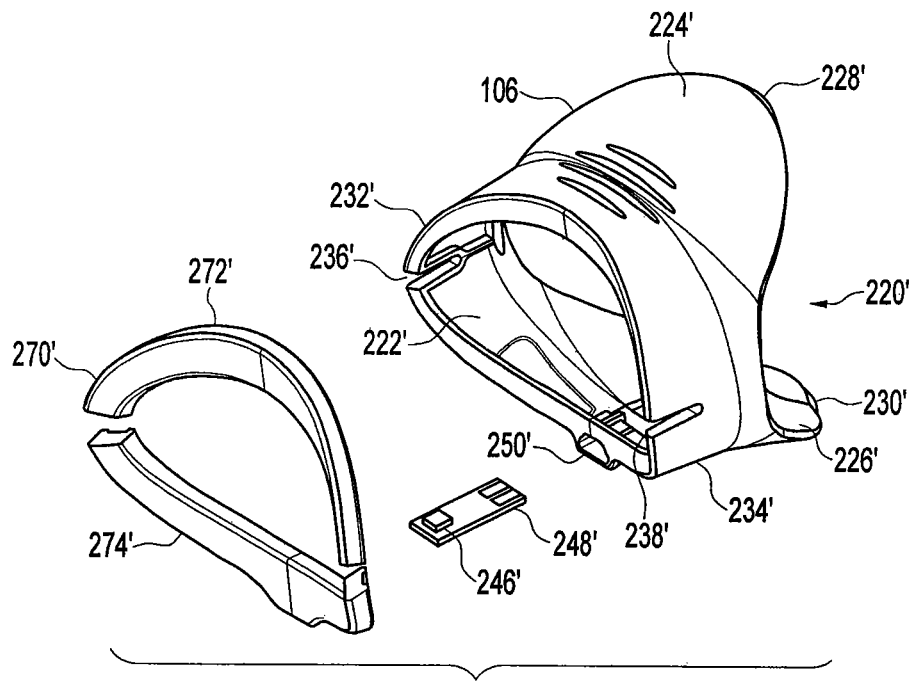
FIG. 17a shows, in exploded perspective view, a light guide having a recording device and an elastic protector.

FIG. 17a shows another embodiment of the light guide 106 of a generally ellipsoidal shape having a first opening 220' at one end that attaches to the lamp head housing 104 and a second opening 222' at the other end that interfaces with the patient. The first opening 220' has extended edges 224', 226' that extend substantially parallel to the long diameter of the oval formed by the light guide 106.

Figure 21B:
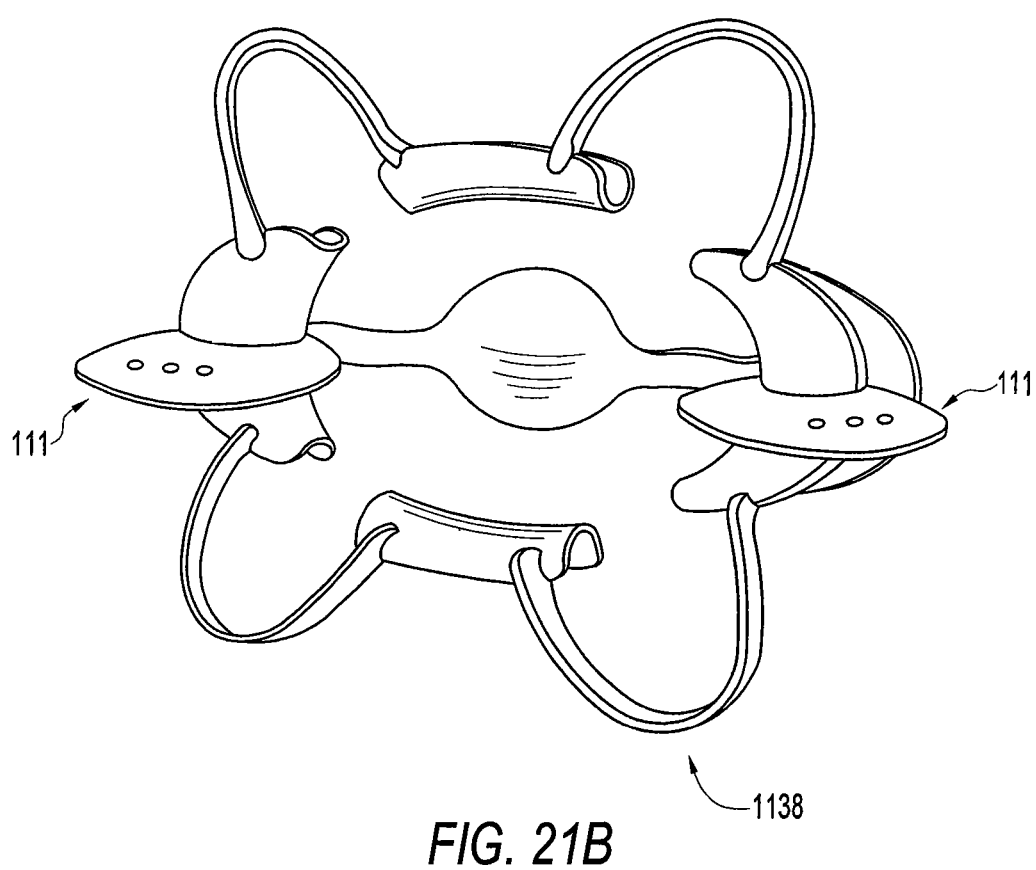

The extended edges 224', 226' form a curved interface configured to mate with the lamp head housing 104. The light guide 106 mechanically couples to the lamp head housing 104. A first protrusion 228' on extended edge 224' and a second protrusion 230' on extended edge 226' are configured to mate with indentations on the lamp head 102 and act to hold the light guide 106 to the lamp head housing 104. A first slot 236' and a second slot 238' on opposing sides of the second opening 222' of the light guide 106 may be configured to mate with a reference device, such as a lip retracting device 1148, worn by the patient as illustrated in FIGS. 21a and 21b described below to align the lamp head 102 accurately with the patient.

In one embodiment, an elastic protector 270 is mounted around the second opening 222' of the light guide 106 to provide a soft interface between the light guide 106 and the patient. The elastic protector 270 may be made of any opencell or closed-cell foam, rubber or elastomer, such as described above for the soft overlays, and is attached to the light guide 106 by means of heat sealing or an adhesive. In some embodiments, the elastic protector 270 may be present in pieces 272, 274, which may again be attached to the light guide 106 by means of heat sealing or an adhesive. Suitable adhesives may include, but are not limited to, structure adhesives, hot melt adhesives, pressure-sensitive adhesives, reactive adhesives or the like. Alternatively, suitable adhesives may be acrylic-based, polyurethane-based, epoxy-based, polyamide-based, styrene copolymer-based, polyolefin-based or similar. Further, the elastic protector pieces 272, 274 may also be integrally molded onto the light guide 106.

In the present embodiment, the elastic protector 270 is made in two pieces, an upper portion 272 and a lower portion 274, extending the slots 236', 238' of the light guide 106 so as to accommodate the wing-like members of an exemplary lip retracting device.

According to one embodiment of the invention, a light guide 106, such as that exemplified in FIG. 17a, is intended to be a single-use item, used for one patient, or one time dental whitening treatment, filling procedure, or imaging, and then discarded. With this in mind, in the illustrated embodiment of FIG. 17a, the light guide 106 further includes a memory integrated circuit 246' disposed within a space 250' molded into the underside of the light guide 106. The memory integrated circuit 246' stores a record of a duration of use signal indicating how long the particular light guide has been in use. The light guide memory integrated circuit 246' is part of a system for ensuring that the light guide 106 is not improperly reused.

The biocompostable or biodegradable polymers, including those mentioned above, are particularly suited for single use light guides.

In operation, the light guide 106 is attached to the lamp head housing 104. The light guide 106 has both a mechanical attachment mechanism (the slots 228', 230') as described above and an electrical contact 248 between the light guide memory integrated circuit 246' and electronics in the lamp head housing 104. The electrical contact 248' mates with a conductive projection in the lamp head forming an electro-mechanical connection that enables signaling between the light guide memory integrated circuit 246' and electronics in the lamp head housing 104.

The light guide 106 is aligned with the patient's mouth using the positionability of the lamp system 100 and whitening treatment is administered. A signaling device within lamp head 102, or within the power pack, records duration of use of light guide usage onto the memory integrated circuit 246'. When a light guide usage limit is reached, the lamp system 100 precludes activation of the light source 300 in the lamp head housing 104 and the light guide 106 is replaced in order to operate the lamp system 100.

In an alternative embodiment of the light guide 106, no elastic protector 270 is used to interface between the light guide 106 and the patient. In further alternative embodiments of the light guide 106, the contact between the light guide memory integrated circuit 246' and electronics in the lamp head 102 is a magnetic contact. Alternatively, the memory integrated circuit 246' may communicate with the lamp head 102 through infrared radiation or through wireless radio signals or through light from the visible portion of the electromagnetic spectrum.

One of skill in the art will appreciate that when recording device 206 (as illustrated in FIG. 17) is disposed inwardly of aperture 202, surface 234 of integrated circuit memory device 212 is disposed adjacent to, and supported by bearing surface 3320. Furthermore, referring again to FIG. 18, one of skill in the art will appreciate that when recording device 206 is thus disposed, electromechanical contact 210 will be disposed in a region adjacent and rearwardly of bearing surface 3120 and will be exposed within axial cavity 1040 from above, below, and from a rearward direction.

The structure of a light guide may include a UV-inhibiting material in order to protect the patient's skin from ultra-violet light exposure. The light guide may be made of similar material as that of the lamp housing 104 and lamp head 102 as described above. Additionally, like the lamp housing 104 and the lamp head 102, a liquid crystal polymer, one that reflects rather than transmits light energy, may be used, either as a coating or as the main ingredient of the light guide to minimize escape of light energy.

Figure 20:
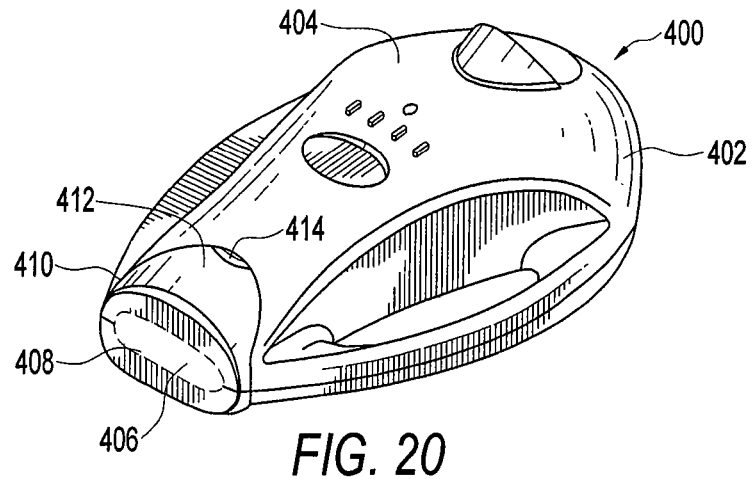
FIG. 20 shows, in perspective view, a dental lamp head adapted to be coupled to a light guide according to one embodiment of the invention.

For illustrative purposes, FIG. 20 shows a lamp head 400 which includes a housing 402 having an outer surface 404. A forward end of the lamp head housing 402 includes an aperture 406 defined by an edge 408. In operation, light is emitted from a light source within the lamp head housing 402 through the aperture 406.

The housing 402 includes an intermediate edge 410 disposed in a curve about aperture 406 in a forward region of the housing 402. Forwardly of the intermediate edge 410, a surface region 412 is recessed in relation to the balance of the housing surface 404.

According to one embodiment of the invention, the lamp head 400 is adapted to removably interface with a light guide such as that indicated, for example by reference 3000 in FIG. 18. Accordingly, surface region 412 is adapted to be disposed adjacent to and to be supported by, internal surface 1360 of light guide 3000. Likewise, rear edge 1300 of light guide 3000 is adapted to be disposed adjacent to and supported by edge 410.

In addition, according to one embodiment of the invention, the housing 402 includes a top recess 414, and a corresponding bottom recess (not shown). The top recess 414 is adapted to receive a first detent projection 420 (as shown in FIG. 18) disposed adjacent edge 1300 of light guide 3000. In like fashion, the bottom recess is adapted to receive a second detent projection 422 as shown in FIG. 18.

According to one embodiment of the invention, the material of the light guide is sufficiently elastic to urge detent projections 420 and 422 into their respective recesses, whereby the light guide is removably retained in position with axial cavity 104 disposed adjacent to aperture 406 out the lamp head.

Figure 20A:
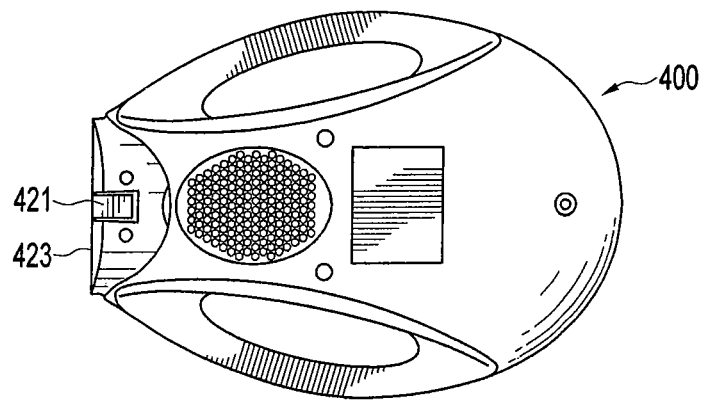
FIG. 20a shows a top view of a dental lamp head adapted to be coupled to a light guide according to one embodiment of the invention.

According to one embodiment of the invention, when the light guide (e.g., 3000) is so disposed, the electromechanical contact 210 (as shown in FIG. 17) is disposed within an electrical plug on the lamp head. This is shown more clearly in FIG. 20a, which includes a further recessed region 421 in proximity to the front end 423 of the lamp head 400.

Figure 20B:
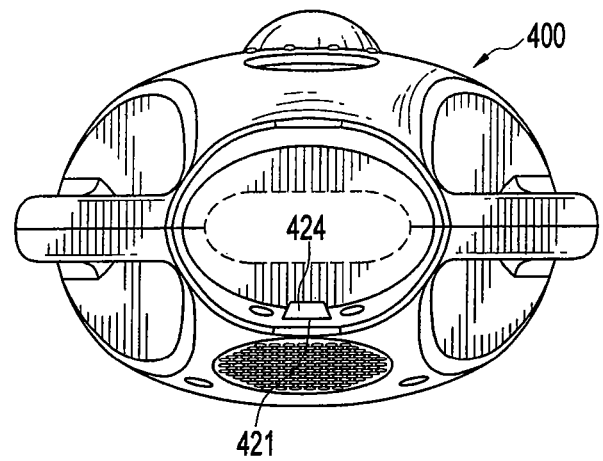
FIG. 20b shows a rear elevation of a dental lamp head adapted to be coupled to a light guide according to one embodiment of the invention.

As shown in FIG. 20b, this further recessed region 421 is disposed adjacent to the electrical plug referred to immediately above, which is disposed behind an aperture 424 in the housing 402 of the lamp head 400. The aperture 424 is adapted in size and shape to receive the electromechanical connector 210, as shown in FIG. 17, therethrough.

As mentioned above, the interaction of detent projections 420, 422 and corresponding recesses, e.g., 414 of lamp housing 400 served to maintain the light guide in position on the lamp housing once it is installed there until it is actively removed.

A plurality of light guides having output ends of varying sizes corresponding to varying mouth sizes may be provided.

As also noted above, it is desirable to position and orient the lamp head in substantially fixed relation with respect to a target of the lamp's illumination, such as a tooth. For example, during a dental whitening process, it is desirable to maintain the distance and orientation between illumination source fixedly contained within the lamp head and a target tooth bearing a whitening compound, so as to maintain substantially uniform illumination intensity over the target tooth both spatially and during the duration of a whitening procedure.

One way of accomplishing this objective is through the use of a reference device, such as a lip retracting device 10, as shown in FIG. 21, which is adapted to also retract the upper and lower lips (herein "lips") for facilitating examination and/or treatment of the mouth and/or teeth provided in accordance with one practice of the present invention. The lip retracting device 10, which may be also known as a tongur cup, includes four spaced apart channel retainers 12, 14, 16, 18, also known as flanges, for retaining four corresponding portions of the lips for examination and/or treatment of the mouth or teeth. When used, the lip retracting device 10 draws back the lips, which retracts the cheeks, to expose the mouth so that a health care professional can more easily see the teeth and work on the teeth and/or mouth.

The four channel retainers include two side channel retainers 12, 14 for retaining the ends of the lips, approximately where the upper and the lower lips intersect, and two lip channel retainers 16, 18 for retaining the mid-section of the upper and lower lips. More particularly, the four channel retainers or flanges 12, 14, 16, 18 are adapted to cup the lips and bias them open to expose the teeth for treatment and/or examination.

A plurality of resilient members 20 are incorporated in the lip retracting device 10 to interconnect the four channel retainers 12, 14, 16, 18 together and to function as biasing means. In the ready position (before insertion of the lip retracting device into the mouth), the resilient members 20 are arched outwardly with respect to the center portion of the lip retracting device 10. As further discussed below, when the lip retracting device 10 is inserted into the mouth and the four channel retainers 12, 14, 16, 18 cup respective portions of the lips, the resilient members 20 provide a retractive force to retract the lips radially outwardly for examination and/or treatment.

An optional tongue retainer 22 is shown approximately centrally positioned relative to the four channel retainers 12, 14, 16, 18. The tongue retainer may also be positioned asymmetrically about the two channel retainers 16 and 18. The tongue retainer 22 comprises a trough 23 and is attached to two channel retainers 12, 14 by a pair of secondary resilient members 24. When incorporated, the tongue retainer 22 and the secondary resilient members 24 cooperate to block the tongue and limit the tongue to the back vicinity of the mouth, thus enabling access to the lingual portion or back of the teeth for examination and/or treatment. In short, the tongue retainer is configured to minimize interference by the tongue during treatment and/or examination by a health care professional.

The side channel retainers 12, 14 resemble a curvilinear c-channel in that they include an arcuate race 26 and two channel side walls 28a, 28b. The channel side walls 28a, 28b resemble a bell shape and include a maximum wall dimension at approximately the mid-point 34 and two smaller tapered tips 36 at the ends thereof. In one embodiment, the inside side wall 28a, which is intraoral, as further discussed below, may be slightly larger relative to the outside side wall 28b. However, the relative dimensions may be reversed or may be the same without deviating from the functionality of the lip retracting device 10.

The side channel retainers 12, 14 further include an interior surface 30 and an exterior surface 32. The arcuate race 26 comprises a radius of curvature 31 adapted to mimic the curvature of the side of the lips when the lips are in the opened position. Because this curvature may vary depending on the size and age of the user or patient, the lip retracting device 10 may be implemented with varying radius of curvatures 31 to fit the varied shape of the particular user/patient. The arcuate race 26 may also include an irregular curvature or two or more different radii of curvatures. For example, the lower region 38 of the radius of curvature 31 may have a larger radius than the upper region 40 or vice versa. If implemented, the irregular curvature can vary the amount of retraction of the portion of the lip seated within the arcuate race to vary the amount of retraction between those portions of the lip. The two lip channel retainers 16, 18 may also have different radii of curvatures, similar to the side channel retainers 12, 14.

The lip channel retainers 16, 18, like the side channel retainers 12, 14, resemble a curvilinear c-channel in that they include an arcuate race 42 and two channel side walls 44a, 44b. In one embodiment, the radius of curvature 46 of the lip channel retainers is larger than the radius of curvature 31 of the side channel retainers 12, 14. The larger radius of curvature 46 enables the lip channel retainers 16, 18 to conform to the contour of the upper and lower lips near the frenum, which is more planar relative to the side of the lips. Depending on the size and age of the intended user/patient, the radius of curvature 46 of the lip channel retainer 16, 18 may also vary.

As shown, a frenum release 48 is incorporated in the inside side walls 44a of the lip channel retainers 16, 18 for providing relief to the frenum of the upper and lower lips. In one embodiment, the frenum release 48 includes a partial oval shaped cutout having a size sufficient to provide clearance for the frenum. In other words, the frenum release 48 should be such that the lowest most portion 50 of the frenum release only slightly touches the frenum when in use, and for example, does not touch the frenum. Although the oval shaped cutout is shown for the frenum release 48, a partial circle, a rectangular cutout, a square cutout, or other geometrical shaped cutout may also be incorporated without deviating from the function of the frenum release.

The lip retracting device 10 may be made by injection molding or casting a thermoplastic material such as polypropylene, polyethylene, polystyrene, polyester, polycarbonate or the like. The lip retracting device 10 may also be made out of biocompostable or biodegradable polymers mentioned above. More for example, the lip retracting device 10 may be made by injection molding polypropylene and may have a smooth and transparent finish.

As shown in FIG. 21b, two wing-like flanges 111 may be incorporated in the lip retracting device of FIG. 21. These wing-like flanges 111 may be permanently attached by an adhesive or by heat sealing, or molded or cast integrally with the side channel flanges or retainers 12, 14, and may be constructed of the same or different material as the channel flanges or retainers, including the materials mentioned above. An exemplary illumination system is shown in FIG. 32, which is an exploded view of the combination of a lip retracting device 1138, a light guide 1104 and a lamp system 1102.

The wing-like flanges 111 are designed for fitting into a pair of slots 1130, 1132 formed in the output port or light guide 1104 of a lamp system 1102 used in a whitening process or to the slots in any examination device. Another exemplary illumination system and the use of which is disclosed in Ser. No. 10/715,681, filed Nov. 17, 2003, which is expressly incorporated herein by reference as if set forth in full.

In another embodiment, instead of a light guide 1104, an examining device such as a cone-like structure, as mentioned above, may be configured to fit over the outlet of the lamp system 1102 and the wing-like flanges 111 on the lip retracting device 1138 may be configured to interact with the slots on the cone to thereby provide a consistent and controlled gap between the lamp system and the teeth of the patient to be treated or examined. The wing-like flanges 111 may be constructed in the manner shown and described above for the wing-like flanges with reference to FIGS. 21a and 22.

Figure 23:
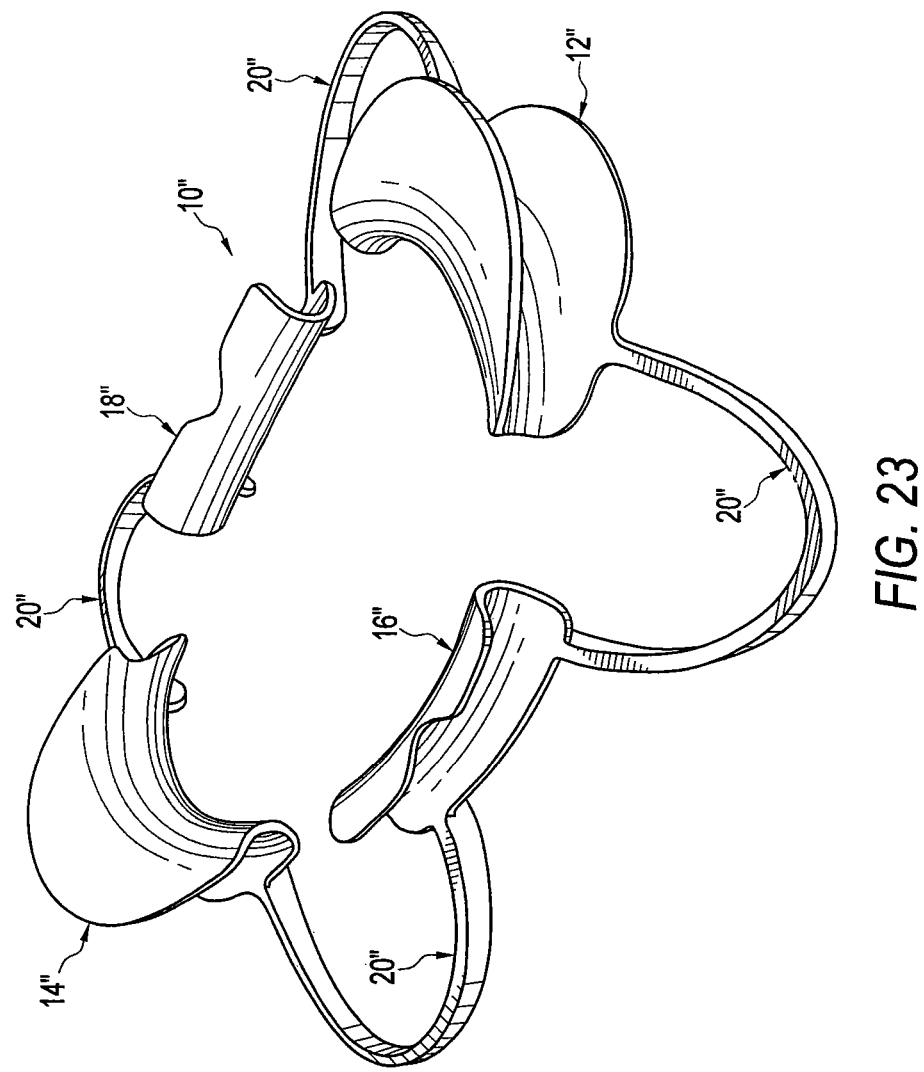
FIG. 23 depicts a semi-schematic perspective view of an alternative lip retracting device provided in accordance to another embodiment of the present invention.
Figure 24:
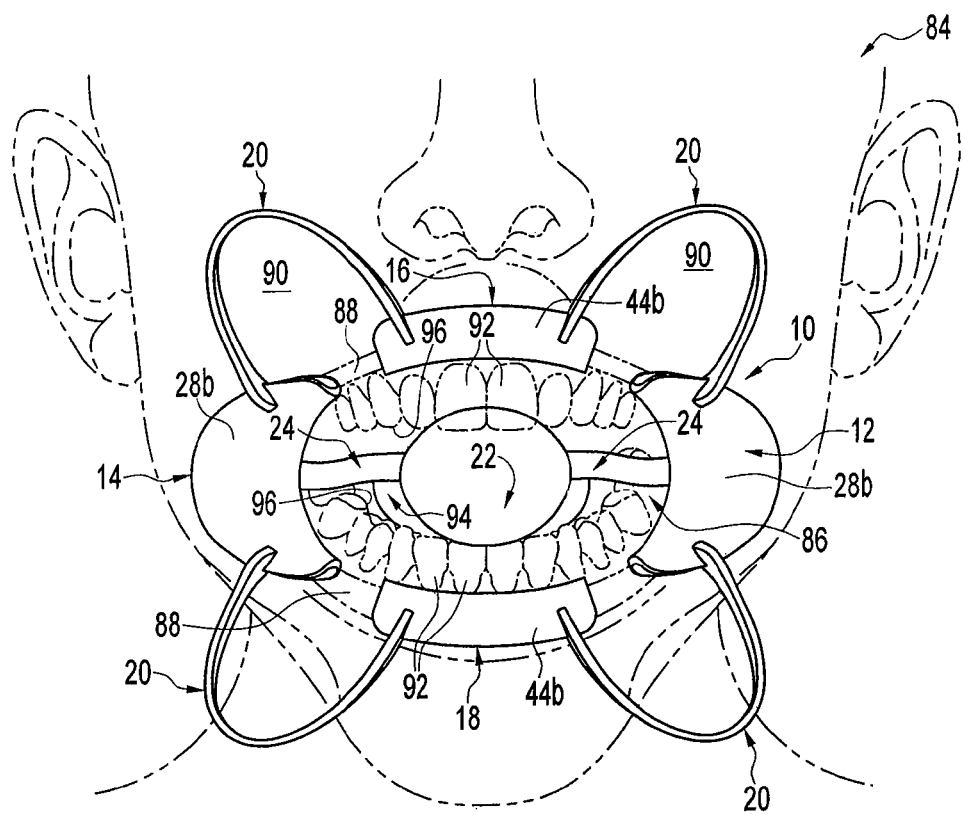
FIG. 24 depicts a semi-schematic front view of the lip retracting device of FIG. 21 in service on a user/patient.

Referring now to FIG. 21a, there is shown another embodiment of a lip retracting device 10' for retracting the lips for facilitating examination of the mouth and/or teeth, the whitening or curing process. The device includes two spaced apart channel retainers 12', 14', also known as flanges, for retaining two corresponding portions of the lips for examination and/or treatment of the mouth or teeth. When used, the lip retracting device 10' draws back the lips, which retracts the cheeks, to expose the mouth so that a health care professional can more easily see the teeth and work on the teeth and/or mouth, similarly as shown in FIGS. 23 and 24.

The two channel retainers 12', 14' are for retaining the ends of the lips, approximately where the upper and the lower lips intersect. More particularly, the two channel retainers or flanges 12', 14' are adapted to cup the lips and bias them in the open position to expose the teeth for treatment and/or examination.

A resilient member 20' is incorporated in the lip retracting device 10' to interconnect the two channel retainers 12', 14' together and to function as biasing means. The resilient member 20' has two arches, one on either side of the center portion 22'. The resilient member 20' may be formed as a single piece integrally molded or attached to the inside side walls 28a' of the channel retainers 12', 14', or it may be formed in two halves separately connected to the mid-portion 22', also integrally molded or attached to the inside side wall 28a' of the channel retainers 12', 14'. In the ready position (before insertion of the lip retracting device into the mouth), the resilient members 20' are arched outwardly with respect to the center portion of the lip retracting device 10'. As further discussed below, when the lip retracting device 10' is inserted into the mouth and the two channel retainers 12', 14' cup respective portions of the lips, the resilient members 20' provide a retractive force to radially retract the lips outward for examination and/or treatment. This lip retracting device is especially useful for the whitening process.

An optional tongue retainer 22' can also be approximately centrally positioned relative to the two channel retainers 12', 14'. Like the tongue retainer 22 of FIG. 21, the tongue retainer 22' of the present embodiment may also include a trough 23'. Further, it may be integrally formed on the mid-portion of the resilient member 20' and thus be attached to the channel retainers 12', 14' via resilient member 20'. When incorporated, the tongue retainer blocks the tongue and limits the tongue to the back vicinity of the mouth, thus enabling access to the lingual portion or back of the teeth for examination and/or treatment. In short, the tongue retainer is configured to minimize interference by the tongue during treatment and/or examination by a health care professional. In this embodiment, the resilient member 20' acts not only to connect the channel retainers and to bias them, but also to connect the tongue retainer to the channel retainers. If the tongue retainer 22' is not incorporated, the resilient member 20' would simply extend from one channel retainer 12' to another channel retainer 14' at a substantially uniform width.

The channel retainers 12', 14' resemble a curvilinear c-channel in that they include an arcuate race 26' and two channel side walls 28a', 28b'. The channel side walls 28a', 28b' resemble a bell shape and include a maximum wall dimension at approximately the mid-point 34' and two smaller tapered tips 36' at the ends thereof. In one embodiment, the inside side wall 28a', which is intraoral, as further discussed below, is slightly larger relative to the outside side wall 28b'. However, the relative dimensions may be reversed or may be the same without deviating from the functionality of the lip retracting device 10'.

The side channel retainers 12', 14' further include an interior surface 30' and an exterior surface 32' and the description of FIG. 21 above also applies here. The arcuate race 26' comprises a radius of curvature 31' adapted to mimic the curvature of the side of the lips when the lips are in the opened position. Similarly, because this curvature may vary depending on the size and age of the user or patient, the lip retracting device 10' may be implemented with varying radii of curvatures 31' to fit the varied shape of the particular user/patient. The arcuate race 26' may also include an irregular curvature or two or more different radii of curvatures. For example, the lower region 38' of the radius of curvature 31' may have a larger radius than the upper region 40' or vice versa. If implemented, the irregular curvature may vary the amount of retraction of the portion of the lip that is seated within the arcuate race to vary the amount of retraction between those portions of the lip.

The lip retracting device 10' may also be made by injection molding or casting a thermoplastic material such as those already mentioned. For example, the lip retracting device 10' may be made by injection molding pigmented polypropylene and is opaque white or colored having a smooth finish.

Additionally, FIG. 21a also shows two formations in the shape of wing-like flanges 111 extending from the outside side wall 28b' of the channel retainers 12', 14'. The wing-like flanges 111 may be molded or cast integrally with the channel flanges or retainers 12', 14'. As further discussed below, the wing-like flanges are designed for fitting the lip retracting device 10' to the slots formed on a cone section of an output port or light guide of a lamp source used in a teeth whitening process, or to the slots in any examining device. As an example, FIG. 22 shows a bottom view of the lip retracting device 10' with its wing-like flanges 111 engaging the slots on, for example, a light guide 106, which is attached to a lamp head 104 shown in dash-dot lines.

FIG. 22a shows a top view of a reference device such as a lip retracting device 350 mated to an illumination frame 105 according to one embodiment of the invention. The lip retracting device 350 acts as a fixturing device for maintaining the illumination frame 105 in substantially fixed relation with respect to a target tooth. As shown in the illustrated embodiment, the lip retracting device 350 includes first 355 and second 360 U shaped channels adapted to receive the lips of a dental patient adjacent to respected internal surfaces 365, 370 thereof.

FIG. 22b shows another embodiment of a lip retracting device 350 mated again to an illumination frame 105. The lip retracting device again mates directly to the light source without an intervening light guide, such as is shown in FIG. 22, where 106 is the light guide and 104 is the light source.

FIG. 23 is a semi-schematic perspective view of an alternative lip retracting device 10" provided in accordance to another embodiment of the present invention. In one embodiment, this alternative lip retracting device 10" is identical to the lip retracting device 10 shown in FIGS. 21 and 21b, except that this embodiment does not include a tongue retainer. Accordingly, the description set forth above for the lip retracting device 10 applies for the alternative lip retracting device 10" less the tongue retainer.

Similarly, although not specifically shown, lip retracting device in FIG. 21b, includes formations such as the wing-like members 111, shown in FIG. 21b. These wing-like members are adapted to be fitted to a light guide having formations or an illumination frame having formations, as discussed above.

FIG. 24 shows is an exemplary semi-schematic top plan view of the lip retracting device 10 of FIG. 21 in use on a patient or user 84. As shown, the lip retracting device 10 engages the user's mouth 86 to retract the user's lips 88 and cheeks 90. Once in position, the user's mouth 86, and particularly the teeth 92, is exposed for examination and/or treatment by a health care professional. More specifically, the side channel retainers 12, 14 engage the side of the mouth, the lip channel retainers 16, 18 engage the upper and lower lips 88, and the resilient members 20 bias the four channel retainers, which bias the lips 88 and cheeks 90 open, to expose the teeth and the inside of the mouth 86. In the lip retracting device used position, the outside side walls 28b, 44b and the resilient members 20 are exposed extraorally of the mouth.

The tongue retainer 22 is shown also engaged to the tongue 94 and relegates the tongue to the back region of the mouth 86. When incorporated, the tongue retainer 22 is configured to further expose the lingual surface 96 of the teeth for examination and/or treatment.

The lip retracting device 10 may be installed on the lips 88 by first placing the upper lip over the inside side wall 44a and into the race 42 of the upper lip channel retainer 16. The two side channel retainers 12, 14 are then squeezed together and placed into the mouth, either concurrently or one at the time, until the sides of the lips fit over the inside side walls 28a of the side channel retainers 12, 14 and into the race 26. Finally, the lower lip channel retainer 18 is squeezed and placed over the lower lip 88 with the lower lip engaging the race 42 of the lip channel retainer 18. Once installed, the tongue retainer 22 automatically aligns with the tongue 94 to block the tongue from maneuverability. The lip retracting device 10 may also be installed by reversing the steps discussed above or squeezing all four channel retainers at the same time and fitting the lips over the channel retainers.

The formations such as wing-like members or flanges, not shown here, but shown in FIG. 21b, may be made of the same material as the rest of the lip retracting device or of a more sturdy polymeric material or composite. Additionally, it may also be opaque or colored even if the rest of the lip retracting device may be colorless or clear.

Figure 24A:
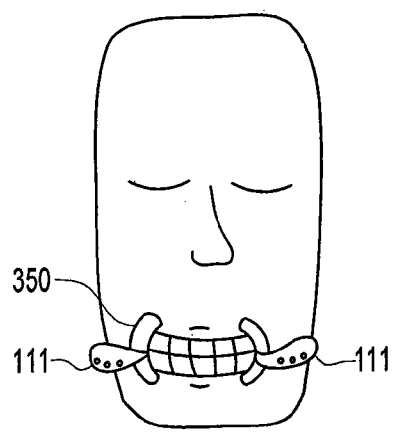
FIG. 24a depicts a semi-schematic front view of an exemplary lip retracting device coupled to a patient/user according to one embodiment of the invention.
Figure 25:
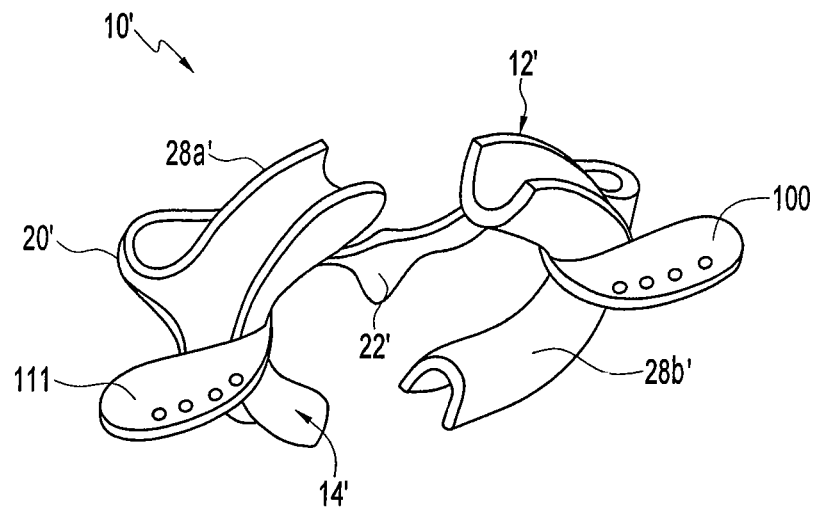
Figure 25A:
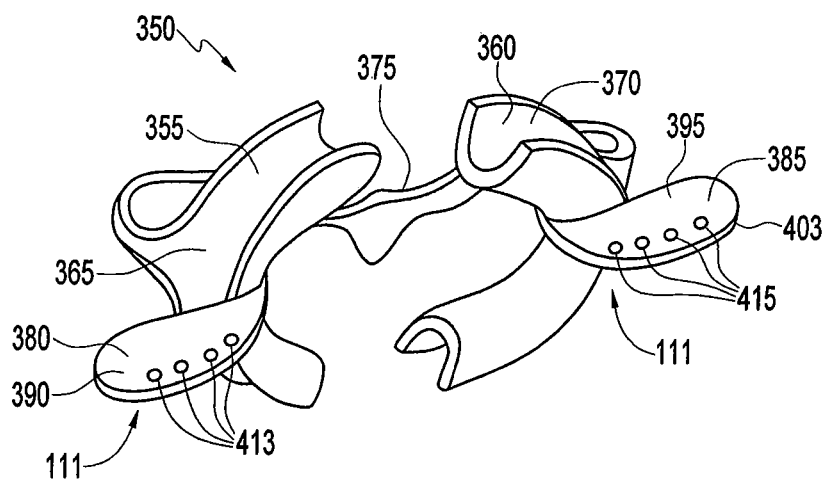
FIG. 25a depicts a perspective view of another embodiment of a lip retracting device.

FIG. 24a shows a front view of a lip retracting device 350 of FIG. 25a being worn by a person. The interface wings 111 are located at either side of the lip retracting device 350 and are available for mating with the imaging head, such as a light source 102 as shown in FIG. 1.

The lip retracting device 10' is configured to fit into the mouth in the orientation shown in FIGS. 24 and 25. In other words, in FIG. 25, the inside side walls 28a', and the tongue retractor 22' are configured to be intraoral while the outside side walls 28b', the resilient member 20' and the wing-like members 111 are configured to be extraoral.

FIG. 25a shows a lip retracting device 350 includes first 355 and second 360 semicircular "U"-shaped channels adapted to receive the lips of a dental patient adjacent to respected internal surfaces 365, 370 thereof. This is similar to FIG. 21a, but in a ready-to-use configuration. In a ready to use configuration, some of the structures takes on a different form than the not ready to use mode. A support member 375 is mutually coupled to the "U"-shaped channels 355, 360 and adapted to support the "U"-shaped channels 355, 360 in substantially fixed spatial relation with respect to one another. According to one embodiment of the invention as shown in FIG. 21a, the support member 375 also supports a tongue-cap adapted to retain a patient's tongue and shield the same from incidental illumination.

According to one embodiment of the invention, a pair of interface wings 111 is coupled to the "U"-shaped channels 355, 360 respectively. According to one embodiment of the invention, the interface wings 111 each include a respective upper surface 390, 395 and a respective lower surface 401, 403. According to one embodiment of the invention, upper surface 390 is disposed substantially parallel in relation to lower surface 401 and upper surface 395 is disposed substantially parallel in relation to lower surface 403. Pursuant to one embodiment of the invention, the interface wings 111 have a first plurality of ticks or holes 413 and a second plurality of ticks or holes 415 respectively. The ticks or holes are adapted to facilitate maintaining a particular alignment of, for example, an illumination frame (as shown in FIG. 13) 105 with respect to the lip retracting device 350.

According to one embodiment of the invention, interface wings 111 are adapted to be received within slots 236', 238' of a light guide 106, as shown in, for example, FIG. 17a, respectively. By pressing the lip retracting device 350 toward the front edge of light guide 106, the interface wings 111 are urged into slots 236' and 238', whereby the orientation and position of the lip retracting device 350 with respect to the light guide 106 is substantially fixed. Consequently, to the extent that a patient's lips effectively serve to couple the head and teeth of the patient in fixed relation to the lip retracting device 350, a target tooth is maintained in substantially fixed position with respect to a light source disposed within a lamp-head as shown, for example in FIG. 2.

Figure 25B:
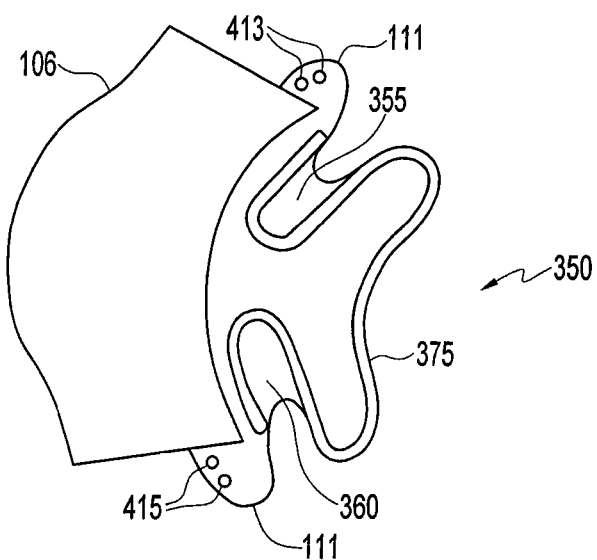
FIG. 25b shows a semi-schematic bottom plan view of the lip retracting device of FIG. 25a fitted into a light guide.

FIG. 25b shows a lip retracting device such as the lip retracting device 350 of FIG. 25a mated to a light guide 106 according to one embodiment of the invention. FIG. 25b is a top view of the mated light guide 106 and lip retracting device 350, as FIG. 22, except that the light source is not shown or the light source and the light guide may be integrally formed. The holes 413, 415 again enable the mating of the light guide 106 or the integral light guide and light source with the lip retracting device 350 to be adjusted according to the patient.

Figure 26:
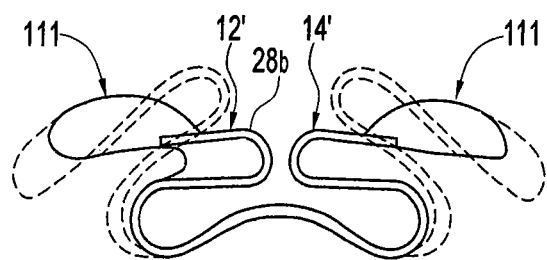
FIG. 26 depicts a semi-schematic side view of the lip retracting device of FIG. 25.

In FIG. 26, the lip retracting device 10' is shown as it would appear inside a patient's mouth with all components located inside the patient's mouth except for the wing-like flanges 111 and the outside side walls 28b', which would be outside the patient's mouth. As is readily apparent, the resilient member 20' is integrally molded to the inside side walls 28a' to not interfere with the insertion of the lip retracting device 10' into the mouth.

Figure 27:
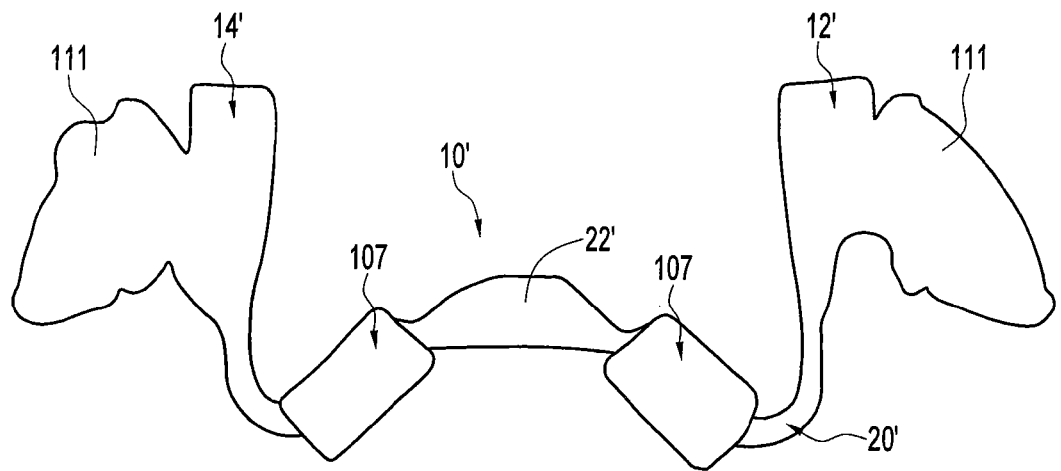
FIG. 27 depicts a semi-schematic side view of the lip retracting device of FIG. 25 fitted with pads.
Figure 28:
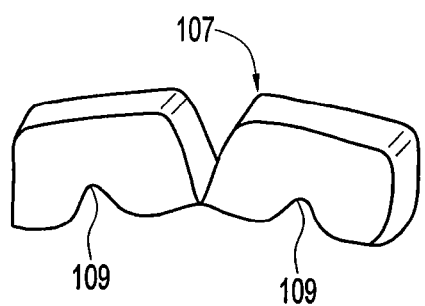
FIG. 28 depicts a semi-schematic top view of a pad having a clam-shell configuration.

Pads may be provided with the resilient member 20' to provide comfort for the patient when the patient is fitted with the lip retracting device 10'. The pads 107 may be positioned on the resilient member 20', as shown in FIG. 27. The pads (FIG. 28) may be molded out of any foam material, such as those described above for the soft overlays, which may be molded in two halves connected along one edge, like a clamshell, as shown in FIG. 28. Each half may incorporate a slot, channel, or ridge 109 for receiving at least a portion of the resilient member 20'. The two halves may be fitted around the resilient member and then heat sealed together. Other methods of assembly that may achieve the same or similar results are also contemplated. For example, the ridges 109 are so sized so that when the pad 107 is fitted over the resilient member 20', the pad is able to slide relative to the resilient member to enable adjustment to the location of the pad on the resilient member.

For example, the pads 107 are made of polyethylene closed-cell foam so that they may be sterilized. Open cell foams may also be used if they are amenable to autoclaving. Also, the pads have, for example, a smooth outside surface and smooth edges so that the pads may fit comfortably when in contact with the inside of a patient's mouth without unwanted irritation. In one embodiment, the pads may be designed to be placed over the second to the last molar when the lip retracting device 10' is inside a patient's mouth. In addition, they may be made with, for example, relatively high resiliency material so that they, for example, may return to their original shape after use.

In another embodiment, the pads 107 may be removable after each use. Here, the pads may be attached using removable adhesive or the two halves may simply be mated over the resilient member using detents or the like. Any foam material that may be made to fit comfortably inside a patient's mouth may be used as alternatives. The two-halves of the pad may also be made, for example, by heat set, to have a memory so that it may be forced open for installation onto a resilient member and be snapped shut when the opening force is removed. The two-halves may be integrally molded or attached along at least one side.

In a further embodiment, pads may be permanently affixed and may not be sterilizable, making the lip retracting device a one-patient use item.

Figure 29:
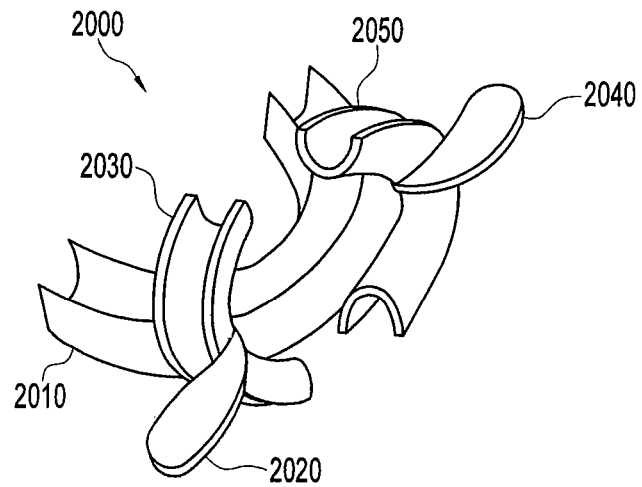
FIG. 29 depicts a perspective view of an embodiment of a lip retracting device having a u-shape channel.

FIG. 29 shows another embodiment of a lip retracting device 2000 of the present invention. The lip retracting device 2000 includes a first u-shaped channel 2010 shaped and configured to accommodate a lower, or alternatively an upper, set of a patient's teeth (not shown). The lip retracting device 2000 further includes a second u-shaped channel 2030 and a third u-shaped channel 2050 mounted substantially perpendicular to the first u-shaped channel 2010. The second and third u-shaped channels 2030, 2050 are adapted to receive the lips of the dental patient. The first u-shaped channel 2010 supports the second and third u-shaped channels 2030, 2050 in substantially fixed spatial relation with respect to one another.

According to the present embodiment of the invention, a pair of interface wings 2020, 2040 is coupled to the second and the third u-shaped channels 2030, 2050 respectively. The interface wings 2020, 2040 are shaped and configured to be received into slots 1130, 1132 in a light guide 1104, fitted to a lamp head or light source 1102, as shown in FIG. 32, in order to align the light source 1102 with the teeth of a patient. To the extent that a patient's lips effectively serve to couple a lamp head and teeth of the patient in fixed relation to the lip retracting device 1138, the lip retracting device 1138 is maintained in a substantially fixed position with respect to a light source disposed within a lamp-head as shown, for example in FIG. 32. This is described in greater detail below.

The interface wings or wing-like members, 2020, 2040, like the wing-like members of the above described lip retracting devices, typically have some rigidity so that the interface wings 2020, 2040 may form an effective interface when mated with the slots 1130, 1132 of the light guide 1104, as seen in FIG. 32. Similar to the embodiments described above, the interface wings 2020, 2040 may in a first arrangement be formed of the same material as the channels 2010, 2030, 2050. In a second arrangement, the interface wings 2020, 2040 are made of a different material from the channels 2010, 2030, 2050.

Figure 29A:
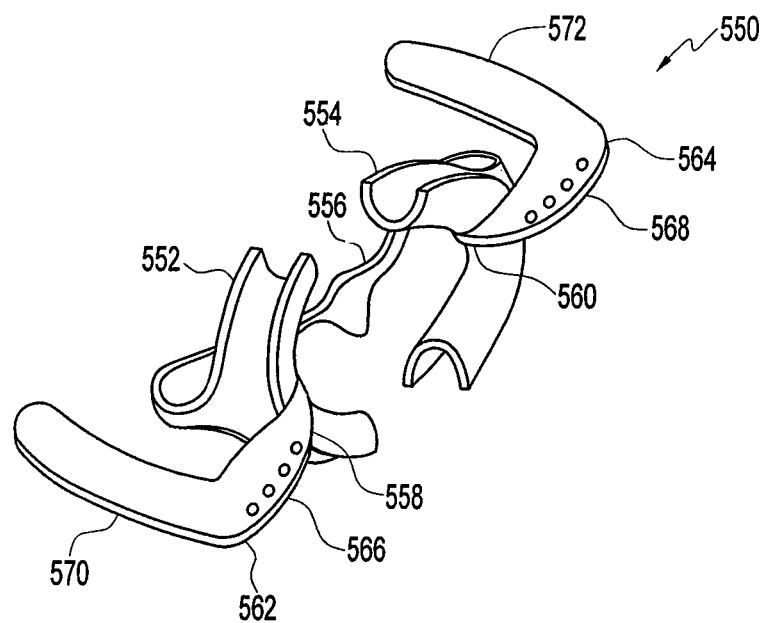
FIG. 29a shows, in perspective view, a lip retracting device having extended wings according to one embodiment of the invention.

FIG. 29a shows a lip retracting device 550 according to an alternative embodiment of the invention. The lip retracting device 550 has a first u-shaped channel 552 and a second u-shaped channel 554 to hold the lips of the patient whose teeth are to be imaged. A support member 556 is mutually coupled to the u-shaped channels 552, 554 and is adapted to support the u-shaped channels 552, 554 in substantially fixed spatial relation with respect to one another. A first end 558 of the first interface wing 562 is coupled to the first u-shaped channel 552. A first end 560 of the second interface wing 564 is coupled to the second u-shaped channel 554.

Each interface wing 562, 564 includes a first portion 566, 568 located at the front of the lip retracting device 550 away from the patient. A second portion 570, 572 of each interface wing 562, 564 extends outward and toward the back of the lip retracting device 550. In operation, the first portions 566, 568 are located at the front of the patient's face while each second portion 570, 572 is located at a side of the patient's face. The interface wings 562, 564 are adapted to be received within the slots 236, 238 of the beam guide 106. The first portions 566, 568 enable the beam guide 106 to be aligned to the front of the patient. The second portions 570, 572 of the interface wings 562, 564 enable the beam guide 106 and imaging head 102 to be aligned on either side of the patient's head.

Figure 29B:
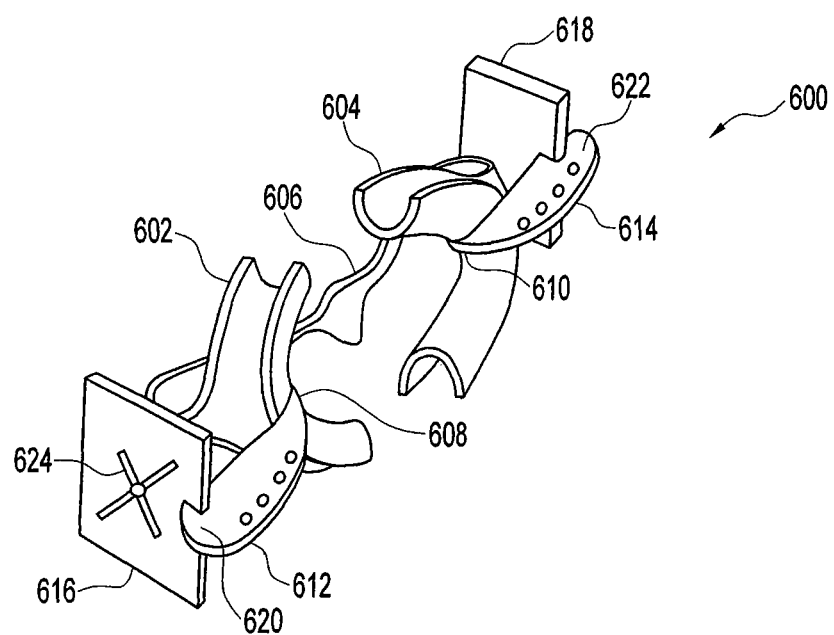
FIG. 29b shows, in perspective view, a lip retracting device including targets according to one embodiment of the invention.

FIG. 29b shows a lip retracting device 600 according to an alternative embodiment of the invention. The lip retracting device 600 has a first u-shaped channel 602 and a second u-shaped channel 604 to hold the lips of the patient whose teeth are to be imaged. A support member 606 is mutually coupled to the u-shaped channels 602, 604 and is adapted to support the u-shaped channels 602, 604 in substantially fixed spatial relation with respect to one another. A first end 608 of the first interface wing 612 is coupled to the first u-shaped channel 602. A first end 610 of the second interface wing 614 is coupled to the second u-shaped channel 604. The interface wings 612, 614 are adapted to be received within the slots 236, 238 respectively of the beam guide 106. A target 616, 618 is coupled to a second end 620, 622 of the first interface wing 612 and second interface wing 614 respectively. Each target 616, 618 has alignment markings 624. In operation, the targets 616, 618 act as visual alignment mechanisms for the imaging head 102 for side images of the patient's teeth.

Figure 29C:
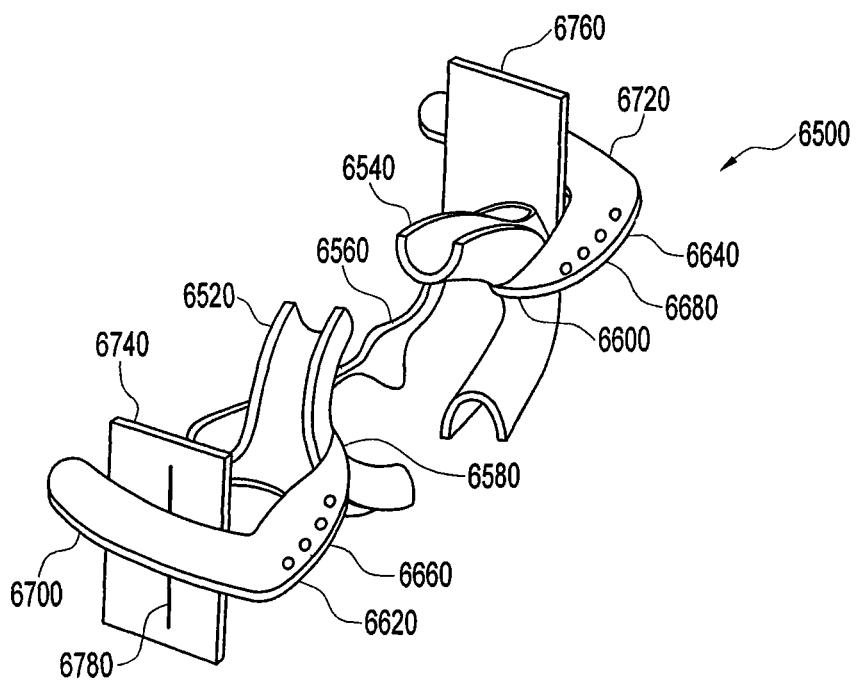
FIG. 29c shows, in perspective view, a lip retracting device with extended wings and targets according to an embodiment of the invention.

FIG. 29c shows a lip retracting device 6500 according to an alternative embodiment of the invention. The lip retracting device 6500 has a first u-shaped channel 6520 and a second u-shaped channel 6540 to hold the lips of the patient whose teeth are to be imaged. A support member 6560 is mutually coupled to the u-shaped channels 6520, 6540 and is adapted to support the unshaped channels 6520, 6540 in substantially fixed spatial relation with respect to one another.

A first end 658 of the first interface wing 6620 is coupled to the first unshaped channel 6520. A first end 6600 of the second interface wing 664 is coupled to the second unshaped channel 6540. Each interface wing 6620, 6640 includes a first portion 6660, 6680 located at the front of the lip retracting device 6500 away from the patient. A second portion 5700, 5720 of each interface wing 6620, 6640 extends outward and toward the back of the lip retracting device 6500. In operation, the first portions 6660, 6680 are located at the front of the patient's face while each second portion 6700, 6720 is located at a side of the patient's face. The interface wings 6620, 6640 are adapted to be received within the slots 236, 238 of the beam guide 106. The first portions 6660, 6680 enable the beam guide 106 to be aligned to the front of the patient. The second portions 6700, 6720 of the interface wings 6620, 6640 enable the beam guide 106 and imaging head 102 to be aligned on either side of the patient's head.

A target 6740, 6760 is coupled to the second portions 6700, 6720 of the first interface wing 6620 and second interface wing 6640 respectively. Each target 6740, 6760 has visual alignment markings 6780. In operation, the targets 6740, 6760 act as visual alignment mechanisms for the imaging head 102 for side images of the patient.

Figure 29D:
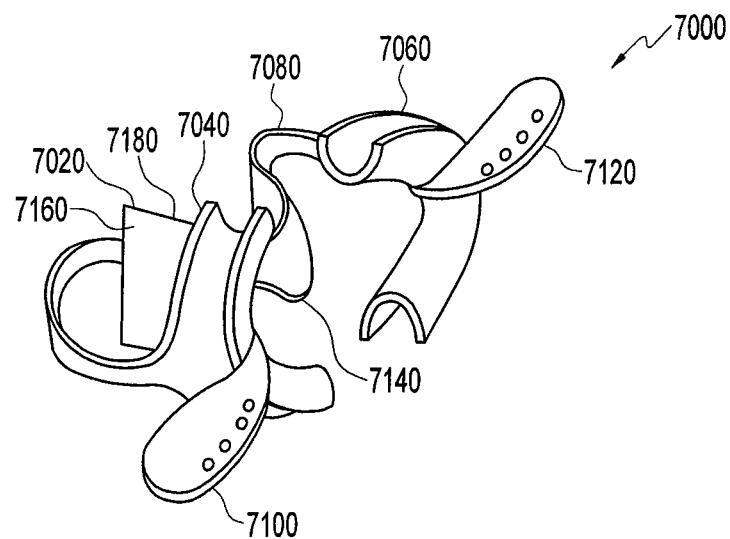
FIG. 29d shows, in perspective view, a lip retracting device including a film holder according to an embodiment of the invention.

FIG. 29d shows a lip retracting device 7000 according to one embodiment of the invention. The lip retracting device 7000 is also a fixturing device for maintaining the imaging head 102 (as shown in FIG. 1) in substantially fixed relation with respect to a target tooth. Further, the lip retracting device 7000 holds film inside the teeth of the patient in a manner in which the patient does not actively participate in the holding. In bite-wing images, for example, the patient must bite down on a portion of the film holder in order to maintain the imaging film in a proper position. For people with poor muscle control, biting down for even a short period of time may be difficult. A film holder 7020 attached to the lip retracting device 7000 as described below does not require the active participation of the patient to hold the film in place.

As shown in the illustrated embodiment, the lip retracting device 7000 includes first 7040 and second 7060 semicircular "U"-shaped channels adapted to receive the lips of a dental patient as described above with respect to FIG. 25a. A support member 7080 is mutually coupled to the "U"-shaped channels 7040, 7060 and adapted to support the "U"-shaped channels 7040, 7060 in substantially fixed spatial relation with respect to one another. According to one embodiment of the invention, a pair of interface wings 7100, 7120 are coupled to the "U"-shaped channels 7040, 7060 respectively. According to one embodiment of the invention, interface wings 7100, 7120 are adapted to be received within slots 236, 238 respectively (as shown in FIG. 17a).

The support member 7080 is shaped and configured to support a film holder 7020. In one embodiment, the film holder 7020 is an integral part of the lip retracting device 7000. In an alternative embodiment, the film holder 7020 is separably coupled to the lip retracting device 7000. With the lip retracting device 7000 held in place by the patient's lips in the unshaped channels 7040, 7060, the film in the film holder 7020 is also held in place. The lip retracting device 7000 is symmetric and accordingly the film holder could be located on either side of the central portion 7140 of the support member 7080. In an alternative embodiment of the invention, the support member 7080 is configured to support two film holders 7020, one on either side of the central portion 7140 of the support member 7080. In this embodiment, the front 7160 of the film holder 7020 is x-ray penetrable while the back 7180 of the film holder 7020 blocks x-rays. In a first arrangement, the front 7160 of the film holder 7020 is made of an x-ray penetrable material while the back 7180 of the film holder 7020 is made of an x-ray blocking material. In a second arrangement, an x-ray blocking lining is inserted behind the film in the film holder 7020.

Figure 29E:
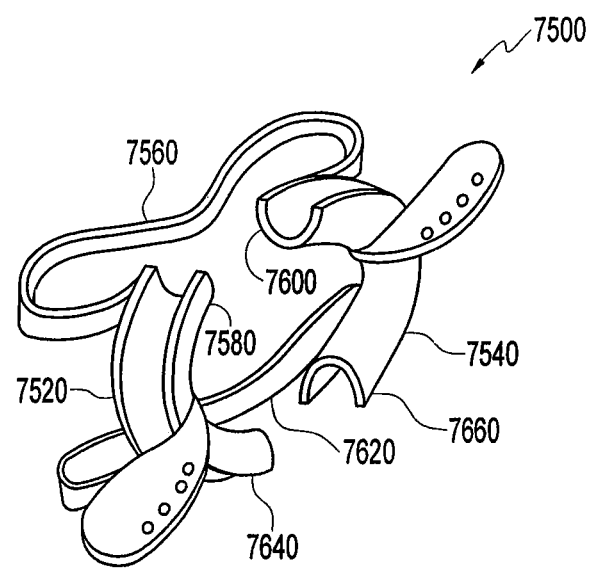
FIG. 29e shows, in perspective view, an alternative configuration of a lip retracting device.

FIG. 29e shows a lip retracting device 7500 according to one embodiment of the invention. The lip retracting device 7500 is also a fixturing device for maintaining the imaging head 102 in substantially fixed relation with respect to a target tooth. Further, the lip retracting device 7500 improves access to the patient's mouth so that film may be inserted and removed easily in order to make a series of images.

As shown in the illustrated embodiment, the lip retracting device 7500 includes first 7520 and second 7540 semicircular "U"-shaped channels adapted to receive the lips of a dental patient. A first support member 7560 is mutually coupled to first ends 7580, 7600 of the u-shaped channels 7520, 7540. A second support member 7620 is mutually coupled to second ends 7640, 7660 of the u-shaped channels 7520, 7540. The support members 7560, 7620 are adapted to support the u-shaped channels 7520, 7540 in substantially fixed spatial relation with respect to one another. The support members 7560, 7620 leave a space between them that enables film to be inserted into the patient's mouth for imaging purposes while the u-shaped channels 7520, 7540 hold the patient's lips clear.

In the present embodiment of the invention, a pair of interface wings 7680, 7700 are coupled to the "U"-shaped channels 7520, 7540. The interface wings 7680, 7700 are adapted to be received within slots 1140, 1160 respectively of the beam guide 1000 (shown in FIG. 16) where the imaging head 102 is located at the front of the patient. In an alternative embodiment, the interface wings 7680, 7700 are extended as in the embodiment illustrated in FIG. 29a. The extended interface wings enable the imaging head 102 to be positioned at either side of the patient's head.

Figure 30:
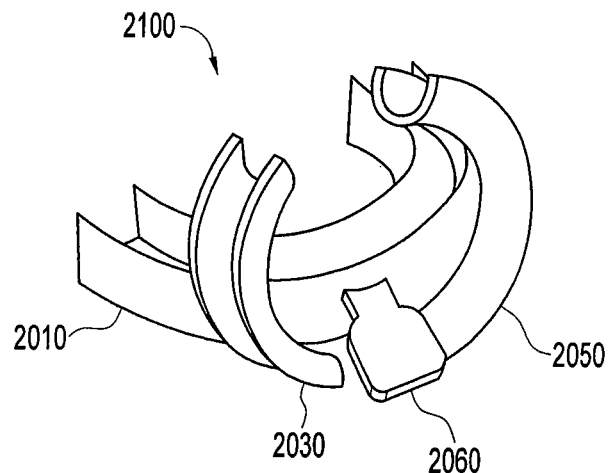
FIG. 30 depicts a perspective view of an embodiment of a lip retracting device having a u-shape channel with a tab.

FIG. 30 shows a lip retracting device 2100 having a first u-shaped channel 2010 mutually coupled to a second u-shaped channel 2030 and third u-shaped channel 2050 which are substantially perpendicular to the first u-shaped channel 2010. A tab 2060 is coupled to the first u-shaped channel 2010 between the second and third u-shaped channels 2030, 2050. The tab 2060 is useful for positioning the lip retracting device 2100 in the mouth of the dental patient. Later, after completion of the whitening process, the tab 2060 is useful for removing the lip retracting device 2100 from the mouth of the dental patient.

Figure 31:
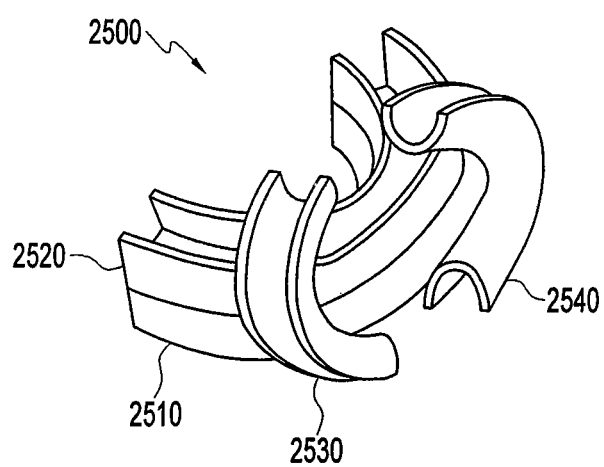
FIG. 31 shows, in perspective view, a lip retracting device accommodating both lower and upper sets of teeth according to one embodiment of the invention.

FIG. 31 is an alternative embodiment of the lip retracting device according to principles of the invention. The lip retracting device 2500 includes a lower jaw u-shaped channel 2510 and an upper jaw u-shaped channel 2520. The lower jaw u-shaped channel 2510 is shaped and configured to accommodate the lower set of the patient's teeth (not shown) while the upper jaw u-shaped channel 2520 is shaped and configured to accommodate the upper set of the patient teeth (not shown). Both the lower jaw u-shaped channel 2510 and the upper jaw u-shaped channel 2520 are adapted to receive a treatment composition, such as a whitening composition. The lip retracting device 2500 further includes a first u-shaped lip retracting device channel 2530 and a second unshaped lip retracting device channel 2540. The first and second unshaped lip retracting device channels 2530, 2540 are mounted substantially perpendicular to the lower jaw u-shaped channel 2510 and upper jaw unshaped channel 2520. The lower jaw unshaped channel 2510 and upper jaw unshaped channel 2520 support the a first unshaped lip retracting device channel 2530 and a second unshaped lip retracting device channel 2540 in substantially fixed spatial relation with respect to one another. The first and second unshaped lip retracting device channels 2530, 2540 are shaped and configured to receive the lips of the dental patient.

In operation, the lower jaw unshaped channel 2510 and the upper jaw unshaped channel 2520 receive a whitening composition. The lower jaw unshaped channel 2510 and the upper jaw u-channel shaped 2520 are then fitted over a patient's teeth so that the treatment composition such as a whitening composition is in contact with the patient's teeth. The patient's lips are received into the first and second unshaped lip retracting device channels 2530, 2540. Using the dental lip retracting device of the present embodiment, a dental process such as a whitening process may be performed on the lower teeth and the upper teeth at the same time effectively reducing the overall duration of the session.

FIG. 32 shows an assembly relationship between the ball joint 902 the lamp head 1102, a light guide 1104, and a lip retracting device 1138 according to one embodiment of the invention. As shown in FIG. 20, a pivot mount 906 is coupled between the lamp head 1102 and the ball joint 902. The ball joint allows the lamp head to be swiveled in space such that an optical axis of the curing lamp is aligned with the target teeth of a dental whitening subject.

A light guide 1104 is adapted to be coupled to an anterior end of the lamp head 1102. In one embodiment, the light guide 1104 includes an inner surface region 1122 that is adapted to be held in proximity to an outer surface region 1124 of the lamp head 1102. According to one embodiment of the invention, a projecting member, or bump, on inner surface 1122 is adapted to be urged into a recessed region 1126 of outer surface region 1124.

In one embodiment of the invention, the light guide 1104 includes an elastically compressible cushion 1128 at an anterior edge thereof. The elastically compressible cushion 1128 serves to soften an interface between a dental whitening process subject (not shown) and the light guide.

In a further aspect of the invention, as shown in the illustrated embodiment, the light guide 1104 includes first and second slots 1130 and 1132. These slots are adapted to receive projecting wings 1134, 1136 of a lip retracting device 1138 so as to stabilize a relationship between the dental whitening subject and the lamp head 1102.

The lip retracting device 1138 includes channels 1140, 1142 adapted to support the lips of a dental whitening subject during the whitening process, and an elastic member 1144. The elastic or elastomeric member 1144 is coupled to the channels 1140, 1142 and adapted to urge the channels outwardly towards the lips, so as to couple the subject undergoing the dental process to the lip retracting device.

When the subject is coupled to the lip retracting device 1138, and the lip retracting device is coupled to the light guide 1104 by the insertion of wing-like members 1134, 1136 in the respective slots 1130, 1132 in the light guide 1104, the subject is spatially stabilized with respect to the lamp head 1102. In this way the support structure serves to support the lamp head in a substantially stable spatial relationship to the whitening subject.

Figure 32A:
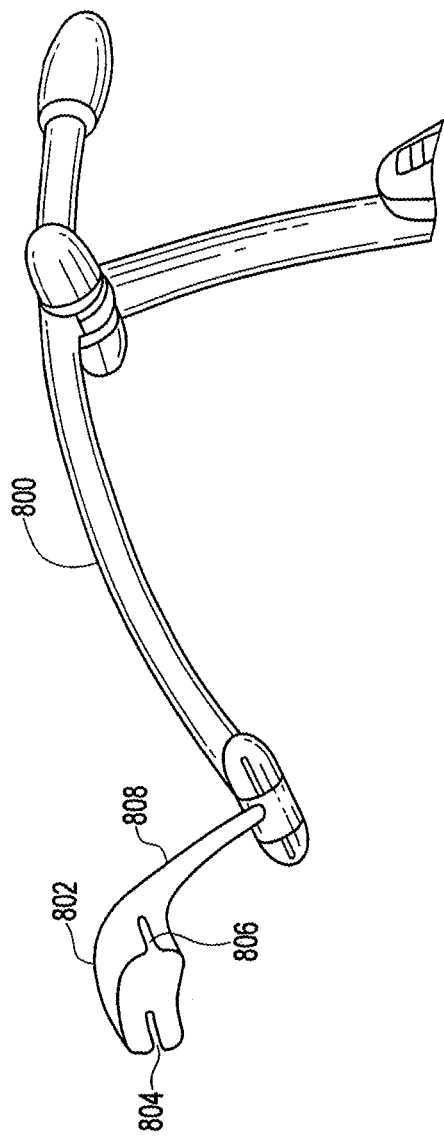
FIG. 32a shows, in perspective view a stationary imaging stand according to one embodiment of the invention.

FIG. 32a shows an imaging support stand 800 suitable for use with certain types of imaging apparatus, such as panoramic x-ray devices. A patient to be imaged holds a position in relation to the support stand 800 while an imaging device (not shown) travels around the patient's head. The support stand 800 includes a coupling device 802 that enables the patient to hold the position.

The coupling device 802 is attached to the imaging support stand 800 by a support member 808. The support member 808 is coupled to the coupling device 802 and the imaging support stand 800. The support member 808 is, in one embodiment, adjustably coupled to the support stand 800 by a ball and socket joint that enables desired positioning of the coupling device.

The coupling device 802 is similar to the slotted beam guide 106, as shown for example in FIG. 16. The coupling device 802 is shaped and configured to mate with a lip retracting device with interface wings such as the lip retracting device 350 with interface wings 111 shown in FIG. 25a. The coupling device 802 has a first slot 804 and a second slot 806 adapted to couple with interface wings 111. By pressing the lip retracting device 350 toward the front edge of the coupling device 802, the interface wings 111 are urged into the slots 804, 806 whereby the orientation and position of the lip retracting device 350 is substantially fixed. Accordingly, the orientation and position of the patient's head is also fixed.

Figure 32B:
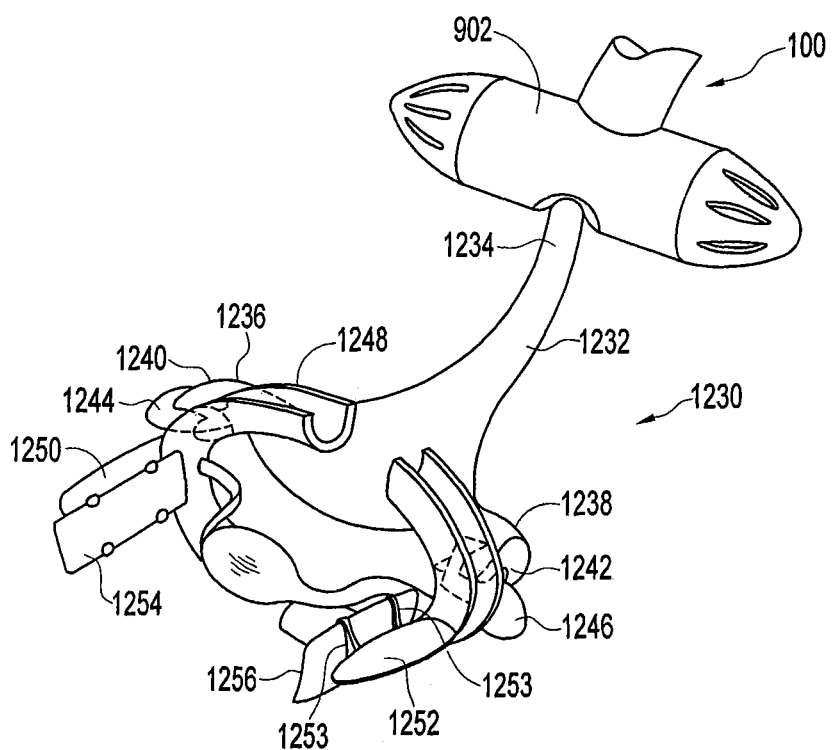
FIG. 32b shows an embodiment of the invention including a dental support structure and a dental imaging fixturing system.

FIG. 32b shows another embodiment of the invention including a dental support structure 100 that is adapted to support a dental imaging fixturing system 1230. In the illustrated embodiment, the ball joint 902 is coupled to a support member 1232. The support member 1232 includes a first elongate portion 1234 having at its posterior end the ball of the ball and socket joint 902. An anterior end of the support member 1232 includes, in the illustrated embodiment, first and second wing-coupling members 1236, 1238. Each wing-coupling member 1236, 1238 includes a respective slot 1240, 1242. The slots 1240, 1242 are adapted to receive corresponding wings 1244, 1246 of a lip retracting device 1248.

When the lip retracting device 1248 is worn by a dental procedure subject, insertion of the wings 1244, 1246 into the slots 1240, 1242 serves to stabilize a spatial relationship between the subject and the one or more x-ray sources.

According to one embodiment of the invention, as illustrated, the lip retracting device 1248 includes first and second bite members 1250, 1252. Each bite member 1250, 1252 has a respective one or more film support clips 1253 adapted to support a respective x-ray film package.

In operation, at least one x-ray film package is coupled to the one or more film support clips 1253. The x-ray film package, as is known in the art, includes a sheet of chemical x-ray film enclosed in a light-tight package. The lip retracting device 1248 is coupled to a dental x-ray subject by placing the lips of the patient into the lip-receiving channels of the lip retracting device 1248. The subject then bites down on the bite members to further secure the lip retracting device in a stable spatial relationship to the teeth of the subject. By inserting the wings 1244, 1246 into slots 1240, 1242, the lip retracting device 1248 is stabilized with respect to the dental support structure 100. This serves to stabilize the teeth of the subject and the x-ray film package 1256 with respect to the floor, and thus with respect to an x-ray source. Consequently, the well-known tendency of x-ray subjects to move during exposure of the x-ray film with a resulting non-uniformity of film exposure, is reduced.

Figure 32C:
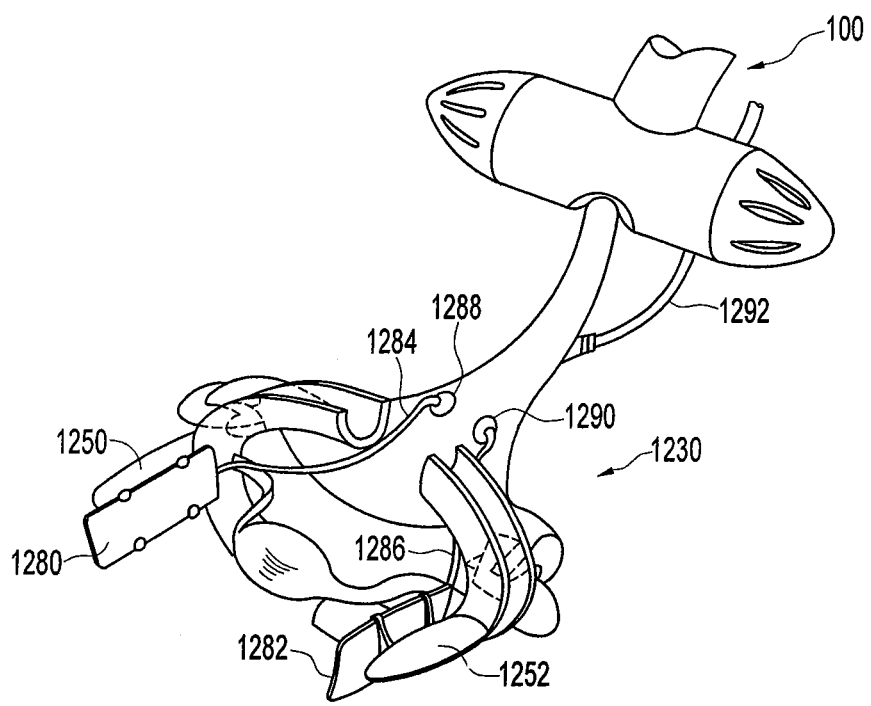
FIG. 32c shows another embodiment of the invention including a dental support structure and a dental imaging fixturing system.

FIG. 32c shows a further embodiment of the invention including a dental support structure 100 that is adapted to support a dental imaging fixturing system 1230.

Unlike the embodiment of FIG. 32b, the FIG. 32c embodiment includes electronic x-ray sensors 1280, 1282 coupled to the bite members 1250, 1252 respectively. Detecting and imaging x-rays with an electronic image sensor may be preferable to using chemical film because electronic image sensors tend to be more sensitive than chemical film, no chemical developing process is required, and the digital images produced by most electronic image sensors are immediately ready for digital manipulation.

In one embodiment of the invention, electronic image sensors each include a respective signal cable with a removable plug.

As discussed above, this spatially stabilized relationship between a subject and the support structure of the invention is found in other embodiments of the invention and in relation to various apparatus and processes.

The use of light guides of the present invention may also promote less air circulation between the patient's mouth and the ambient surroundings. With less air circulation inside the mouth, there may be less evaporation of any treatment composition or whitening composition, which may lead to less dehydration of the mouth. Without wishing to be bound by a theory, it is surmised that since dehydration may lead to increased sensitivity, less dehydration of the mouth may lead to decreased dehydration of the teeth and thus decreased teeth sensitivity during and after treatment. Thus, the use of a light guide during bleaching process may potentially be advantageous.

Figure 33:
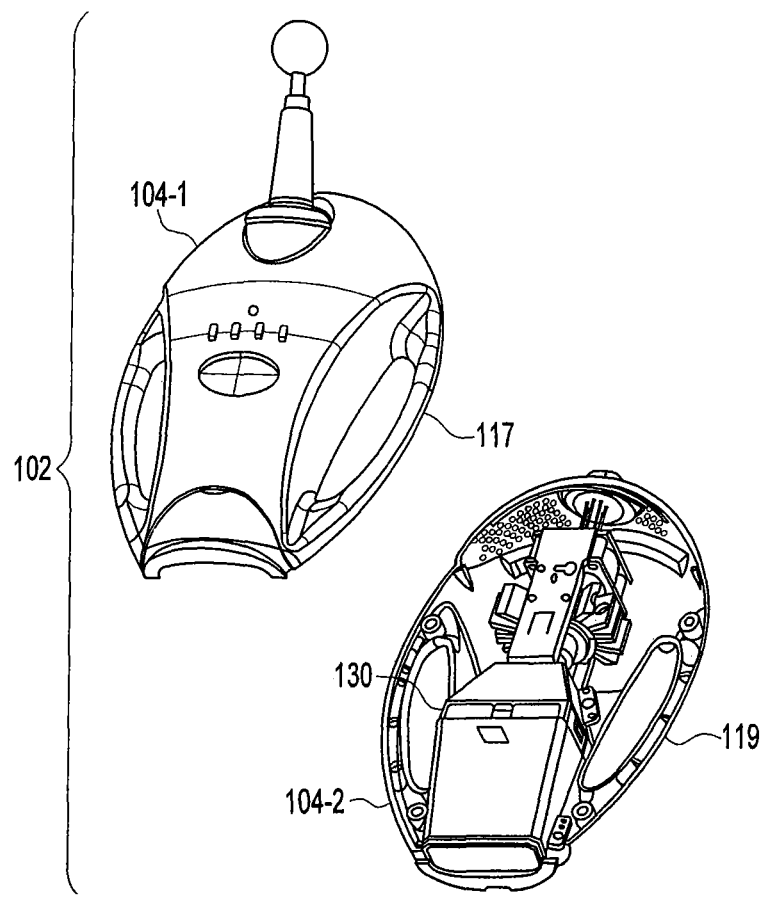
FIG. 33 shows, in perspective view, components of a lamp head according to one embodiment of the invention.

FIG. 33 is a perspective view of a partially disassembled lamp head 102 showing the top lamp head case, bottom lamp head case and the light head assembly in place in the bottom lamp head case. The upper head housing 104-1 is separated from the lower head housing 104-2. The lamp subassembly 130 can be seen in place in the lower head housing 104-2. The upper head housing 104-1 has a first lapped rim 117 and the lower head housing 104-2 has a second lapped rim 119. The first lapped rim 117 and the second lapped rim 119 are configured to mate with one another when the upper head housing 104-1 is mated to the lower head housing 104-2. The mated lapped rims 117, 119 provide a measure of protection against light, for example UV light, escaping through the joint between the upper head housing 104-1 and lower head housing 104-2. The lapped joint is illustrated in FIG. 12.

Figure 34:
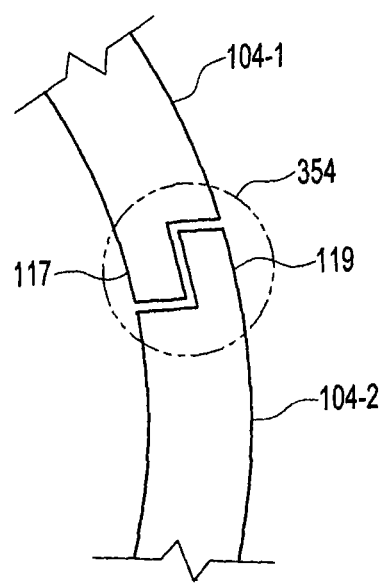
FIG. 34 shows, in a side cross-sectional view, a lapped joint of a lamp head according to one embodiment of the invention.

FIG. 34 is a side cross-sectional view of the lapped joint of the top lamp head case and bottom lamp head case according to principles of the invention. FIG. 34 is a side cross-sectional view of the lapped joint formed when the upper head housing 104-1 is mated to the lower head housing 104-2. The upper head housing 104-1 has a first lapped rim 117 and the lower head housing 104-2 has a second lapped rim 119. The first lapped rim 117 and second lapped rim 119 are configured to mate as shown to form a lapped joint 354. The lapped joint 354 is a lamp safety feature as it substantially blocks light from escaping the lamp head 102 through the joint 354. Light leakage, for example UV light leakage, is potentially harmful to both the lamp operator and to the patient having whitening treatment.

Figure 35:
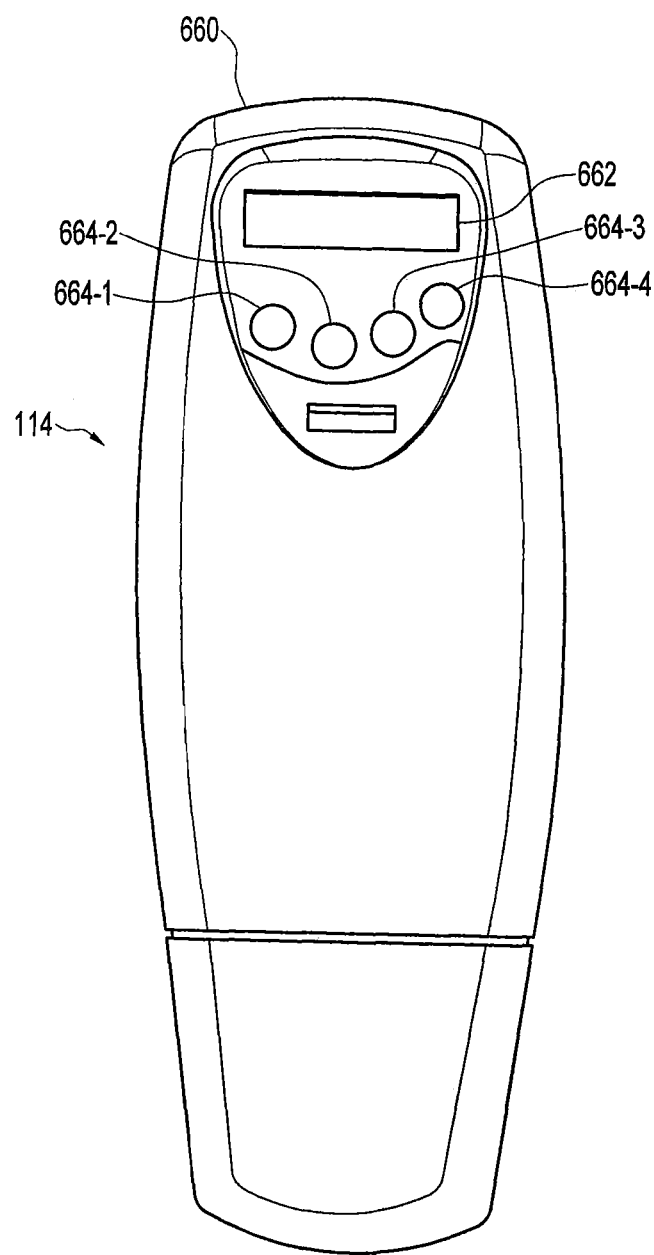
FIG. 35 shows a view of a power pack according to one embodiment of the invention.

FIG. 35 is a view of the power pack of the lamp of FIG. 1. The power pack 114 is mountable on the mast 110 as shown in FIG. 1. Various conventional mounting techniques (not shown) are applicable to mount the power pack 114 to the mast 110. The power pack 114 interfaces the power and I/O cables (not shown). The power pack 114 includes a control area 660. In this embodiment, the control area 660 includes a display window 662 and a plurality of control buttons 664-1, 664-2, 664-3, 664-4. The display window 662 displays, for example, elapsed treatment time or other treatment process information. The control buttons are, for example, "on", "off", "start", and "pause." The lamp operator operates the lamp system 100 using the controls and display on the control pack. Together with the indicators on the lamp head 102, the operator is able to monitor the lamp system 100 during treatment.

Figure 36:
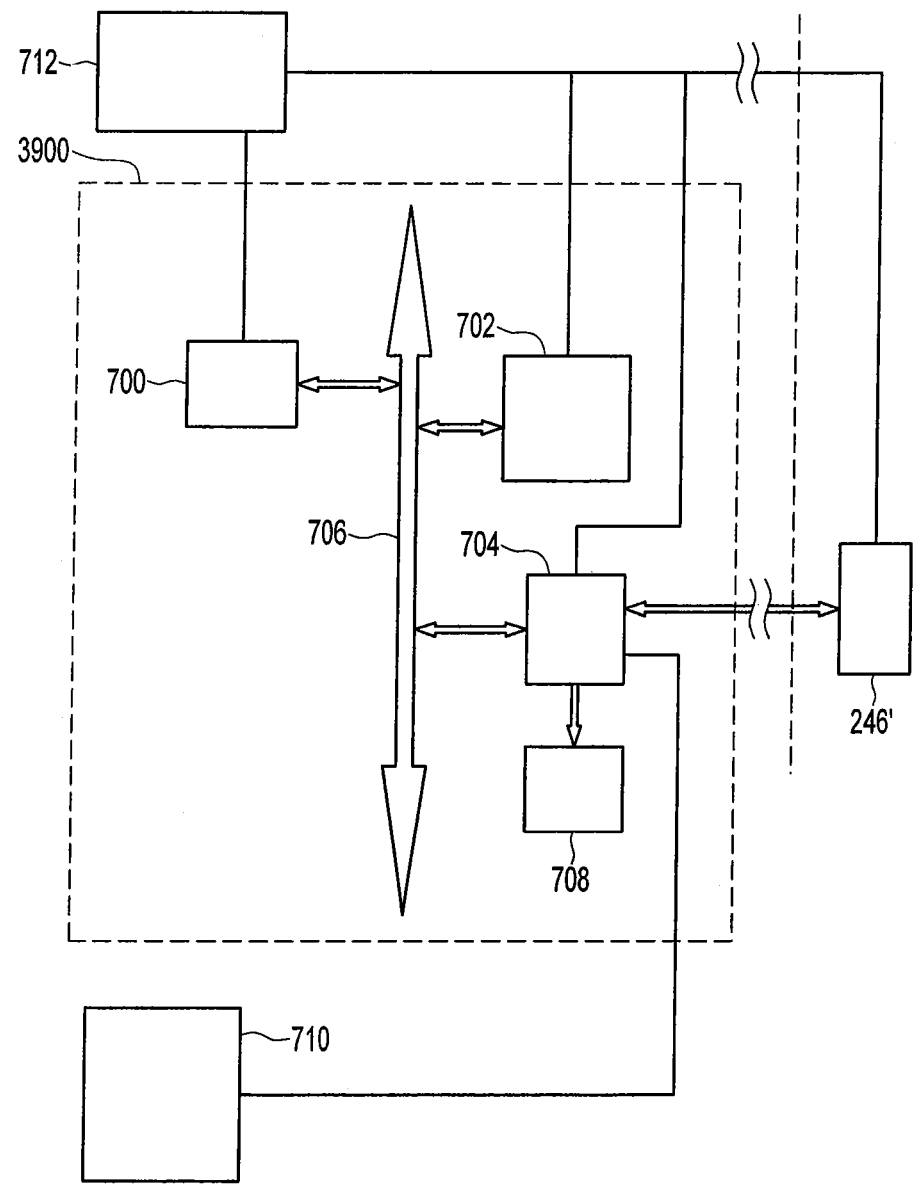
FIG. 36 shows, in block diagram form a control system for a dental lamp according to one embodiment of the invention.

FIG. 36 is a block diagram of an embodiment of the control system 3900 of the lamp system 100 of the present invention. In one embodiment, the microelectronics of the control system 3900 are located in the lamp head 102. In another embodiment, the microelectronics of the control system 3900 are located in the power pack 114. Other locations for the control system electronics are possible within the scope of the invention.

The control system 3900 includes a CPU 700, program memory logic 702, an I/O logic device 704, a data bus 706 and system indicators 708. The CPU 700, program memory logic 702, and the I/O logic device 704 are connected to the data bus 706. The I/O logic device 704 is further connected to system indicators 708. In one embodiment of the invention, the I/O logic device 704 further includes device drivers. The I/O logic device 704 is further connected to the memory integrated circuit 246' located on the light guide (shown in FIG. 17a). Lamp controls 710 are connected to the I/O device 704. A power source 712 provides power to the CPU 700, program memory logic 702, the I/O logic device 704 and the memory integrated circuit 246'.

The CPU 700, program memory logic 702 and the I/O logic device 704 are for example, microelectronic devices located in the lamp head 102. The program memory logic stores lamp usage limits, which includes a light source usage limit, a light guide usage limit, and a procedure time limit. In an alternative embodiment of the invention, the lamp controls 710 and power 712 are also located in the lamp head 102. In an alternative embodiment of the invention, the CPU 700, program memory logic 702, I/O logic device 704, lamp controls 710, and power 712 are, for example, located in the power pack 114. The lamp controls 710 are, for example, a transistor device or electronic or electro-mechanical relay device for controlling the on/off function of the lamp system 100. The system indicators 708 are, for example, the lighted indicators 150, 152 shown on the lamp head 102 in FIG. 6.

Figure 37:
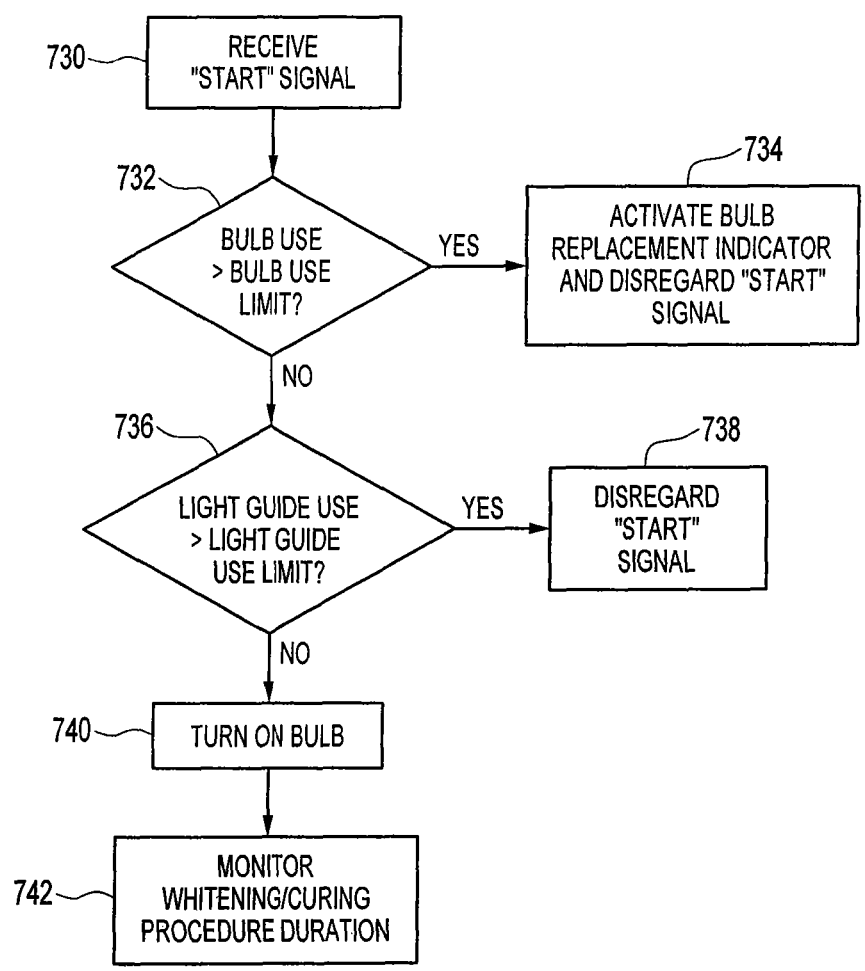
FIG. 37 is a flow chart of the start process of the control system of FIG. 35.

FIG. 37 is a flow chart showing one embodiment of the start process of the lamp system that is executed by the control system illustrated in FIG. 14.

At step 730, the control system 3900 receives a "start" signal from the lamp controls 710. The "start" signal activates an initializing process that includes determining whether the light source 300 and light guide have reached their usage limits. The control system 3900 stores a light source usage limit, a light guide usage limit, and a whitening/curing procedure time limit that is divided into preselected time periods.

At step 732, the control system 3900 checks whether the light source 300 has been used longer than the light source usage limit stored in the control system 3900. The light source usage limit is, for example, 100 hours. The control system 3900, as will be described with regard to FIG. 16, monitors the time that the source 300 is on and adds this value to the amount of time accumulated from previous treatment procedures, if any. When the "start" signal is received from the lamp controls 710, the control system 3900 compares the accumulated light source on time with the light source usage limit. If the light source usage limit has been exceeded, the control system 3900 proceeds to step 734. If the light source usage limit has not been exceeded, the control system 3900 proceeds to step 736.

At step 734, the control system 3900 activates the light source replacement indicator 152 in the lamp head 102. In a first embodiment of the control system 3900, the control system continues with the process of starting the lamp system 100. In this embodiment, the control system 3900 proceeds to step 736. In a second embodiment of the control system 3900, the control system 3900 does not allow the lamp to be turned on. In this embodiment, the control system 3900 proceeds to step 738. In either embodiment, the control system 3900 is reset when the light source 300 is replaced.

At step 736, the control system 3900 determines whether the light guide usage has exceeded the light guide usage limit stored in the control system 3900. The light guide usage limit is typically the amount of time of a single whitening or curing treatment. The light guide usage limit is, for example, sixty minutes. The control system 3900, as mentioned above in step 732, monitors the time that the light source 300 is on. The control system 3900 writes the amount of time that the light source 300 has been on since the beginning of a treatment procedure to a recording device on the light guide 106. The recording device is, for example, a memory integrated circuit 246'. When the "start" signal is received from the lamp controls 710, the control system 3900 compares the light source "on" time stored on the recording device in the light guide 106 with the light guide use limit stored by the control system 3900. If the light guide use limit has been exceeded, the control system 3900 proceeds to step 738. If the light guide use limit has not been exceeded, the control system 3900 proceeds to step 740.

At step 738, the control system 3900 disregards the "start" signal with regard to turning the light source 300 on. That is, the control system 3900 does not allow the lamp system 100 to operate if the light guide lifetime has expired. This portion of the control system 3900 acts to prevent the light guide from being reused. The light guide 106 is intended to be a single-use device to be discarded after each whitening or curing treatment.

At step 740, the control system 3900 starts the lamp (i.e. turns on the light source 300).

At step 742, the control system 3900 monitors the whitening or curing treatment procedure time. In this step, the control system 3900 monitors the time that the light source 300 is on. The monitoring procedure of the control system 3900 is described below with regard to FIG. 16.

Figure 38:
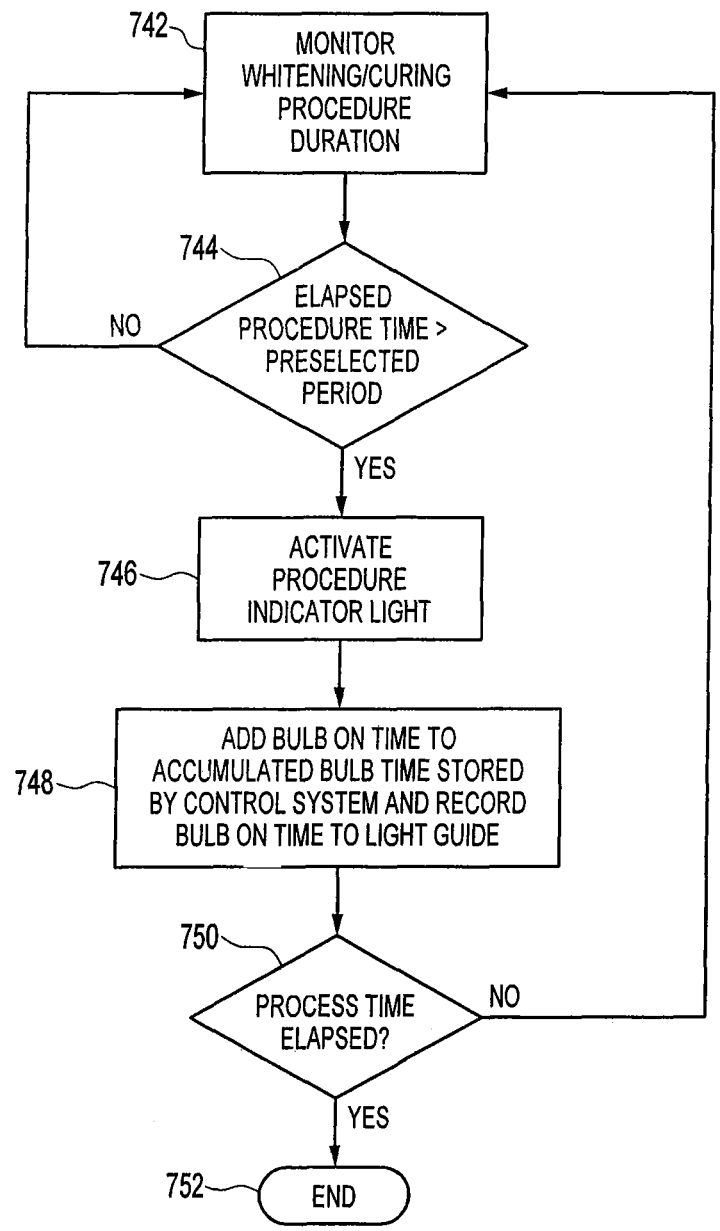
FIG. 38 is a flow chart of the lamp system monitoring process of the control system of FIG. 35.

FIG. 38 is a flow chart showing one embodiment of the monitoring process of the lamp system that is executed by the control system illustrated in FIG. 14.

At step 742, the control system 3900 monitors the duration of the whitening or curing treatment, that is, the control system 3900 monitors the light source "on" time.

At step 744, the control system 3900 determines whether the elapsed procedure time has exceeded a preselected time period. Here, the preselected time period is some portion of the overall treatment time such as one quarter of the total treatment time. If the elapsed procedure time has not exceeded the preselected time period, the control system 3900 continues to monitor the treatment duration (step 742). If the elapsed procedure time does exceed the preselected time period, then the control system 3900 proceeds to step 746.

At step 746, the control system 3900 activates a procedure indicator light, for example one of the lighted indicators 150 described above with regard to FIG. 6. In one embodiment, the control system 3900 activates another lighted indicator 150 as each treatment portion time elapses so that if, for example, there are four lighted indicators, all four are lit at the end of the treatment procedure. In another embodiment, there is a single lighted indicator to indicate the time progression of the treatment. In this embodiment, the light indicator has varying flash rates to indicate the how much time has elapsed since the start of treatment. The control system 3900 then proceeds to step 748. In yet another embodiment, a voice alert system is used to alert the dental professional of the progress of the treatment, as described above.

At step 748, the control system 3900 adds the time that the light source has been on to the accumulated time that the control system 3900 has stored from previous treatment procedures, if any. The control system 3900 also writes the time that the light source has been on to the light guide recording device, such as the memory integrated circuit 246'. The control system 3900 then proceeds to step 750.

At step 750, the control system 3900 determines whether the overall process time has elapsed. The overall process time is the time duration of the whitening or curing treatment. If the overall process time has not elapsed, the control system 3900 returns to step 742, monitoring the whitening/curing duration. If the overall process time has elapsed, the control system 3900 proceeds to step 752.

At step 752, the duration of the whitening/curing treatment has elapsed and the control system 3900 turns off the light source 300.

While exemplified embodiments of the invention have been described and illustrated above, it should be understood that these are exemplary of the invention and are not to be considered as limiting. Accordingly, the invention is not to be considered as limited by the foregoing description, but is only limited by the scope of the claims appended hereto.

The invention claimed is:

1. A dental illumination apparatus comprising:
   a lamp system mounted on a support structure, the lamp system including a lamp head housing and a light source disposed within the housing;
   a light guide with a lamp attachment formation coupled to the lamp head housing of said lamp system such that a surface region of the lamp head housing is disposed adjacent to and supported by an internal surface of the light guide, the light guide further including a lip retractor attachment formation;
   a control mechanism, further comprising a recording medium, on the light guide for controlling the activation of the lamp system; and
   a lip retractor, adapted to be inserted into a patient's mouth, coupled to said lip retractor attachment formation of said light guide, said lip retractor including geometric formations adapted to receive one or more lips of said patient;
   wherein said lip retractor and light guide maintain illumination from said lamp system in a constant position relative to said patient's mouth.

2. The dental illumination apparatus of claim 1 wherein said control mechanism controls the activation during attachment of the light guide to the lamp system.

3. The dental illumination apparatus of claim 1 further comprising a signal generating device in communication with said recording medium.

4. The dental illumination apparatus of claim 3 wherein said control mechanism comprises receipt by the recording medium of a signal from the signal generating device, and recording of a record of the recording medium corresponding to the received signal to produce a substantially permanent signal record.

5. The dental illumination apparatus of claim 3 wherein said signal generating device and said recording medium are located within the lamp system.

6. The dental illumination apparatus of claim 1 wherein said control mechanism comprises a control device external to the light guide, said control device allows or inhibits activation of the lamp system.

7. The dental illumination apparatus of claim 1 further comprising an electrical control device, in electronic communication with said lamp system, for controlling the duration of use of the light guide to a predetermined amount of time.

8. The dental illumination apparatus of claim 7 wherein said electrical control device inhibits the activation of the lamp system when the predetermined amount of time has expired.

9. The dental illumination apparatus of claim 7 wherein said electrical control device comprises a microprocessor and a switch.

10. The dental illumination apparatus of claim 9 wherein said electrical control device comprises receipt by the recording medium of a signal from the signal generating device, and recording of a record of the recording medium corresponding to the received signal to produce a substantially permanent signal record.

11. The dental illumination apparatus of claim 9 further comprising a signal reading device.

12. The dental illumination apparatus of claim 11 wherein said signal generating device and said recording medium are located within the lamp system.

13. The dental illumination apparatus of claim 1, wherein said geometric formations comprise channel retainers for retaining two corresponding portions of the patient's lips.

14. The dental illumination apparatus of claim 1, wherein said geometric formations include a U-shaped channel.

15. The dental illumination apparatus of claim 1, wherein said geometric formations include first and second U-shaped channels.

16. A dental illumination apparatus comprising:
   a lamp system mounted to a support structure, the lamp system including a lamp head housing and a light source disposed within the housing;
   a light guide with a lamp attachment formation removably coupled to said lamp head housing of said lamp system, such that a surface region of the lamp head housing is disposed adjacent to and supported by an internal surface of the light guide, the light guide further including a lip retractor attachment formation and a recording medium;
   a lip retractor, adapted to be inserted into a patient's mouth to retract the patient's lips, coupled to said lip retractor attachment formation of said light guide, the lip retractor including at least one U-shaped channel; and
   a control mechanism comprising a reading device for reading the recording medium to ascertain a condition of use of the light guide containing the recording medium;
   wherein said lip retractor and light guide maintain illumination from said lamp system in a constant position relative to said patient's mouth.

17. The dental illumination apparatus of claim 16 wherein said reading device comprises a control device external to the light guide.

18. The dental illumination apparatus of claim 17 wherein said control device serves to allow or inhibit activation of the lamp system.

19. The dental illumination apparatus of claim 16 wherein said control mechanism further comprises a signal generating source.

20. The dental illumination apparatus of claim 19 wherein said recording medium receives a signal from the signal generating source, and records a record corresponding to the received signal to produce a substantially permanent signal record.

21. The dental illumination apparatus of claim 19 wherein said signal from the signal generating source is received at the recording medium by means of an electromechanical coupling; an optical communication channel; a mechanical communication channel; an acoustic communication channel; or a radio frequency communication channel.

* * * * *